(12) United States Patent
Harra et al.

(10) Patent No.: US 8,259,299 B2
(45) Date of Patent: Sep. 4, 2012

(54) GAS SCANNING AND ANALYSIS

(75) Inventors: David James Harra, Scotts Valley, CA (US); Rick Eugene Sanner, Sun Valley, NV (US); Mark Norman Iverson, Reno, NV (US)

(73) Assignee: RF Science & Technology Inc., Reno, NV (US)

( * ) Notice: Subject to any disclaimer, the term of this patent is extended or adjusted under 35 U.S.C. 154(b) by 309 days.

(21) Appl. No.: 12/621,467

(22) Filed: Nov. 18, 2009

(65) Prior Publication Data

US 2010/0058833 A1    Mar. 11, 2010

Related U.S. Application Data

(63) Continuation-in-part of application No. 11/821,481, filed on Jun. 21, 2007.

(60) Provisional application No. 61/115,767, filed on Nov. 18, 2008, provisional application No. 61/116,417, filed on Nov. 20, 2008, provisional application No. 61/116,959, filed on Nov. 21, 2008, provisional application No. 61/117,056, filed on Nov. 21, 2008.

(51) Int. Cl.
*G01N 21/00* (2006.01)
(52) U.S. Cl. .......................... 356/437; 356/433; 73/23.2
(58) Field of Classification Search .......... 356/432–435, 356/437–444; 73/23.35, 23.2; 250/393
See application file for complete search history.

(56) References Cited

U.S. PATENT DOCUMENTS

| | | |
|---|---|---|
| 3,768,054 A | 10/1973 | Neugebauer |
| 4,428,366 A | 1/1984 | Findl et al. |
| 4,582,985 A | 4/1986 | Löfberg |
| 4,672,346 A | 6/1987 | Miyamoto et al. |
| 4,679,426 A | 7/1987 | Fuller et al. |
| 4,765,179 A | 8/1988 | Fuller et al. |
| 4,801,209 A * | 1/1989 | Wadlow ........................ 356/417 |
| 4,875,486 A | 10/1989 | Rapoport et al. |
| 4,975,581 A | 12/1990 | Robinson et al. |
| 4,993,068 A | 2/1991 | Piosenka et al. |

(Continued)

FOREIGN PATENT DOCUMENTS

EP         0 350 546 A2     1/1990

(Continued)

OTHER PUBLICATIONS

Active Spectrum, Inc., "What is Electron Spin Resonance (ESR)?", website http://www.activespectrum.com/about.html, available at least by Jul. 30, 2009.

(Continued)

*Primary Examiner* — Layla Lauchman
(74) *Attorney, Agent, or Firm* — Woodcock Washburn LLP

(57) ABSTRACT

Systems and methods for scanning and analyzing characteristics of a gas sample utilizing electromagnetic radiation are disclosed. More particularly, the systems and methods utilize an electromagnetic radiation source connected to a transmitter and an analyzer connected to a receiver. A sample gas volume to be analyzed is placed between the transmitter and receiver and a frequency sweep of electromagnetic radiation is transmitted through the sample to create a series of spectral data sets, which are developed into a composite spectrogram by the analyzer and processed to determine the one or more characteristics of the sample. A magnetic field can alternatively be applied around the transmitter, receiver and sample to enhance some characteristic analysis applications and to make other characteristic analysis applications possible.

12 Claims, 27 Drawing Sheets

U.S. PATENT DOCUMENTS

| | | | |
|---|---|---|---|
| 5,050,607 | A | 9/1991 | Bradley et al. |
| 5,063,934 | A | 11/1991 | Rapoport et al. |
| 5,072,732 | A | 12/1991 | Rapoport et al. |
| 5,320,103 | A | 6/1994 | Rapoport et al. |
| 5,328,822 | A | 7/1994 | McKinney et al. |
| 5,363,052 | A | 11/1994 | McKee |
| 5,372,136 | A | 12/1994 | Steur et al. |
| 5,411,023 | A | 5/1995 | Morris, Sr. et al. |
| 5,415,163 | A | 5/1995 | Harms et al. |
| 5,435,169 | A | 7/1995 | Mitra |
| 5,462,054 | A | 10/1995 | Rapoport et al. |
| 5,487,870 | A | 1/1996 | McKinney et al. |
| 5,508,203 | A | 4/1996 | Fuller et al. |
| 5,565,834 | A | 10/1996 | Hanley et al. |
| 5,575,977 | A | 11/1996 | McKinney et al. |
| 5,592,086 | A | 1/1997 | Weinstock et al. |
| 5,626,137 | A | 5/1997 | Dumoulin et al. |
| 5,680,460 | A | 10/1997 | Tomko et al. |
| 5,744,958 | A | 4/1998 | Werne |
| 5,792,668 | A | 8/1998 | Fuller et al. |
| 5,894,221 | A | 4/1999 | Watanabe et al. |
| 6,011,858 | A | 1/2000 | Stock et al. |
| 6,016,476 | A | 1/2000 | Maes et al. |
| 6,035,398 | A | 3/2000 | Bjorn |
| 6,038,666 | A | 3/2000 | Hsu et al. |
| 6,043,881 | A * | 3/2000 | Wegrzyn et al. ............... 356/316 |
| 6,061,587 | A | 5/2000 | Kucharczyk et al. |
| 6,107,627 | A * | 8/2000 | Nakagawa et al. ........... 250/292 |
| 6,110,660 | A | 8/2000 | Kriz et al. |
| 6,147,490 | A | 11/2000 | Watanabe |
| 6,184,684 | B1 | 2/2001 | Dumoulin et al. |
| 6,263,228 | B1 | 7/2001 | Zhang et al. |
| 6,309,884 | B1 | 10/2001 | Cooper et al. |
| 6,477,398 | B1 | 11/2002 | Mills |
| 6,480,141 | B1 | 11/2002 | Toth et al. |
| 6,529,617 | B1 | 3/2003 | Prokoski |
| 6,614,238 | B1 | 9/2003 | Jean et al. |
| 6,723,048 | B2 | 4/2004 | Fuller |
| 6,780,378 | B2 * | 8/2004 | Abbasi et al. ................... 422/78 |
| 6,862,466 | B2 | 3/2005 | Ackerman |
| 6,864,826 | B1 | 3/2005 | Stove |
| 6,987,393 | B2 | 1/2006 | Jean et al. |
| 6,995,558 | B2 | 2/2006 | Butters et al. |
| 7,081,747 | B2 | 7/2006 | Butters et al. |
| 7,184,810 | B2 | 2/2007 | Caduff et al. |
| 7,221,169 | B2 | 5/2007 | Jean et al. |
| 7,228,163 | B2 | 6/2007 | Ackerman |
| 7,315,767 | B2 | 1/2008 | Caduff et al. |
| 7,316,649 | B2 | 1/2008 | Fuller |
| 7,347,365 | B2 | 3/2008 | Rowe |
| 7,349,556 | B2 | 3/2008 | Brooks |
| 7,449,695 | B2 | 11/2008 | Zimdars et al. |
| 7,685,433 | B2 | 3/2010 | Mantyjarvi et al. |
| 7,705,988 | B2 * | 4/2010 | Richman ........................ 356/437 |
| 7,781,736 | B2 * | 8/2010 | Logan et al. ............. 250/339.07 |
| 2002/0009213 | A1 | 1/2002 | Rowe et al. |
| 2003/0083563 | A1 | 5/2003 | Katsman et al. |
| 2003/0128867 | A1 | 7/2003 | Bennett |
| 2003/0133596 | A1 | 7/2003 | Brooks |
| 2004/0147819 | A1 | 7/2004 | Caduff et al. |
| 2005/0090726 | A1 | 4/2005 | Ackerman |
| 2005/0113650 | A1 | 5/2005 | Pacione et al. |
| 2005/0269412 | A1 | 12/2005 | Chiu et al. |
| 2006/0080551 | A1 | 4/2006 | Mantyjarvi et al. |
| 2007/0237365 | A1 | 10/2007 | Monro |
| 2007/0255141 | A1 | 11/2007 | Esenaliev et al. |
| 2007/0290800 | A1 | 12/2007 | Fuller |
| 2008/0057526 | A1 | 3/2008 | Caduff et al. |
| 2008/0192988 | A1 | 8/2008 | Uludag et al. |
| 2008/0319293 | A1 | 12/2008 | Looney et al. |
| 2009/0156915 | A1 | 6/2009 | Cross |

FOREIGN PATENT DOCUMENTS

| | | |
|---|---|---|
| FR | 2 562 785 A1 | 10/1985 |
| GB | 1360 606 A | 7/1974 |
| JP | 56-14145 | 10/1981 |
| WO | 99/32897 A2 | 7/1999 |
| WO | 01/47415 A1 | 7/2001 |
| WO | WO 2008/156787 | 12/2008 |
| WO | WO 2010/059744 | 5/2010 |

OTHER PUBLICATIONS

Wikipedia, "Electron Paramagnetic Resonance", website http://www.en.wikipedia.org/wiki/Electron_paramagnetic_resonance, available at least by Aug. 12, 2009.

Poor, Alfred, "On the Light Side: Security is All in Vein", website http://www.ecnmag.com/Lightside-Securty-all-in-Vein-011609.aspx, Feb. 2, 2009.

Falco et al., Abstract: "Approaching the inverse problem of the multilayer skin system", Solianis Monitoring AG, Zurich Switzerland; and Applied Physics Dept., The Hebrew University of Jerusalem, Israel, 2008.

Caduff, et al., Abstract: Non-invasive Glucose Monitoring in Patients with Type 1 Diabetes: Repeatability in the same Subjects, R&D, Solianis Monitoring, Zurich Switzerland, Seminar for Statistics, ETH Zurich, Zurich, Switzerland, Centre for clinical research, University Hospital Zurich, Zurich, Switzerland, Clinic for Endocrinology and Diabetes, University Hospital Zurich, Zurich Switzerland and Research, Profil Institute for Metabolic Research, Neuss, Germany, 2008.

Caduff et al., Abstract: "Testing a Multisensor Concept under Simulated Home Use Conditions for non invasive Glucose Monitoring", Solianis Monitoring AG, Zurich Switzerland, Centre for clinical research, University Hospital Zurich, Zurich, Switzerland, Clinic for Endocrinology and Diabetes, University Hospital Zurich, Zurich, Switzerland and Seminar for Statistics, ETH Zurich, Switzerland 2008.

Livshits et al., Abstract: "The Study of the Dielectric Response of Red Blood Cells to Sugar Exposure—In vitro Basis for Non-invasive Glucose Impedance Monitoring", Department of Applied Physics, The Hebrew University of Jerusalem, Jerusalem, Israel, and Solianis Monitoring AG, Zurich, Switzerland, 2008.

Huber et al., Abstract: "The Compensation of Perturbation Effects in Glucose Monitoring Technologies Based on Impedance Spectroscopy", Solianis Monitoring, Zurich, Switzerland; Swiss Federal Laboratories for Materials Testing and Research, St. Gallen, Switzerland; Cantonal Hospital of St. Gallen, St. Gallen, Switzerland; and Institute for Clinical Research and Development, Mainz, Germany, 2008.

Pene, Matt, "Baylor Researcher Creates New Way to Test Blood-Sugar Level", Baylor University website http://www.baylor.edu/pr/news.php?action=story&story=49271, Feb. 18, 2008.

Pindi, "Non-Invasive Diagnostics for Measuring Blood and Protecting Identity" (Pindi existing website, including technology presentations, slide show: medical uses for RMM, slide show II: personal security with RMM and all related materials), website download http://pindi.com/, Apr. 19, 2007.

Smith, John L., Article: "The Pursuit of Non-Invasive Glucose: Hunting the Deceitful Turkey", copyright 2006.

Caduff et al., Abstract: "Non invasive Glucose Monitoring—Next steps in an approach to address perturbing effects in an IS based monitoring technique", ADA Abstract 2006 Solianis, Zurich, Switzerland, 2006.

Caduff et al., Abstract: "Variations in Blood Glucose and their impact on various Blood Parameters in Healthy Subjects", DTM, Solianis Monitoring, Zurich, Switzerland and Profit Inst. For Metabolic Research, Neuss, Germany, 2006.

Talary et al., Abstract: "Biological application of impedance spectroscopy for in vivo life sign and Non invasive Glucose Monitoring", Biodielectrics, Solianis Monitoring AG, Zurich, Switzerland, 2006.

Livshits et al., Abstract: "The Study of the Dielectric Response of Red Blood Cells to Sugar Exposure—In vitro Basis for Non-invasive Glucose Impedance Monitoring", Department of Applied Physics, The Hebrew University of Jerusalem, Jerusalem, Israel and Solianis Monitoring AG, Zurich, Switzerland, 2005.

Active Spectrum, Inc., "Benchtop Micro-ESR", product literature, San Carlos, California, available no earlier than 2005.

Westerhoff et al., "Mechanisms for the interaction between nonstationary electric fields and biological systems II. Nonlinear dielectric theory and free-energy transduction", Ferroelectrics, 1988, vol. 86, pp. 79-101, Gordon and Breach Science Publishers S.A. United States of America, Oct. 1, 1988.

Furukawa et al., "Measurements of Nonlinear Dielectricity in Ferroelectric Polymers", Japanese Journal of Applied Physics, 1987, vol. 26, No. 7, pp. 1039-1045, Japan, Apr. 25, 1987.

Liszi et al., "Field-dependent Kirkwood Factor in the Non-linear Dielectric Behaviour of Binary Liquid Mixtures", J. Chem. Soc., Faraday Trans. 1, 1982, vol. 78, pp. 915-922.

Author Unknown, "RealStream technology related to industrial analysis application:", Excerpt from yet2.com, website download, date unknown.

Meszarous et al., "Applicability of the Intermodulation Technique for the Nonlinear Behavior of Dielectric Materials", publication information unknown, date unknown. This reference was cited in an earlier filed provisional application by Milton Fuller who is deceased. This reference cannot be found in the assignee's or inventor's files available to assignee and the reference no longer appears to be available to the public. Applicants' and their counsel's knowledge of this reference is limited to its citation in the provisional application.

Kell, D., Title and publication information unknown, date unknown. This reference was cited in an earlier filed provisional application by Milton Fuller who is deceased. This reference cannot be found in the assignee's or inventor's files available to assignee and the reference no longer appears to be available to the public. Applicants' and their counsel's knowledge of this reference is limited to its citation in the provisional application.

Gulich et al., "Dielectric spectroscopy on aqueous electrolytic solutions", Radiat Environ Biophys 48, pp. 107-114, 2009.

Gilbert et al., "Kinetic EPR studies of the addition of carbohydrate-derived radicals to methacrylic acid", J. Chem. Soc., Perkin Trans. 2, pp. 1565-1572, 1998.

Mathur et al., "Dielectric Spectroscopy: Choosing the Right Approach", website http://license.icopyright.net/user/viewFreeUse.act?fuid=Njc0MDkzOA%3D%3D, Pharm Tech.com. Sep. 2008. Available at least by Jan. 9, 2010.

Feldman et al., "Time domain dielectric spectroscopy. A new effective tool for physical chemistry investigation", Colloid and Polymer Science, vol. 270, pp. 768-780, 1992.

Fruhstorfer, Heinrich, Heinrich, "Frequent lancing for monitoring blood glucose may cause skin changes", Pract Diab Int vol. 23 No. 5, Marburg, Germany, Jun. 2006.

Gottman et al., "Self-Monitoring Effects in a Program for Potential High School Dropouts: A Time-Series Analysis", Journal of Consulting and Clinical Psychology, vol. 39, No. 2, pp. 273-281, 1972.

Baker, et al., "Self-Monitoring May Be Necessary for Successful Weight Control", Behavior Therapy 24, pp. 377-394, 1993.

Schnoll, et al., "Self-regulation training enhances dietary self-efficacy and dietary fiber consumption", Journal of the American Dietetic Association, vol. 101, No. 9, pp. 1006-1011, Sep. 2001.

Kopelman, Peter G., "Obesity as a medical problem", Nature, vol. 404, pp. 635-643, Apr. 2000.

Liszi et al., "Field-dependent Kirkwood Factor in the Non-Linear Dielectric Behaviour of Binary Liquid Mixtures", J. Chem. Soc., Faraday Trans. 1, 1982, 78(3), 915-922.

\* cited by examiner

|  | G1 | G2 | G3 | G4 | G5 | G6 | G7 | G8 | G9 | G10 | G11 | G12 |
|---|---|---|---|---|---|---|---|---|---|---|---|---|
| R | R1 | R1 | R1 | R1 | R1 | R1 | R1 | R1 | R1 | R1 | R1 | R1 |
| A | R2 | R2 | R2 | R2 | R2 | R2 | R2 | R2 | R2 | R2 | R2 | R2 |
| T | R3 | R3 | R3 | R3 | R3 | R3 | R3 | R3 | R3 | R3 | R3 | R3 |
| I | R4 | R4 | R4 | R4 | R4 | R4 | R4 | R4 | R4 | R4 | R4 | R4 |
| O | R5 | R5 | R5 | R5 | R5 | R5 | R5 | R5 | R5 | R5 | R5 | R5 |
| S | ⋮ | ⋮ | ⋮ | ⋮ | ⋮ | ⋮ | ⋮ | ⋮ | ⋮ | ⋮ | ⋮ | ⋮ |
|  | R639 | R639 | R639 | R639 | R639 | R639 | R639 | R639 | R639 | R639 | R639 | R639 |

FIG. 14

|        | $R^2$ | Slope | Intercept |
|--------|-------|-------|-----------|
| R      |       |       |           |
| A      |       |       |           |
| T      |       |       |           |
| I      |       |       |           |
| O      |       |       |           |
| S      |       |       |           |

FIG. 15

GAS SCANNING AND ANALYSIS

CROSS-REFERENCES TO RELATED APPLICATIONS

This application is a continuation-in-part of, and claims priority to U.S. patent application Ser. No. 11/821,481, filed Jun. 21, 2007, which is incorporated herein by reference, and also takes priority from provisional patent application Ser. Nos. 61/115,767, filed 18 Nov. 2008; 61/116,417, filed 20 Nov. 2008; 61/116,959, filed 21 Nov. 2008; and 61/117,056, filed 21 Nov. 2008, all of which are incorporated herein by reference. This application is related to co-pending U.S. patent application Ser. No. 11/447,537, filed Jun. 5, 2006, titled "Biometric Identification and Authentication System Using Electromagnetic Frequency Response"; U.S. patent application Ser. No. 11/821,481, filed Jun. 21, 2007, titled "Sample Scanning and Analysis System and Methods for Using the Same"; U.S. patent application Ser. No. 12/621,475, filed Nov. 18, 2009, titled "Non-Invasive Weight and Performance Management"; U.S. patent application Ser. No. 12/621,483, filed Nov. 18, 2009, titled "Non-Invasive Determination of Characteristics of A Sample"; and U.S. patent application Ser. No. 12/621,470, filed Nov. 18, 2009, titled "Non-Invasive Scanning Apparatuses".

BRIEF DESCRIPTION OF THE INVENTION

Systems and methods for scanning and analyzing characteristics of a gas sample utilizing electromagnetic radiation are disclosed. More particularly, the systems and methods utilize an electromagnetic radiation source connected to a transmitter and an analyzer connected to a receiver. A sample gas volume to be analyzed is placed between the transmitter and receiver and a frequency sweep of electromagnetic radiation is transmitted through the sample to create a series of spectral data sets, which are developed into a composite spectrogram by the analyzer and processed to determine the one or more characteristics of the sample. A magnetic field can alternatively be applied around the transmitter, receiver and sample to enhance some characteristic analysis applications and to make other characteristic analysis applications possible.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Many current gas analysis techniques are carried out using gas chromatography (GC) coupled with a detection method such as flame ionization, thermal conductivity, thermionic emission, discharge ionization, electron capture, helium ionization, photo-ionization, mass spectroscopy (MS), infrared spectrophotometry, electrolytic conductivity, and other detection techniques. Although all are clearly adequate for certain tasks, several exhibit low sensitivity or are completely insensitive towards certain functional groups or towards non-combustible gases such as $H_2O$, $CO_2$, $SO_2$, and $NO_x$. A number of these methods require expensive, bulky equipment and skilled operators. Others employ a radioactive source which means, in the United States, their use in the workplace, shipping and disposal are all federally regulated. In addition, several are destructive (i.e., the sample being tested is consumed by the test), time consuming with regard to sample collection, transportation, storage and separation, and therefore are not ideally suited for outside laboratory applications, such as on the scene analysis, in-home daily patient monitoring, or prescreening diagnosis in a hospital or clinic. As a result, nearly all of these gas detection methods are inadequate as stand-alone detectors for many specific applications and must be used in tandem in order to obtain the desired information.

An air pollutant is any substance in the air that can cause harm to humans or the environment (Air Pollutants. 9 Sep. 2009. USEPA. 10 Sep. 2009 http://www.epa.gov/ebtpages/airairpollutants.html). Commonly, air pollutants are classified as either primary or secondary. Primary pollutants are substances directly emitted from a process, such as ash from a volcanic eruption, carbon monoxide from a motor vehicle exhaust or sulfur dioxide released from a factory. Secondary pollutants are not emitted directly; instead, they form in the air when primary pollutants react or interact with other compounds. An example of a secondary pollutant is ground level ozone—one of the many secondary pollutants that make up photochemical smog.

In addition, air pollutants may be natural or man-made and may take the form of solid particles, liquid droplets or gases. Examples of common air pollutants include sulfur oxides ($SO_x$), nitrogen oxides ($NO_x$), carbon monoxide, carbon dioxide, volatile organic compounds (VOCs), toxic metals, chlorofluorocarbons (CFCs), ammonia, persistent organic pollutants (POPs), and radioactive pollutants.

The World Health Organization states that 2.4 million people die each year from causes directly attributable to air pollution, with 1.5 million of these deaths attributable to indoor air pollution. It is estimated that worldwide more deaths per year are linked to air pollution than to automobile accidents. Direct causes of air pollution deaths include aggravated asthma, bronchitis, emphysema, lung and heart diseases, and respiratory allergies.

Greenhouse gases are gases in the atmosphere that absorb and emit radiation within the thermal infrared range and therefore greatly affect the temperature of the Earth. The main greenhouse gases in the Earth's atmosphere are water vapor, carbon dioxide, methane, nitrous oxide ($N_2O$), and ozone. The total set of greenhouse gas (GHG) emissions caused by an organization, event or product is known as a carbon footprint. For simplicity of reporting, a carbon footprint is often expressed in terms of the amount of carbon dioxide, or its equivalent of other GHGs, emitted.

Human activities since the start of the industrial era in the mid-18$^{th}$ century have increased the levels of greenhouse gases in the Earth's atmosphere. The 2007 assessment report compiled by the Intergovernmental Panel on Climate Change (IPCC) noted that "changes in atmospheric concentrations of greenhouse gases and aerosols, land cover and solar radiation alter the energy balance of the climate system", and concluded that "increases in anthropogenic greenhouse gas concentrations is very likely to have caused most of the increases in global average temperatures since the mid-20th century."

Unfortunately, at the present there are no known efficient and accurate devices or methods for the continuous, real-time detection and quantification of the wide range of components, desirable or undesirable, found in air. For example, the detection of VOCs alone traditionally involves collecting a sample at the site, transporting the sample to a laboratory, and preparing the sample for analysis. While this method is effective and accurate, it cannot be used for continuous on-line analysis to provide information on a real-time basis as required for effective pollution control and for meeting regulatory requirements.

To address these shortcomings, U.S. Pat. No. 5,435,169 (the "'169 patent"), presented a device and method for the continuous, near real-time, monitoring of low level concentration of VOCs in a fluid stream. The method is comprised of the steps of collecting at least one sample of the VOCs from the fluid stream followed by concentrating the collected VOC samples. At predetermined time periods, the concentrated, collected samples of the VOCs are desorbed from the concentration means, and the desorbed, concentrated, collected samples of the VOCs are injected into a detector. The steps are repeated for continuous monitoring.

The device in the '169 patent comprises a multiport sampling valve, a concentrator element and a concentration detector. The valve comprises a sample retention element, with the valve periodically switching to cause a sample of the stream, with contained materials, to enter and be retained in the sample retention element. The valve is further connected to a source of an inert carrier gas, wherein the sample is entrained on the carrier gas and is carried to the concentrator element from the sample retention element.

Although the '169 patent addressed many of the inadequacies, (i.e., collecting, transporting and preparing a gas sample for analysis) of the prior art at the time, the technology is not without its own shortcomings. For example, the invention in the '169 patent requires multiple preparative steps (i.e., concentration, desorption, injection) be performed on a gas sample before it can be analyzed. As a result, analysis is not performed in real time but is governed by the number of steps required to prepare the sample for analysis and the time required for each step to be performed. In addition, in order to detect low concentrations of a particular component in a gas sample the invention requires a concentration step, which in turn requires there be a concentration aspect to the invention. Lastly, the carrier gas requirement in '169 results in increased costs, availability and sample reactivity issues.

The ever increasing demand for greater analytical productivity, i.e., in the clinical, agricultural and pharmaceutical industries, has given rise to the development of a variety of automated analytical instruments. The developments in this field have been stimulated by the many advantages gained through automation, e.g., increased precision, decreased cost per sample, and the increased reliability of automated equipment. Generally, automated sample analyzers can be divided into two main groups: batch analyzers and continuous flow analyzers.

In the batch analyzer, each sample is placed in its individual container where it remains during the course of the analytical procedure. The containers proceed through the instrument, where prior to reaching the detector unit, reagents may be added at predetermined points and times. The sample reaches the detector unit, where the actual measuring procedure is performed. Each sample is evaluated separately in the analyzer, i.e., it operates discontinuously. Some of the disadvantages of batch analyzers are that they contain complex moving parts, and the containers must be washed and/or discarded after use. Additionally, these instruments are far less versatile than continuous flow analyzers.

In continuous flow analyzers, samples are successively aspirated from their individual containers into a tube through which the samples move until the entire analysis is completed. In this way, the samples which successively follow each other become part of a continuously moving stream into which, at predetermined points and times, reagents are continuously added at fixed flow rates. The processed stream finally reaches a flow through cell of a spectrophotometer (or other measuring device) where the signal is quantitated. The greatest advantage of continuous flow analyzers is their simplicity and their versatility which allows an easy programming of the stream (which, for instance, might be split for multiple analyses). The disadvantage of the continuous flow concept is primarily the potential possibility of carry-over.

There are two types of continuous flow analyzers, the air segmented flow analyzer and the flow injection analyzer. The former separates successive samples in a continuous tube by means of air bubbles. Flow injection analysis, is based on the formation and exploitation of concentration profiles of samples injected into an unsegmented carrier stream. This procedure allows for considerably greater sampling rates than those typically found in air segmented flow analysis.

The introduction of an air bubble into a flowing stream made the continuous flow analysis practical. The role of the air bubble is simply to segment the flowing stream and thus minimize carry-over effects. Thus, the continuously flowing stream is regularly and frequently segmented by air bubbles which effectively sweep the tubes, thereby allowing the sampling rate to increase dramatically. A further increase of the sampling rate is hindered by the necessity of reaching, for each individual sample, a "steady state" signal level. Consequently, long sampling times are required in order to achieve the necessary precision of analysis, thus limiting the output of the continuous analyzer; increased, rapid sampling rates resulted in carry-over effects and less precision.

Studies of the kinetic parameters which characterize continuous flow systems have established that the attainment of a "steady state" signal level is not required provided that the sample is introduced into the continuously flowing stream over an exact period of time. However, the utilization of such "transient" signals requires a high precision of sampling, which is difficult to achieve. This is due to the difficulties with precise sampling; irregularities in the pumping action of the pump; and the presence of air bubbles.

The "flow injection analysis" system, a second type of continuous flow analyzer, introduces samples directly into a continuously flowing carrier stream. Unlike much of the prior art where the sampling tube continuously introduces material (sample-air-wash-air-sample, etc.) which then joins a flowing stream of reagents, the flow injection analysis is based upon discrete injection of a well defined volume of sample into a continuously flowing stream of reagents, which is then carried towards a detector. The reagents, necessary for a particular analysis, can be added to the system neat, can be present in a carrier stream into which samples are injected, or can be added at positions further down the line on the way to the detector.

Electromagnetic radiation has been used in a wide array of noninvasive diagnostic applications. X-rays have been used for many years to create a two dimensional image of the inside of an object. Computed axial tomography scanners are able to generate three dimensional images from a series of two dimensional x-ray images. Magnetic resonance imaging (also known as nuclear magnetic resonance spectroscopy), such as disclosed in Harms et al., U.S. Pat. No. 5,415,163 A and Rapoport et al., U.S. Pat. No. 4,875,486 A, operate by first applying a magnetic field to a subject so as to align, in a uniform manner, the nuclei of atoms within a portion of the subject to be tested. These aligned nuclei are then briefly exposed to a radio frequency (RF) signal set to a specific frequency, which causes each of the various aligned nuclei at a lower energy state to spin or flip to a higher energy state, known as a resonant frequency. The magnetic field is then removed or altered, causing the nuclei forced to a resonant frequency to become unstable and return to their original lower energy state. This later process is called spin relaxation. The faint energy released from the spin relaxation is then collected as a representation of the nuclei within the sample.

Hence, the spin relaxation energy released by the sample is used to generate an image that is representative of the sample. The RF signal itself is not utilized for detection or imaging purposes—it is only used to excite the nuclei to a higher energy state and is removed before the spin relaxation energy is detected. Further, the magnetic field(s) are only used to align and then release the nuclei in the sample, and are removed or altered before spin relaxation can occur.

While electromagnetic signals transmitted through a specimen have been used to detect or measure the concentration of various chemicals in that specimen, such prior techniques were not highly accurate and results were often difficult to repeat. For example, U.S. Pat. No. 4,679,426 disclosed a non-invasive technique for measuring the concentration of chemicals, such as sodium chloride, in a sample. Periodic electromagnetic waves between 10 MHz and 100 MHz were coupled to a subject's finger and resulting waveforms were found to be indicative, at specific frequencies (i.e., 17.75 MHz for sodium chloride and potassium chloride), of concentration levels of those chemicals in the finger. Likewise, U.S. Pat. No. 4,765,179 used periodic electromagnetic waves between 1 MHz and 1 GHz, that were coupled to a subject's finger, to generate a waveform that provided meaningful analysis of glucose levels in the subject based on the presence of other compounds in the subject's blood at specific frequencies (i.e., 17.75 MHz for sodium chloride and potassium chloride, 11.5 MHz for ethyl alcohol, etc.).

In U.S. Pat. No. 5,508,203 (the "'203 patent"), high frequency electromagnetic radiation was coupled to a specimen through a probe pair to generate a signal of varying amplitude or phase that could be compared to a source signal to determine the presence of a target chemical, such as NaCl, to help determine glucose levels. While this later technique represented an improvement over the prior methods, it was soon realized that electrolytes, e.g., NaCl, KCl, $Na_2HPO_4$, and $KH_2PO_4$ of varying concentrations in human blood, can affect the accuracy of glucose measurements using the '203 patent.

To account for the deficiencies in the '203 patent, a new technique was developed in U.S. Pat. No. 5,792,668 (the "'668 patent"), in which two signals were transmitted through the subject at the same time and the magnitude of impedance at the subject was measured to determine a glucose level in the subject. In particular, the two signals had a cross-over frequency of about 2.5 GHz that provided the best measurement of impedance. In blood specimens, it was found that electrolyte concentration effects are effectively "tuned out" by examining impedance at this cross-over frequency. A similar approach was applied in U.S. Pat. No. 7,184,810 (the "'810 patent"), which cites the '668 patent. In the '810 patent, a probe is applied to the subject's skin, through which electric pulses from a pulse generator are fed and partially reflected back to a measuring device, where a time resolved measurement is made. The glucose level is determined from matching the measured voltage to a calibration table.

The next evolutionary step in the development of electromagnetic energy signals to determine the presence and concentration level of chemicals within a subject is represented in U.S. Pat. No. 6,723,048 B2 (the "'048 patent"), which is assigned to the assignees of the present application and which discloses a noninvasive apparatus for analyzing blood glucose and similar characteristics. The '048 patent apparatus utilizes spaced apart transmission and detection nodes placed on either side of and in contact with a sample to be tested. The nodes are always in close proximity to one or more pairs of magnets that create a magnetic field that envelope the nodes and the sample between the nodes. An RF signal having a frequency between 2 GHz and 3 GHz is transmitted from the transmission node through the sample and to the detection node.

The detected signal is then sent to an analyzer that employs pattern recognition techniques to compare the detected signal at a specific frequency (with respect to glucose, the '048 patent specified 2.48 GHz), to previously detected signals at the same frequency to make a determination regarding the characteristic of the sample being tested. For example, if the sample was a finger of a patient that had previously been tested when the patient was known to have different glucose levels (verified through a more traditional form of glucose testing) to create three or more previously detected signal patterns, the presently detected signal would be compared to each of these previously detected signal patterns to determine which pattern it most closely resembled in order to approximate the patient's present blood glucose level.

In addition to testing glucose levels and other blood chemistries, it has been speculated that electromagnetic frequency spectrum technologies could have application to the biometric identification field, but development is still needed in this area. In many fields of activity, it is essential that persons be identified or their claimed identity be authenticated. Examples of such fields include granting physical access or entry into buildings, rooms or other spaces, airport security, credit card purchasers, ATM users, passport verification, electronic access to information or communication systems, etc.

A number of noninvasive detection technologies have been developed to address these needs, such as fingerprint scans, iris and retina scans, and voice recognition. These technologies operate on the principal that individuals possess unique and unchanging physical characteristics that can be measured and compared with stored data. The basic requirements for acceptable biometric technology are that it must allow for practical widespread use, be accurate and reliable, be difficult or impossible to circumvent, be quick, easy and convenient, present no or little privacy violation concerns, be low cost to produce, and be consumer friendly. Current biometric identification and authentication technologies do not meet all of these basic requirements.

Iris and retina scanning technologies can be highly accurate, but the equipment used in scanning is expensive and requires substantial space. Further, humans are highly uncomfortable with the idea of having their eyes scanned with a laser or infrared light or having their picture taken and stored by a machine (and then used by who knows who). Also, iris and retina scanners have been spoofed with a number of techniques that have required the technologies to be modified in various ways, making the technology more expensive, less convenient, and less consumer friendly.

Electronic or optical fingerprint scanning systems are inexpensive, but are not very accurate, are easily damaged, and can be easily spoofed. Variations in skin, ethnic races with very light fingerprint patterns, people with unusually dry skin, elderly people, people with rough hands, water webbing, abrasions and cuts have all been known to create difficulties for fingerprint systems. Furthermore, many people consider fingerprinting to be an invasion of their privacy because of the heavy use of fingerprinting for law enforcement purposes. Additionally, many fingerprint scanning devices have been easily spoofed with objects as common as gummy candy.

Voice recognition systems tend to be the least accurate of the other biometric identification and authentication technologies. Voices can be readily recorded or mimicked, and allergies, colds and other respiratory issues can readily produce false negatives. Hand geometry and face recognition systems suffer from similar issues. They also tend to require a large amount of space and face recognition systems can be expensive. As with fingerprints, changes in a subject's skin, such as a suntan, a burn or a skin condition, or other changes to a subject's physical appearance can present problems for the system.

BRIEF DESCRIPTION OF THE SEVERAL VIEWS OF THE DRAWING

FIG. 14 is a representation of a ratio matrix of clusters for use in a quantification embodiment;

FIG. 15 is a representation of a preliminary registration table for use in the quantification embodiment of FIG. 14;

DETAILED DESCRIPTION OF THE INVENTION

Figure 1:
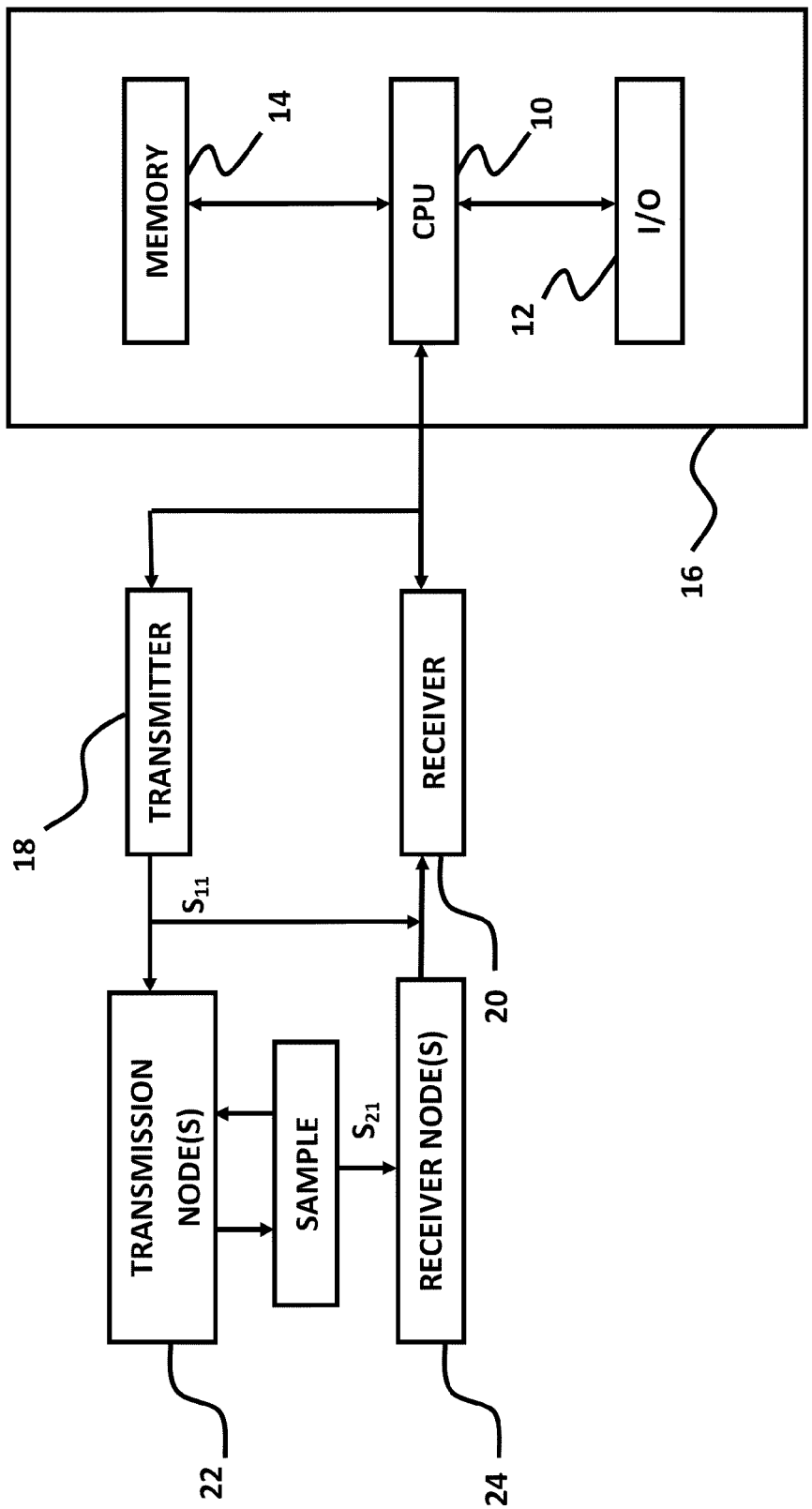
FIG. 1 is a block diagram illustrating the transmission, reception and analysis systems of an embodiment.

An embodiment is related to noninvasive systems and methods for scanning and analyzing one or more characteristics of a sample, including living and inert objects, utilizing electromagnetic radiation. In particular, an embodiment utilizes a large spectrum of electromagnetic radiation that is transmitted through a sample to a receiver that creates a series of spectral data sets that are then developed into a composite spectrogram by an analyzer and processed to determine the one or more characteristics of the sample. A magnetic field can alternatively be applied around the transmitter, receiver and sample to enhance some characteristic analysis applications and to make other characteristic analysis applications possible. With respect to humans, the sample is usually a finger or some other part of the body that can be inserted into or placed on a scanning apparatus for scanning purposes. Solids, liquids and gasses can all be measured using the same basic scanning apparatus and different types of delivery and control systems.

While a characteristic can be the sample's possession of some substance, feature, level, percentage, sui generis identity, etc., a characteristic could also be a class, species, genre or category. In other words, a characteristic could be almost anything. The characteristics that can be tested or scanned for in humans and many other living samples include naturally occurring components of the blood, such as blood glucose levels, hemoglobin, cholesterol levels, proteins, red and white blood cell counts, lipids, C-reactive proteins, calcifications and hormone levels, as well as introduced components, such as steroids, pathogens, viruses, bacteria, yeasts and heavy metals, as well as many other biological markers, agents and substances, including biometric identifying markers and controlled substances such as illegal drugs, alcohol and poisons (all identified as "biometric markers" herein). For agricultural inspection purposes, meat and produce can be tested for characteristics indicating bacterial and other forms of contamination. In food processing operations, food products can be tested to regulate mixtures or the quantity of ingredients present, as well as to detect the presence of foreign elements such as metal, blood, nuts, milk and other allergens.

In security applications, unknown substances can be tested to determine their identity, such as illegal drugs, prescription drugs, explosives, poisons and bacterial agents (e.g., anthrax, nerve agents, etc.). Similarly, environmental substances can be scanned and identified in a wide variety of other applications, including biohazard and hazardous material situations, analysis of drinking water for pollutants, contaminants, minerals, and bacteria, and the analysis of air, water and ground (e.g., dirt, minerals, etc.) samples for similar substances. In manufacturing operations, materials can be tested to regulate or control the mixtures of substances, such as plastic, synthetics and petroleum, and the exhaust or byproducts of manufacturing operations can be analyzed to alert an operator of various different conditions, such as a malfunction.

Liquids can be identified for many different purposes, such as in airport security, stadium security or other security operations, or even authenticity, i.e., scanning a bottle of corked wine or sealed liquor to determine its identity, its condition or possibly even its age. Conversely, many substances and combinations of substances, such as certain liquids, can be tested to confirm whether they are what they are claimed to be. For example, when an airport traveler claims a clear liquid to be water, the liquid can be tested to determine whether it is water, and if it is not, the liquid and/or the traveler could be held for further investigation. Likewise, the authenticity of many other objects, such as money, bonds, antiques, documents, etc., can also be verified.

Referring now to FIG. 1, an embodiment and its many applications will be described in greater detail. FIG. 1 is a block diagram illustrating the transmission, reception and analysis systems of an embodiment. The CPU 10, I/O 12 and memory 14 can be configured as standalone components when utilized in some applications or incorporated into a larger computer system 16 for use in other applications. For example, some scanning applications may require an embodiment to be contained within a small, handheld, battery-powered unit that performs a limited application and only requires minimal processing, memory and data handling capabilities (See FIG. 6 for an example of such a device), while other applications may enable computer 16, incorporating the CPU 10, I/O 12 and memory 14, to be located away from the sample, thereby making many more applications possible.

Either the CPU 10 or the computer 16 is further connected to a transmitter 18 and a receiver 20, either directly as shown in FIG. 1 or through the I/O 12. The transmitter 18 is preferably capable of generating electromagnetic radiation across a broad spectrum. While many applications only require a frequency sweep between about 1 MHz to about 20 GHz, additional information about a sample and its characteristics can be achieved utilizing frequency sweeps in ranges from as low as about 9 kHz, or lower, and as high as about 810 THz, or higher.

When the frequencies for a particular sweep enter the visible, infrared or other portions of the spectrum, different or additional transmission nodes and other equipment, as described further below, would be required in order to transmit such signals. Naturally, the receiver 20 must also be capable of operating in the same frequency ranges as the transmitter 18.

The type and arrangement of the nodes would also be impacted by the object being scanned. For example, while it might be possible to utilize an infrared transmitter and receiver placed on either side of a liquid or gaseous object, a more solid or opaque object might block the transmitted infrared signal from being detected by the receiver node. In such a case, it might be necessary to have the transmission node also operate as the receiver node, or to place the transmission node and the receiver node on the same side of the object, such that a deflected signal could be detected. Alternatively, a lower harmonic of the visible light signal could be utilized in place of the visible light signal. For example, if it were known that an element or characteristic of a gas or liquid could be detected using a visible light signal, that same element or characteristic should be detectable at a lower harmonic of the visible light signal, even though the distinguishing features of the element or characteristic would have a substantially lower magnitude and might be difficult to perceive in the lower harmonic signal.

As illustrated in FIG. 1, one or more transmission nodes 22 are connected to the transmitter 18 and used to transmit the electromagnetic radiation and one or more receiver nodes 24 are connected to the receiver to receive the electromagnetic radiation once it has been transmitted through or reflected by the sample, or reflected by the node itself. One embodiment of the invention provides antenna components that can be utilized for both the transmission node and receiver node, but at higher frequency levels, non-antenna transmit/receive components may be required.

Figure 2:
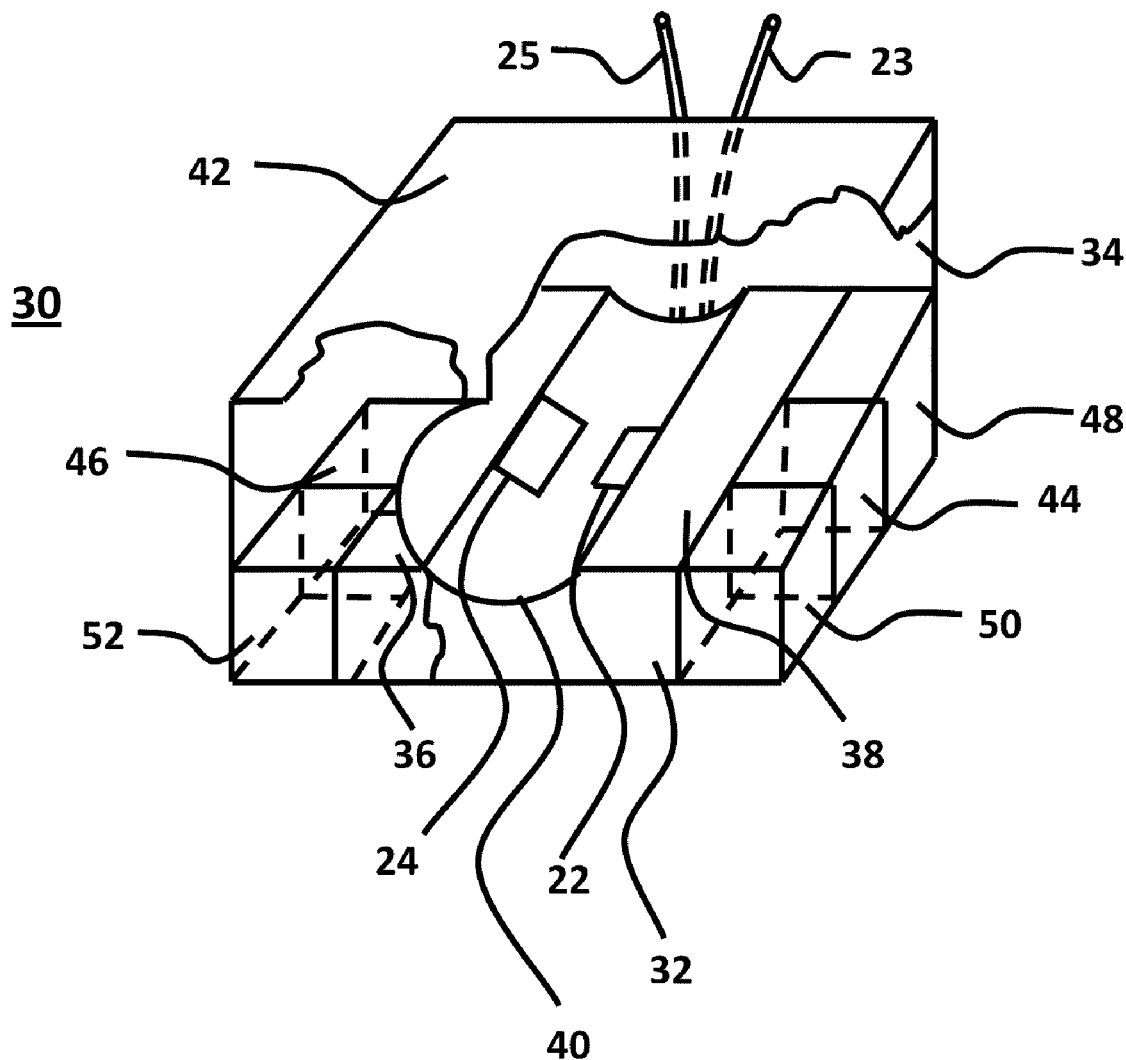
FIG. 2 is a partially cut-away, perspective view with hidden lines of the sample scanning apparatus of an embodiment.

One possible configuration of the transmission nodes 22 and the receiver nodes 24 is illustrated in FIG. 2, which provides a partially cut-away perspective view, with hidden lines, of a sample scanning apparatus 30 in conformity with an embodiment. The sample module and scanning module or apparatus illustrated in FIG. 2 is designed for scanning applications where the sample to be tested, such as a finger of a human, or similarly shaped object such as a test tube or sample container, is placed inside the scanning apparatus 30. The base or bed 32 of the scanning apparatus is shaped in such a way that a finger or object placed within the scanning apparatus 30 will be held in a consistent position. Additional guides or stops can be arranged inside and outside the scanning apparatus to ensure constancy of placement of the sample. For example, as illustrated in FIG. 2, the back wall 34 of the scanning apparatus 30 acts as a stop for the finger or object placed inside. The bed 32 is comprised of a left arm 36 and a right arm 38 with an angled or rounded central guide wall 40 formed there between. The rounded shape of the guide wall 40, in this particular application, helps to further ensure consistent placement of an inserted finger or similarly rounded object.

The bed 32 is formed from a material that has a low dielectric constant $D_k$ (as close to 1 as possible), such as a cross-linked polystyrene, like REXOLITE 1422 (a trademark of C-Lec Plastics Inc.). In such materials the change in $D_k$ is negligible with temperature fluctuations. Although REXOLITE 1422 is presently used, other materials could also be utilized and even some materials with higher dielectric constants or other properties not present in REXOLITE 1422 could enhance some applications. REXOLITE 1422 is a thermoset, rigid and translucent plastic with a dielectric constant of 2.53 (up to 500 GHz) and an extremely low dissipation factor. The performance characteristics of the REXOLITE 1422 bed 32 enables the transmission node 22 and the receiver node 24 to be placed or embedded directly in the bed 32. The nodes 22 and 24 are spaced apart so as to enable a finger or object to be placed between the two nodes, such that any signal transmitted from the transmission node 22 would go through the finger or object to reach the receiver node 24. Highly shielded transmission lead 23 connects the transmission node 22 to the transmitter 18 and highly shielded receiver lead 25 connects the receiver node 24 to the receiver 20.

The shape and arrangement of the nodes 22 and 24 are application specific. As illustrated in FIG. 2, the arrangement of the nodes 22 and 24 and the other components of the scanning apparatus 30 are utilized for biometric testing, glucose level testing and similar types of applications. This same arrangement can be utilized to identify an unknown fluid contained within a test tube or sample container, but a different configuration of the sensor, as illustrated below, may be desirable for such applications.

Still, other applications might require different types of nodes 22 and 24, as well as other equipment, which might need to be arranged differently, to achieve the best results. For example, at high frequencies, such as 810 THz, many changes would be required of the scanning equipment, not just the nodes. For example, in the scanning device illustrated in FIG. 2, the transmission lead 23 and the receiver lead 25 presently utilize 50 ohm cables to carry power to the nodes. The reactive impedance from the nodes to the ground plane of the scanning apparatus 30 (not shown) through the base 32 has been minimized to about 50 ohms at 12 GHz. This impedance is determined by the capacitance of area and spacing of the nodes to the ground plane and the dielectric constant of the REXOLITE 1422 base 32. Since reactive impedance varies as 1/frequency, at higher frequencies, very little power could be transmitted through such leads. Hence, at higher frequencies, very different equipment will be required to make the scanner operate effectively.

Figure 3:
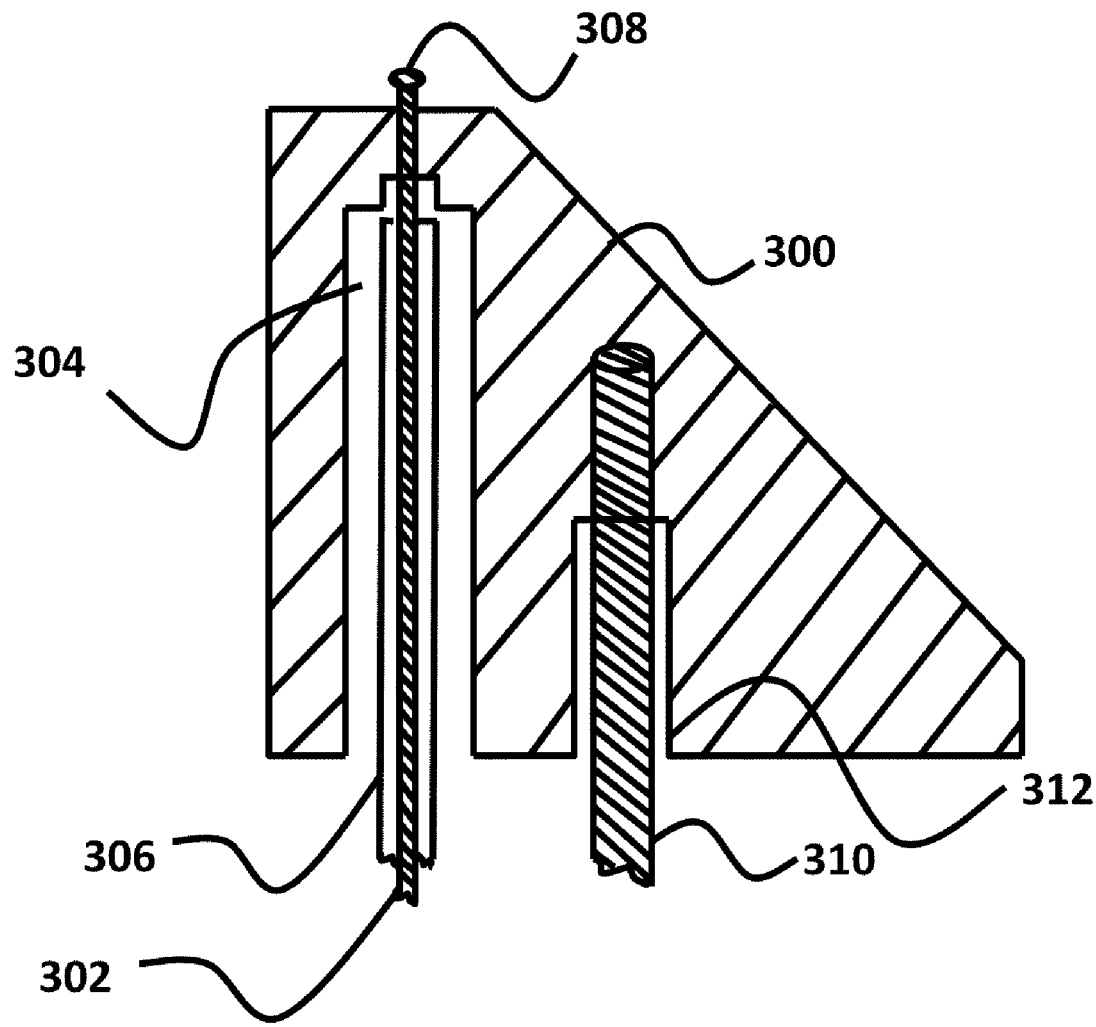
FIG. 3 is a cross-sectional view of either a transmission node or a receiver node of an embodiment.

The shape, orientation and material composition of the nodes can also improve the performance characteristics of the scanning apparatus 30. An embodiment of shape and material composition of either of the nodes 22 and 24 is further illustrated in FIG. 3, which is a partially broken, cross-sectional view of either a transmission node or a receiver node. As shown in FIG. 3, the node is comprised of a metal base 300, such as solid brass with gold plating, although other nonreactive or low reactive metals or alloys could be utilized for the plating. The antenna 302 for the node is inserted into the base 300 through an opening 304 formed in the base 300. A polytetrafluoroethylene sleeve 306, or a sleeve formed from other similar substances, fits around the antenna 302 until the antenna 302 enters a narrowed or tapered portion of the opening 304 near the top of the base 300.

To secure the antenna 302 to the base 300 and to provide an electrical connection between the antenna and the base 300, the top 308 of the antenna 302 is prick punched and affixed with a silver epoxy, although many other manners of securing and connecting the antenna 302 could be utilized. To affix or secure the base 300 to the bed 32, a REXOLITE 1422 screw or post 310 is inserted into a second opening 312 formed in the base 300, which screw or post 310 is in turn affixed or secured to the base 32.

The orientation and location of the nodes 22 and 24, relative to one another and/or to a finger or object to be analyzed, can also affect the performance of the scanning device. As illustrated in FIG. 2, nodes 22 and 24 are arranged and oriented within the bed 32 so as to enable the majority of most human index fingers to rest within the bed while making contact with both nodes 22 and 24. Likewise, an object to be analyzed could be shaped or placed within a container, such as a specially shaped container formed from a material such as REXOLITE 1422 that would enable the object to rest within the bed 32 in contact (perhaps through the container) with both nodes 22 and 24. In some applications, contact between the finger or object to be analyzed and both nodes 22 and 24 is not necessary to enable detection of an adequate signal at the receiver node 24, but in other applications such contact can make a significant signal quality difference.

Although FIG. 2 illustrates an embodiment with a single transmission node 22 and a single receiver node 24, which enable the creation of spectral data sets for analysis by the CPU 10, additional nodes can be utilized to create additional spectral data sets for additional analysis. For each N number of transmission nodes 22 and M number of receiver nodes 24, a total of at least N×M, or likely many more, spectral data sets become possible. The nodes 22 and 24 can also be arranged in arrays of two or more nodes to create further spectral data sets for analysis. As used herein, the terms "spectral data set" or "spectral data sets" refer to any spectra collected at a particular frequency or sample point, even if there is only a single spectrum at any such frequency or sample point. Further, as used herein, the term "composite spectrogram" refers to any collection of spectral data sets into a data file, regardless of whether that data file is then used to generate an image of the combined spectral data sets within the data file or is processed in its raw form by one or more algorithms to generate an output based on the combination of spectral data sets.

As further illustrated in FIG. 2, the bed 32 (including the nodes 22 and 24) is enclosed within a closed-top housing 42 that provides structural stability for the scanning apparatus 30, provides a clear opening for insertion of the finger or object to be tested, and that provides electrical shielding. The housing 42 could also be open-top, either partially open around the area in which a finger or object to be tested would be placed, or completely open on the top. The housing 42 could be differently shaped as well, as further described below.

A housing 42 composed of a shielding material and providing somewhat less than 360 degree coverage, as illustrated in FIG. 2, would allow for simple insertion of the finger or object, would reduce electrical noise, and would reduce environmental interactions with any magnetic field generated within the housing, as further described below. The housing 42 would also include a base portion (not shown in FIG. 2) below the bed 32, magnets 44 and 46, and blocks 48, 50 and 52, to complete the housing enclosure.

The housing 42 could be formed of REXOLITE 1422 or other materials, such as aluminum or copper. Alternatively, if the housing is to be used to also provide magnetic shielding, the housing 42 could be made somewhat larger to provide a sufficient gap or spacing from the magnets 44 and 46, at least 0.3 inches, and be fabricated from soft iron, mu-metal (a nickel-iron alloy (from about 65% to 85% nickel, from about 5% to 25% iron, plus copper and molybdenum) that has a very high magnetic permeability) or other similar metal of sufficient thickness to prevent saturation of the metal. The housing 42 could also be fabricated to include RF shielding, such as an attunement shield that tunes in or out certain frequencies to deaden or enhance information in the composite spectrograms.

The scanning apparatus 30, as illustrated in FIG. 2, also includes magnets 44 and 46 positioned on the outside of arms 36 and 38 that form a magnetic field around the nodes 22 and 24 and the object to be tested. For some applications of the scanning apparatus 30, the magnetic field created by the magnets 44 and 46 is completely irrelevant and the magnets should not be utilized. In other applications, the magnetic field enhances the analysis of the composite spectrograms, but is not required. In still other applications, such as glucose testing, the magnetic field appears to be required to generate more usable spectral data sets.

When a magnetic field is desirable, high-gauss permanent bar magnets, made of a Neodymium compound ($Nd_2Fe_{14}B$), cylindrically shaped of dimensions of about 1.25 inches long by about ⅝ inches in diameter of 50 MGOe (Mega Gauss Oersted) are used, although other magnets of different compositions, shapes, and strengths and even nonpermanent magnets (created using electromagnetism) could be utilized. The shape, position, strength and number of magnets 44 and 46 utilized is important with respect to configuring the position of the magnetic field relative to the transmission node 22 and receiver node 24 and the sample to be tested, and the intensity of that magnetic field. FIG. 2 illustrates an embodiment with magnets 44 and 46 positioned on the outsides of arms 36 and 38 and held in place on the sides of the magnets 44 and 46 by REXOLITE 1422 blocks, such as block 48 and blocks 50 and 52 illustrated with hidden lines. A block corresponding to block 48 would be positioned next to magnet 46, but is not visible in FIG. 2 due to the presence of the housing 42.

The position of the magnets 44 and 46 as illustrated in FIG. 2, with the north pole of magnet 44 and the south pole of magnet 46 facing the front of the scanning apparatus 30 and the south pole of magnet 44 and the north pole of magnet 46 facing the rear of the scanning apparatus 30, creates a magnetic field that surrounds the nodes 22 and 24 and any portion of the sample to be tested that is positioned between the nodes. As configured, the magnetic field near the rear of the nodes 22 and 24 is near zero and drops to zero about 1 mm from the back of the nodes towards the rear of the scanning apparatus 30. The magnetic field strength near the front of the nodes 22 and 24 and to a position about midway between the nodes is on the order of about 300 gauss. This particular magnet/node configuration is utilized in the scanning device 30, as noted above. Other applications and other scanning apparatuses, however, might achieve better results with different configurations or compositions of magnets and nodes, such as illustrated in FIGS. 4A-4H.

Figure 4A:
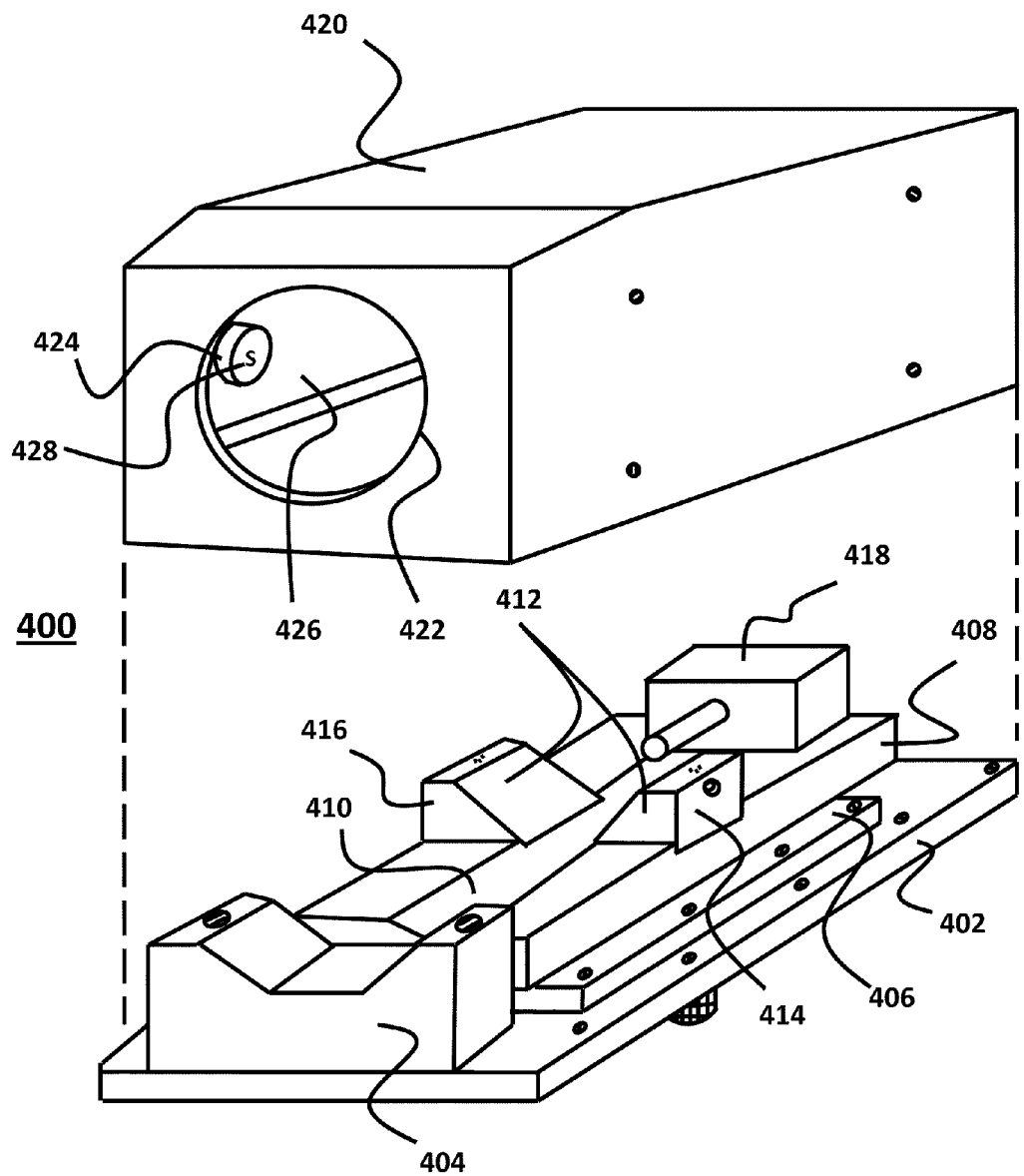
FIG. 4A is a partially exploded, perspective view of an embodiment including one pair of nodes and two pairs of magnets.

FIG. 4A is a partially exploded, perspective view of an alternative embodiment of the scanning apparatus illustrated in FIG. 2. The scanning apparatus 400 of FIG. 4A is comprised of one set of nodes and two sets of magnets. A base 402 supports a finger guide 404, made of REXOLITE 1422 or a similar material, and a riser plate 406. Riser plate 406, which is formed of a brass material and which operates as the RF ground return, supports a bed 408 with a central trough 410 and a first node set 412 comprised of a transmission node 414 and a receiver node 416. The bed 408 also supports a stop 418, which operates in conjunction with the shape of the finger guide 404, the trough 410 of the bed 408, and the first node set 412 to position a finger, sample or object in the correct position and orientation within the scanning apparatus 400.

A housing 420 fits over the top of the base 402 to complete the enclosure and to provide a magnetic field through the nodes and sample in addition to RF and/or magnetic shielding, when needed. Housing 420 also forms an opening 422 through which a finger, sample or object could be inserted. The housing 420 also supports two sets of magnets that are affixed to the opposite inner sides of the housing. Only magnet 424, of a first set of magnets, is illustrated in FIG. 4A, affixed to the left inside wall 426 of the housing 420, with the south pole 428 of magnet 424 facing the inside of the scanning apparatus 400. Another magnet, with its north pole facing inward would be positioned on the right inside wall of the housing 420 opposite magnet 424. Likewise, a second set of magnets, not shown, would be similarly affixed to the inside walls of the rear of housing 420, facing in opposite directions and with their poles reversed in comparison to the first set, i.e., the magnet on the same side of the housing 420 as magnet 424 would have its north pole facing the inside of the scanning apparatus 400.

Figure 4B:
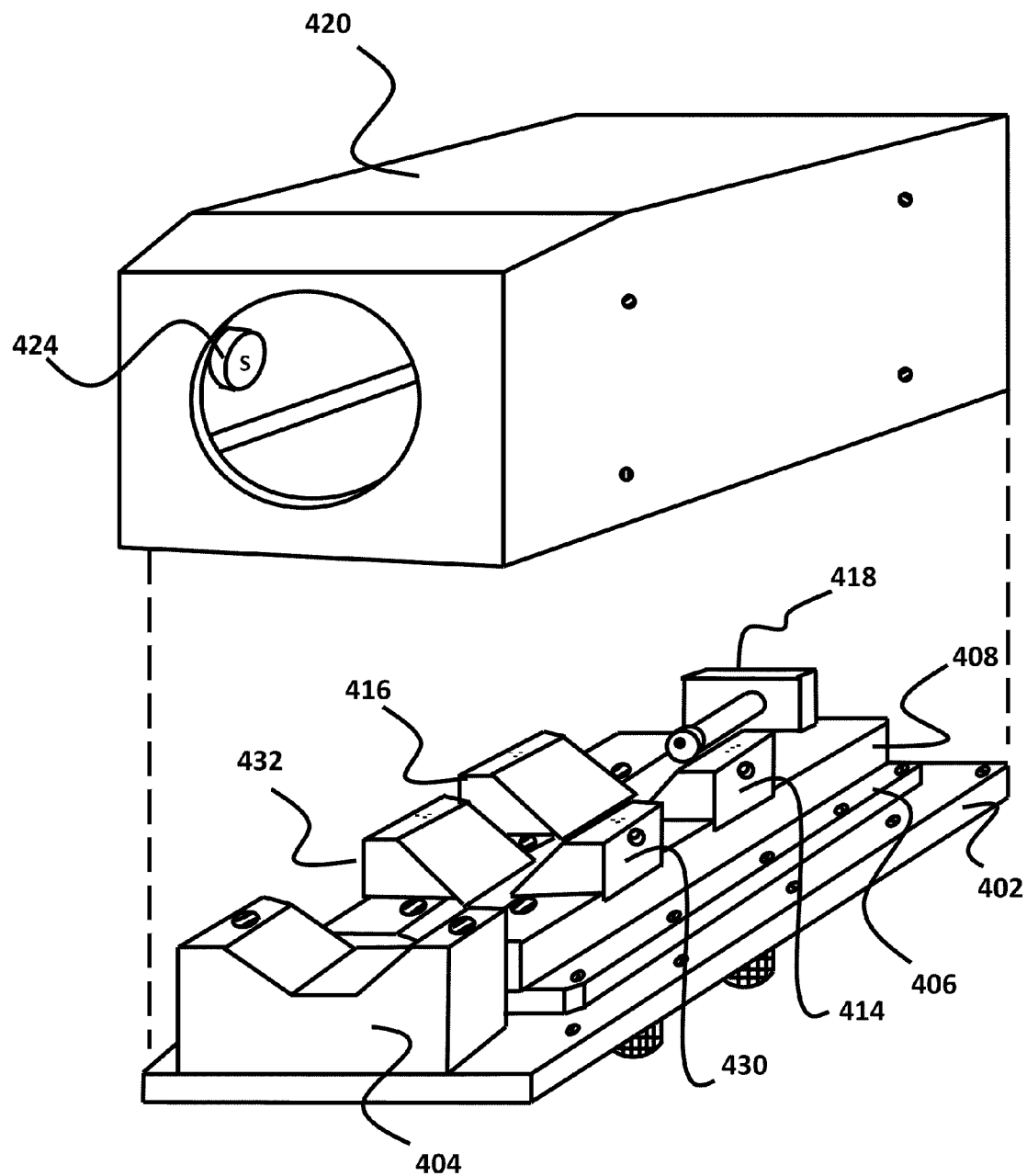
FIG. 4B is a partially exploded, perspective view of an embodiment including two pairs of nodes and two pairs of magnets.

FIG. 4B is almost identical to FIG. 4A, but includes a second node set comprised of a second transmission node 430 and a second receiver node 432. With respect to both FIGS. 4A and 4B, the base 402 is about 2.20 inches wide, about 3.20 inches deep and about 0.10 inches thick. The housing 420 is about 1.67 inches tall at the front. All of the remaining parts of the scanning apparatus 400 are scaled accordingly. The scanning apparatus 30 of FIG. 2 is similarly sized. Of course, other sizes and configurations are possible and might be preferred for different scanning operations. Accordingly, an embodiment anticipates many other possible sizes and configurations and is not limited by the sizes and configurations illustrated herein.

Figure 4C:
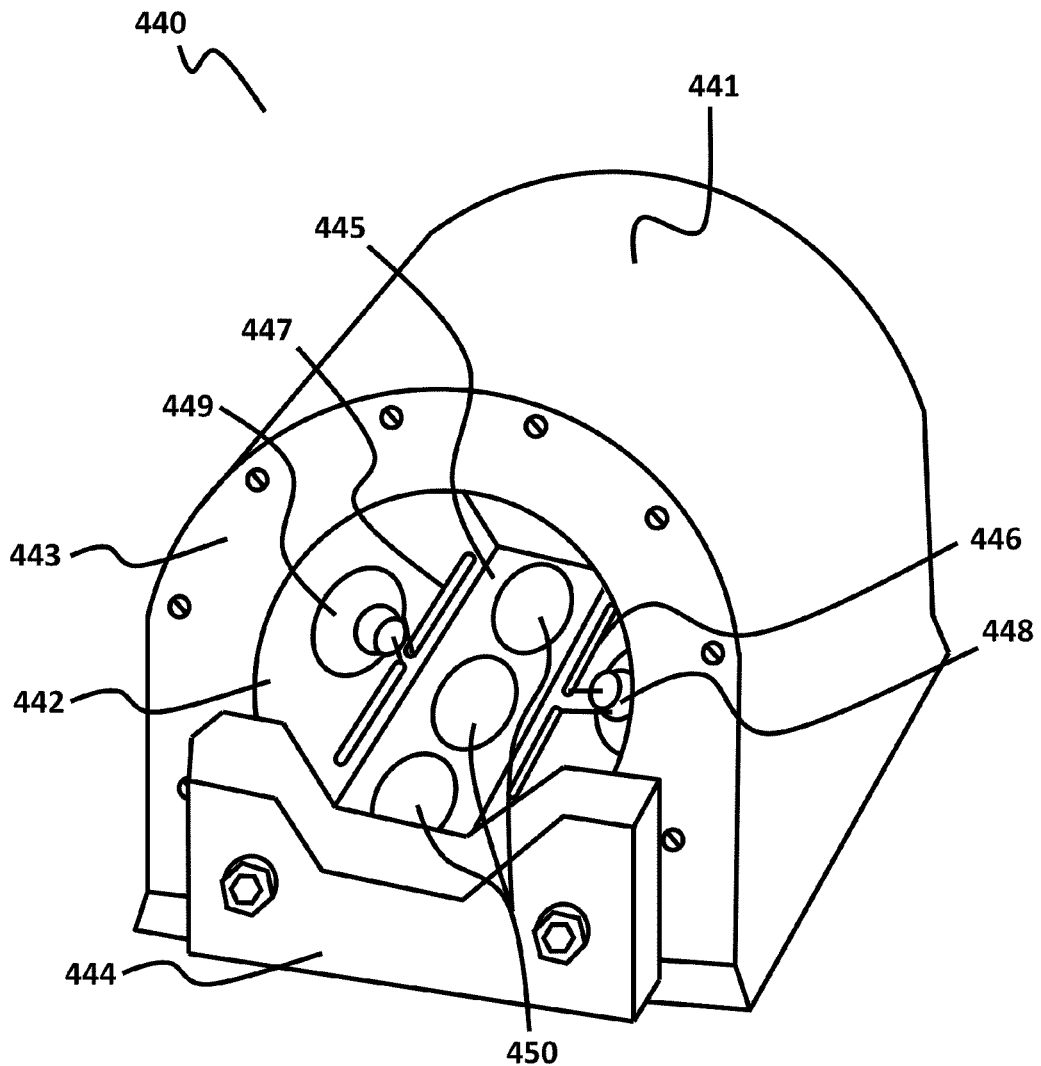
FIG. 4C is a perspective view of an embodiment of a scanning apparatus.

FIG. 4C illustrates another alternative embodiment of the scanning apparatus illustrated in FIG. 2. The scanning apparatus 440 of FIG. 4C has at least an upper portion that is cylindrically shaped. The base of the scanning apparatus may have a rectangular base, allowing the scanning apparatus to stand and be stable on a flat surface. The scanning apparatus consists of a cylindrical housing 441 to provide enclosure and to provide a magnetic field around the nodes and the sample in addition to RF and/or magnetic shielding, when needed. Housing 441 also forms a finger opening 442 in the front and a second opening (not shown) in the rear of the apparatus. The housing 441 and the base (not shown) of the scanning apparatus 440 are held firmly in place by a first face plate 443 and a second face plate 452 on the opposite end (shown in FIG. 4D). The first face plate 443 and the second face plate 452 can be attached to the housing 441 and the base with one or more screws, by welding, or other suitable methods well known in the art.

The first face plate 443 can be part of the magnetic shield contained in the housing 441. The first face plate 443 and the second face plate 452 may have rectangular bottoms, further allowing the scanning apparatus 440 to stand firmly. A finger guide 444 is attached to the first face plate 443. The finger guide 444 can be made of a material with a low dielectric constant, such as REXOLITE 1422. A base or bed 445 of the scanning apparatus is shaped in such a way that a finger or object placed within the scanning apparatus will be held in a consistent position. Additional guides or stops can be arranged inside and outside the scanning apparatus to ensure constancy of placement of the sample.

In contrast to the antennas illustrated in FIGS. 2, 3, 4A and 4B, the scanning apparatus 440 of FIG. 4C employs dipole antennas. A first dipole antenna 446, having two electrode halves, and a second dipole antenna 447, having two electrode halves, span along both sides of the inside of the scanning apparatus 440 just above the bed 445. The center conductor of the semi-rigid coaxial RF connector 448 is connected (via soldering or similar means) to the back half of the dipole electrode 446, while the metal shield of the coaxial RF connector 448 is connected to the front half of dipole electrode 446. On the opposite side, the center conductor of coaxial RF connector 449 is connected to the front half of the dipole electrode 447 and the metal shield of the coaxial RF connector 449 is connected to the rear half of the dipole electrode 447. The coaxial RF connectors 448 and 449 are then routed within the scanning apparatus 440 to the rear of the unit.

A first set of magnets 450 are placed below and along the length of the base 445. A second set of magnets (not shown) are placed on the inside of the top of the housing 441, directly opposite the first set of magnets 450. The first set of magnets 450 consists of three magnets, with the north pole of the magnets facing up. The second set of magnets is aligned with the corresponding first set of magnets 450, with the south pole of the second set of magnets facing down. The first set of magnets 450 can also have the south pole of the magnets facing up, with the second set of magnets having the north pole of the magnets facing down. A different number of magnets can be used to obtain various behavior performances of the scanning apparatus 440. For example, two magnets can be used for the first set of magnets and two magnets can be used for the second set of magnets, etc. In an embodiment, the first set of magnets would cover the entire base 445. In another embodiment, the first set of magnets would cover only a fraction of the base 445. The shape of the magnets can also be varied. The magnets used can be round shaped, oval shaped, or pellet shaped. By having the magnets placed along the base, instead of along one of the side walls as illustrated in FIGS. 2 and 3, it results in the magnetic field being perpendicular to the electric field, the electric field generated by the signals being transmitted from the transmitter nodes to the receiver nodes. Such arrangement improves the amount of energy absorbed by the tested sample, and consequently improves the accuracy of the resulting readings. As previously noted, magnets may not always be necessary.

In an embodiment of the scanning apparatus 440, the first dipole antenna 446 and the second dipole antenna 447 are in direct contact with the sample placed within the scanning apparatus 440. In an embodiment, the dipole antennas 446 and 447 may be shielded in some manner from the sample placed within the scanning apparatus 440, to prevent the dipole antennas from coming in direct contact with the finger or object. For example, the dipole antennas 446 and 447 may be placed further up on the side walls of the scanning apparatus 440 instead of being placed in closer proximity to the bed 445 or next to the bed 445. The dipole antennas 446 and 447 may also be shielded with a material with a low dielectric constant, such as REXOLITE 1422.

Figure 4D:
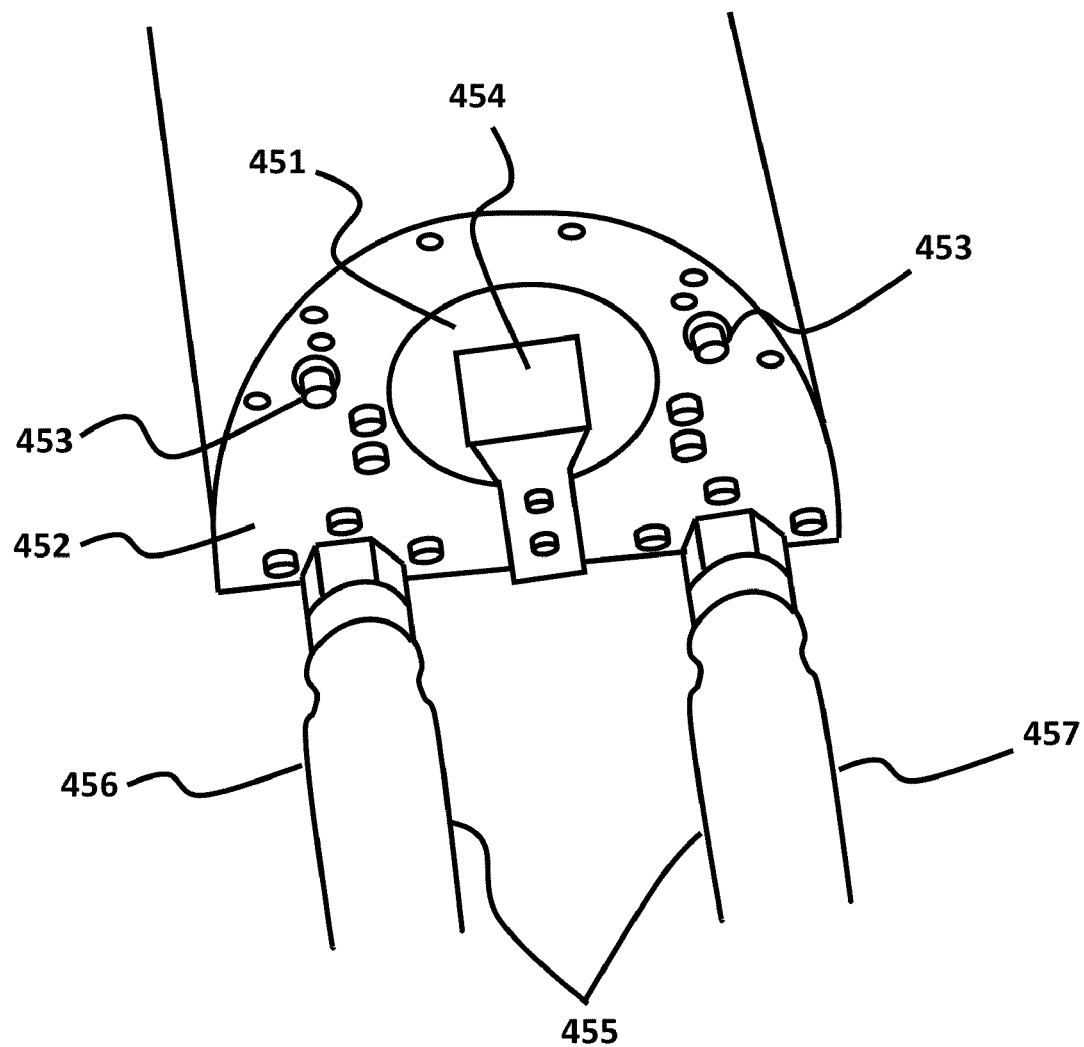
FIG. 4D is a perspective view of the rear of the scanning apparatus of FIG. 4C.
Figure 4E:
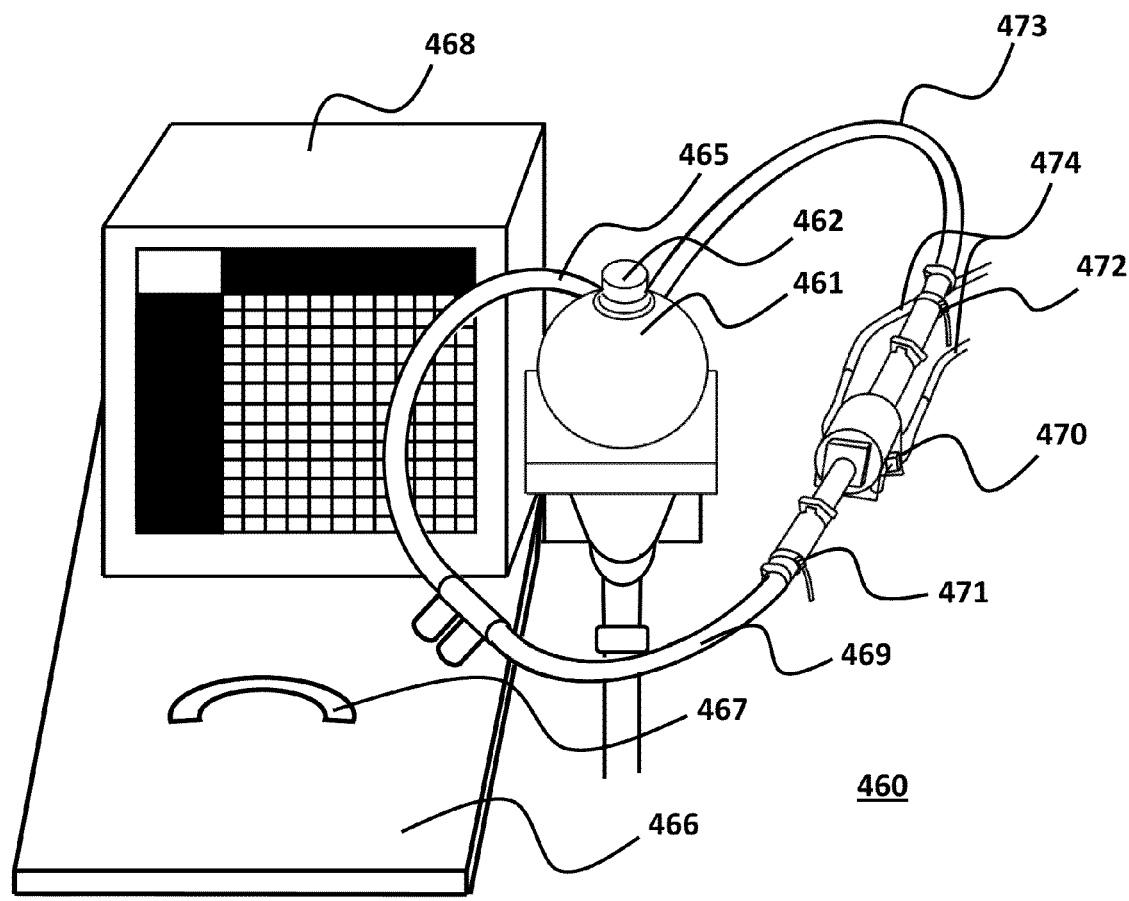
FIG. 4E is a perspective view of an embodiment of a flow through sensor.
Figure 4F:
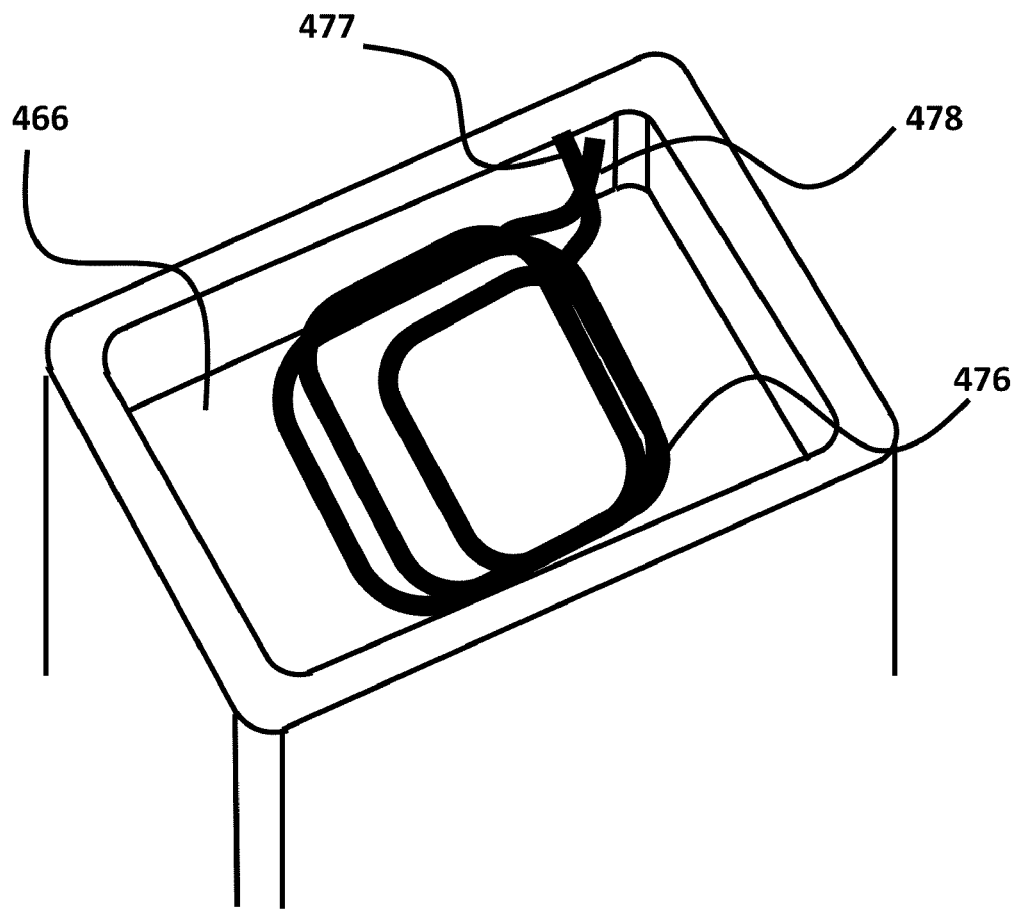
FIG. 4F is a perspective view of an embodiment of the temperature control unit of the flow through sensor of FIG. 4E.
Figure 4G:
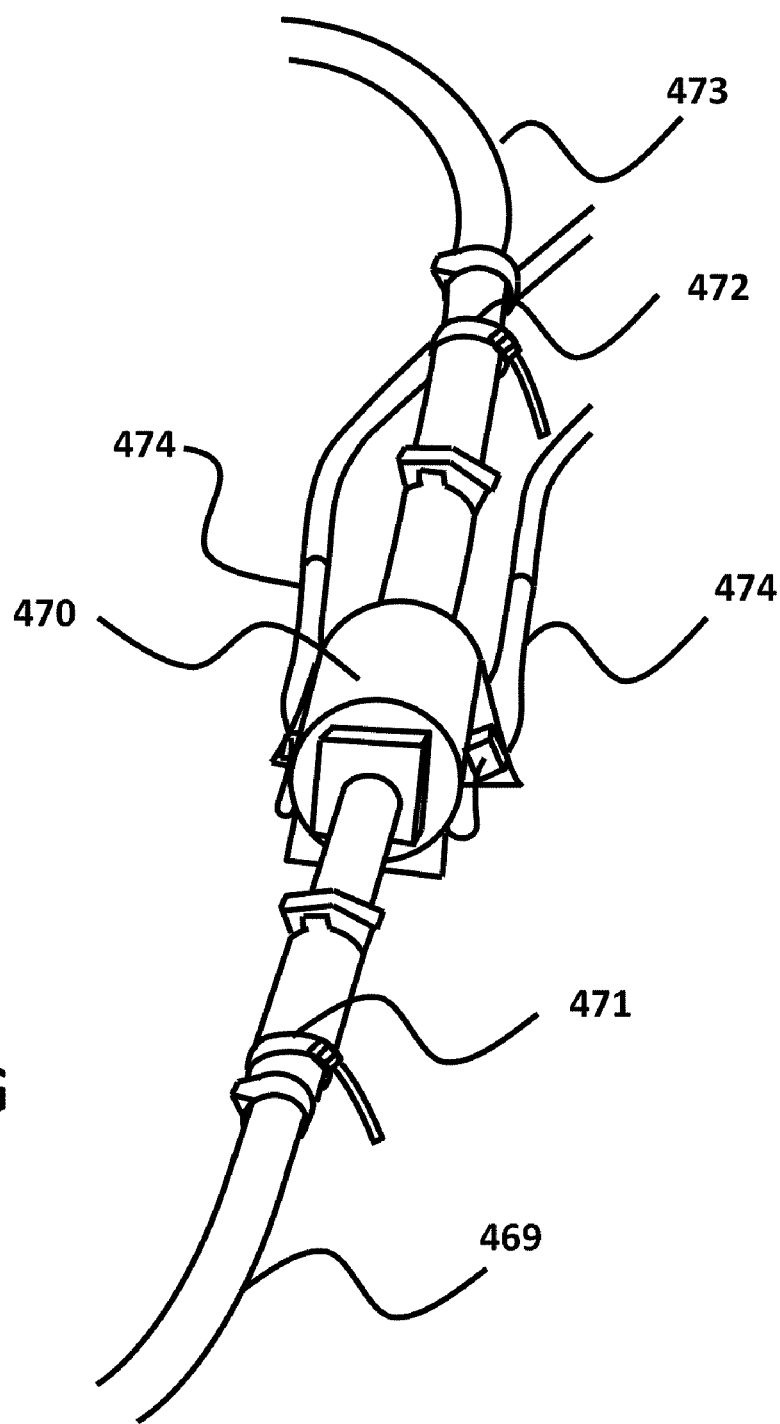
FIG. 4G is a more detailed perspective view of an embodiment of a scanning apparatus for use in the flow through sensor of FIG. 4E.
Figure 4H:
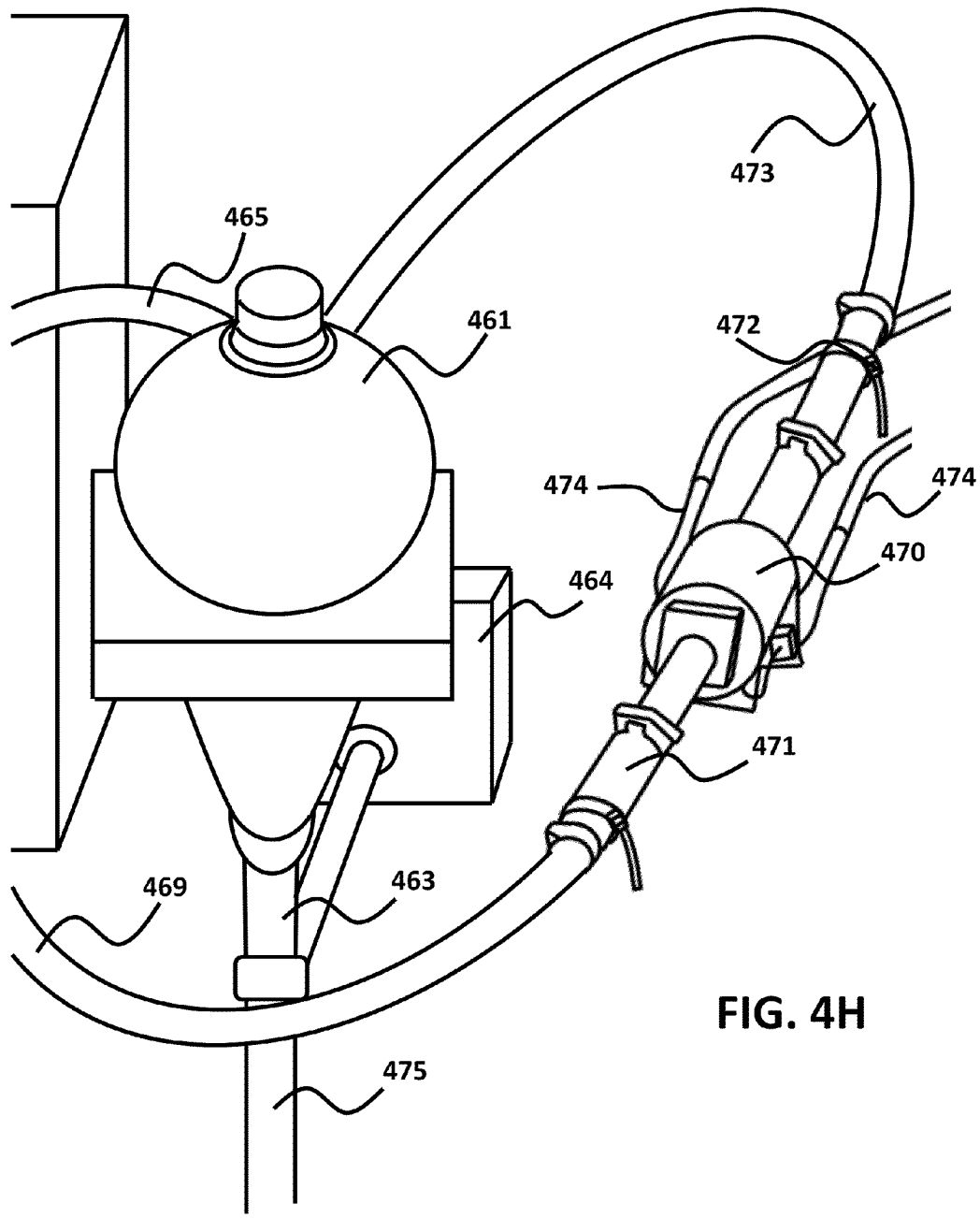
FIG. 4H is a more detailed perspective view of the flow through sensor of FIG. 4E.

FIG. 4D shows the back of the scanning apparatus 440. The second opening 451 allows for a tube to be passed through the scanning apparatus 440 when in use with the flow through sensor, further discussed herein. Alternatively, the scanning apparatus 440 without the second opening 451 can be used if testing samples without the need for the flow through sensor. A second face plate 452 is attached to the scanning device. One or more screws 453 can be used to anchor the base 445 and to keep the base 445 from moving. The screws 453 can be made of plastic or from a material with a low dielectric constant. A finger stop 454 allows for a finger or object to be inserted through the first opening 442 up to the point where the finger comes in contact with finger stop 454 on the inside of the scanning apparatus 440. The finger stop 454 is substantially T-shaped; however, any other shape that serves as a stopper indicator can be used to provide consistent positioning within the scanning apparatus 440. The finger stop 454 can be a removable piece, allowing for use of the scanning apparatus 440 with the flow through sensor described below. The finger stop 454, while described as a stop guide for fingers, also serves the same purpose with other objects. For example, if a liquid sample was being tested, the liquid sample could be placed in a test tube, with the finger stop 454 used for informing users how far to insert the test tube into the scanning apparatus 440. In an embodiment, the finger stop 454 could move along a horizontal axis, allowing for the finger stop 454 to be moved further inside of the scanning apparatus 440. This would allow for the finger stop 454 to be adjusted based on the size of the sample being inserted into the scanning apparatus 440.

In an embodiment, the finger stop 454 can be circular shaped and completely shield the second opening 451. This finger stop 454 could also be a removable piece. The finger stop 454 can also have a rectangular shape, or any other shape which completely shields the second opening 451.

A set of RF connections 455 connect the dipole antennas with the transmitter 18 and receiver 20. The dipole antennas can transmit and receive data. For example, a first RF connection 456 can connect the first dipole antenna 446 with the transmitter 18 and a second RF connection 457 can connect the second dipole antenna 447 with the receiver 20. A commercially available network analyzer (not shown) could be used to perform the functions of the transmitter 18 and receiver 20. Two sets of semi-rigid coaxial cables (not shown) within the scanning apparatus 440 connect the first dipole antenna 446 and the second dipole antenna 447 with the RF connections 455, respectively. By removing the second face plate 452 and the screws 453 (along with other screws that are not shown), it is possible to remove the internal portion of the scanning apparatus 440 holding the dipole antennas 446 and 447, along with the semi-rigid coaxial cables and their RF connectors 448 and 449 so the dipole antennas 446 and 447 and other internal components of the scanning apparatus 440 can be modified without having to take the entire apparatus apart.

FIGS. 4E to 4H illustrate an embodiment of the flow through sensor 460. The flow through sensor 460 consists of a mixing tank 461, including a screw cap 462. The test fluid that is being analyzed or identified is added to the mixing tank 461 by removing the screw cap 462 and pouring the liquid into the mixing tank 461. The test fluid added to the mixing tank 461 then circulates via a tube 463 (shown in FIG. 4E, but identified in FIG. 4H) into a pump 464 (shown in FIG. 4H). The pump 464 pumps the test fluid out through the tube 465 into the temperature control unit 466. The temperature control unit 466 may be opened with a lid 467. The temperature control unit 466 can cool or heat the flowing test fluid to a set target temperature specified by a computer controlled controller 468. The controller 468 interfaces with a computer via a wired or a wireless connection to allow the temperature control unit 466 to be managed via program control.

The test fluid circulates out of the temperature control unit 466 through tube 469 into a Pyrex tube (shown, but not separately identified in FIGS. 4E and 4G) with the Pyrex tube carrying the test fluid through the scanning apparatus 470. Any other material alternative to Pyrex which does not interfere with the signals being sent from the transmitter nodes to the receiver nodes can also be utilized, such as REXOLITE 1422 or some similar substance. One or more clamps 471 and 472 can be used to secure the Pyrex tube to the tube 469 carrying the incoming test fluid and the tube 473 carrying the outgoing test fluid. Additional clamps (some shown, but not separately identified in FIGS. 4E and 4G, and some not visible behind the scanning apparatus 470) serve to secure the Pyrex tube relative to the scanning apparatus 470.

The test fluid passes through the scanning apparatus 470 and circulates through the tube 473 back into the mixing tank 461. Measured solute additions can also be added to the liquid in the mixing tank 461 by removing the screw cap 462 in order to calibrate the flow through sensor over a range of solute concentrations. Stirring and dissolving of the solute in the liquid occurs naturally due to the pumping and flowing action and complete dissolution of the solute additions can easily be detected over time by comparison of successive scans taken a few minutes apart. Complete dissolution becomes evident when successive scans become essentially identical.

The scanning apparatus 470 connects to the transmitter 18 and receiver 20 through the connections 474. The test fluid in the mixing tank 461 may be flushed via a tube 475. The length of the Pyrex tube depends on the corresponding size of the scanning apparatus 470. It is important for the Pyrex tube to traverse the entire length of the scanning apparatus 470. The width of the Pyrex tube can be varied depending on the test fluid used or based on alternative settings and the size of the openings in the scanning apparatus for receiving the Pyrex tube. For example, using a smaller Pyrex tube and smaller tubing for the flow through sensor 460 requires the use of less test fluid. For example, if the test fluid was a blood sample, smaller overall tubing and a small Pyrex tube would probably be necessary in order to minimize the amount of test fluid needed to be added to the flow through sensor 460.

As previously noted, split clamps (not specifically identified) serve to immobilize the Pyrex tube within the scanning apparatus 470 and to allow for certain constant conditions within the scanning apparatus 470 associated with movement of the Pyrex tube while the sample is being scanned. Other variations including temperature, humidity, and pressure differences are removed through use of the temperature control unit 466 and the closed loop system, which enable constant conditions. Positioning and repositioning errors and applied pressure (such as pressure applied to the Pyrex tube during a scan) errors are nonexistent. The flow through sensor 460 removes these variables, only allowing for the variation of the test fluid and desired temperature variations. In an embodiment, a dielectric can be placed between the Pyrex tube and the dipole antennas within the scanning apparatus 470.

Stainless steel tubing 476 contained within the temperature control unit 466 circulates the fluid allowing for accurate temperature control of the fluid. The tube 465 connects to one end 477 of the stainless steel tubing 476 and a second end 478 of the stainless steel tubing 476 connects to the outgoing tube 469. This allows for the test fluid to have a constant and precise temperature as it flows through the scanning apparatus 470, thus removing errors due to fluctuations in temperature.

The data collected from the flow through sensor 460 is highly accurate and stable, with low standard deviations in the generated data, due to the controlled environment and the temperature control. In an embodiment, the flow through sensor 460 can be used, with or without the temperature control unit 466, for quality control in industrial settings. For example, fluids or chemicals produced in an industrial setting can be bled off from other equipment, pipes, tubing, etc., to check for quality or in order to identity foreign matter or chemicals by running fluids or chemicals through the flow through sensor 460. The flow through sensor 460 can be scaled accordingly in order to accommodate for a higher throughput. The speed of the flowing fluid running through the flow through sensor can also be varied by adjusting the pump or pumps 464 and the size of the tubing.

The flow through sensor 460 can also be used for testing blood samples, urine samples, and other bodily fluids. As noted above, the size of the tubing used in the flow through sensor 460, as well as the Pyrex or other tube inserted into the scanning apparatus 470, can be adjusted to accommodate for smaller quantities of fluid, such as blood samples. The data collected from blood samples flowing through the scanning apparatus 470 can be analyzed by one or more algorithms that detect various chemicals or substances in the blood samples, as further discussed herein. The flow through sensor 460 can detect properties of samples by analyzing the spectra data sets produced by the scanning apparatus. This is in contrast to bodily fluid tests which detect certain properties or chemicals in bodily fluids by applying foreign chemicals or catalysts and looking for a color change, or some other quantifiable change. The flow through sensor 460 can detect properties of the bodily fluids without applying any foreign chemicals or catalysts to the sample.

While each of the different scanning apparatuses could be used for applications the same as or similar to other scanning apparatuses, the arrangement of different node and magnet sets would create different spectral data sets in each case and would therefore create different useful applications. For example, scanning apparatuses 30 and 440 are particularly well suited for glucose and blood scanning applications in situ, a smaller-sized device might be more desirable for biometric identification. It has been found that even minor changes in the dimensions, angles, materials, shapes and other features of the magnets, nodes and other components of the scanning apparatuses, as well as the position of the sample to be tested, the frequencies used by the scanning apparatuses, the strength of magnets if utilized, the temperature of the sample, the ambient temperature, ambient humidity levels, whether the sample is in contact with the nodes, the volume of the sample, and many other factors can have a small to significant impact on the performance of the scanning apparatuses and the analyzer.

It is therefore necessary to perform a tuning operation with each new configuration of a scanning apparatus and its components, the electronics, and the analyzer in order to get the best results. At the present time, a certain amount of trial and error is required to tune each scanning apparatus for a particular application. For example, in glucose level scanning, the subject's finger should typically be in contact with both nodes and a magnetic field should be used. It may be possible, however, to find a particular arrangement or configuration of the components within the scanning apparatus that will remove the need to have the subject's finger in contact with the nodes, or to use the magnetic field.

In other tests, neither of these requirements may be necessary. For example, in some manufacturing applications where a fluid or gas is being tested for its composition, it may be preferable to insulate the nodes from the fluid or gas, as is done by the Pyrex tube of the flow through sensor 460, so that there would be no contact between the matter being tested and the nodes. In some applications, the magnetic field is not required, but the presence of the magnetic field may substantially enhance the performance of the scanning apparatus.

For many of the applications of the scanning apparatuses, the method of sampling would be similar, but many alternative embodiments would be possible for alternative applications. In a finger scanning application, a direct sample scanning application (where the sample is appropriate to be placed directly into the scanning apparatus), or where the sample can be placed inside a container that can then be placed inside the scanning apparatus, it is preferable to place the finger, sample or container in direct contact with the transmission node and the receiver node. Such direct contact helps to improve or enhance the quality of the signal received by the receiver node after passing through the sample, such as through reduction in the amount of other signals (noise) that can be picked up by the receiver node at the same time and the amount of power loss (reduction in amplitude) in the received signal. In other applications, however, it might be more important to protect the nodes from dirt, oil, and wear and tear by covering them with a thin layer of dielectric material.

Once the sample is in position in or flowing through the scanning apparatus, a series of electromagnetic radiation signals covering a range or sweep of frequencies is transmitted from the transmission node(s) to the sample and to the receiver node(s). The amplitude of these signals can be the same or varied as different applications may require. This series of signals may be comprised of short signal bursts at each of a large number of distinct frequencies ("sample points") with small or large intervals between each frequency selected. In an embodiment a small set of specific frequencies or sample points may be used for specific applications where it is known that spectral data is only needed at those specific frequencies to analyze appropriate characteristics of the sample.

When scanning for glucose or blood sugar levels using the scanning apparatus 30, a frequency sweep between about 100 MHz and about 3 GHz is generally used, but frequency sweeps from about 10 MHz to about 2.7 GHz and about 0.3 MHz to about 20.1 GHz have also been used successfully. For biometric identification scanning, a sweep of about 0.3 MHz to about 20.1 GHz is used due to economics and physical configurations. Alternatively higher frequencies can be used, where utilizing higher frequencies requires a different physical configuration of the scanning apparatuses and requires significantly more computational power to process the resulting spectral data sets and composite spectrograms.

For many applications, the transmitter 18 could be a commercially available signal generator, such as the Agilent Technologies' Agilent E8257D PSG Analog Signal Generator, which is capable (when properly accessorized) of synthesizing signals with high output power (at least 20 milliwatts, based on a constant peak to peak RF voltage of one volt and impedance of 50 ohm) and low phase noise in ranges between about 250 kHz and about 325 GHz. Likewise, the receiver 20 could be a commercially available spectrum analyzer, such as the Agilent Technologies' Agilent ESA E4407B Spectrum Analyzer, which is capable (when properly accessorized) of receiving and analyzing signals in ranges between about 9 kHz and about 325 GHz. A singular network analyzer could be utilized to both generate and receive the necessary signals. More specialized equipment may be required to transmit and receive signals at lower or higher frequencies. Likewise, specific electronic circuitry capable of performing the same types of functions, in place of the signal generator and spectrum analyzer, could be developed for use in an embodiment.

Spectrum generators, analyzers and similar electronic circuitry are commonly used to generate signals and to examine the resulting waveforms. Many such devices allow the user to select the number of sampling points at which signals will be transmitted within a particular frequency range, thereby determining the selected frequencies as well as the intervals between those frequencies. For example, in a frequency range from 100 MHz to 12 GHz, some 3,201 sampling points could be selected (based on the capabilities of the equipment noted above and the compute time required to process that many sample points), although a different number of points could readily be utilized with the same or different equipment and greater computational power. In specially designed circuitry, as noted above, it would be possible to specify the exact frequencies for each sampling point, which might give a user even further flexibility in terms of scanning a sample at the frequencies most likely to generate the most useful information.

The presence of the sample, and in particular the composition of the sample at the particular moments during scanning, modifies the amplitude of at least some of the signals transmitted through or reflected by the sample from the transmission node(s) to the receiver node(s). There are numerous possible explanations as to why the amplitudes of the signals are modified at different frequencies. In many cases, the amplitude is reduced, but in some cases, the amplitude is actually increased. It is possible that amplitude modification might result when electron spins are excited by the electromagnetic radiation, as well as the presence of a magnetic field, when utilized. But electron spin resonance is only believed to occur when a molecule has an unpaired electron, such as a free radical in an organic molecule or a transition metal ion in inorganic complexes, and since most stable molecules have a closed-shell configuration without a suitable unpaired electron, electron spin resonance or similarly electron paramagnetic resonance cannot be the only basis for amplitude modification. Additional amplitude modification could therefore result from proton spins of radiated atomic nuclei, or other phenomena.

It is also possible that additional amplitude modification could result when electromagnetic radiation is absorbed or emitted by molecules associated with a corresponding change in the rotational quantum number of the molecules, otherwise known as rotational spectroscopy or microwave spectroscopy. However, rotational spectroscopy is believed to only really be practical when molecules are in the gas phase where the rotational motion is quantized. In solids or liquids, the rotational motion is usually quenched due to collisions. Dielectric/dipole oscillation or rotation (dielectric spectroscopy or impedance spectroscopy) would also appear to be occurring to some degree, possibly coupled with one or more of the other phenomena noted above.

The amplitude modifications have particular meaning with respect to certain characteristics of each sample that can be determined from careful analysis of the resulting spectral data sets (as described below). This point is particularly important with respect to distinguishing an embodiment from numerous prior art techniques in which a composite signal is employed, but usually only at one or two frequencies are examined, to determine the presence of an analyte. These prior techniques do not look at a composite spectrogram, which represents an amassed congeries of data collected at many different frequencies, in order to perceive subtle quantitative relationships within that composite spectrogram or between compared composite spectrograms.

In all scanning apparatuses, even those with a single node, a single pair of nodes, or multiple transmission and receiver nodes, frequency sweeps could be further varied. For example, a first signal could be transmitted from a first transmission node and only detected by a directly, physically corresponding first receiver node, and then a second signal could be transmitted from a second transmission node and only detected by a second receiver node that directly, physically corresponds to the second transmission node, etc. Since all transmission nodes are also capable of receiving, it is also possible to transmit from one node and receive on all of the nodes, including the transmission node. Thus, it would be possible to transmit from a first node, receive on three other nodes and the first node, transmit on a second node and received on the first node, the second node, and two other nodes, etc.

Alternatively, the first signal could be transmitted from the first transmission node, but only detected by the second receiver node, while the second signal is transmitted from the second transmission node, but only detected by the first receiver node, etc. Additional arrangements of nodes and magnets (if used), including arrays of nodes, could create countless additional variations, including the transmission from a first transmission node and near simultaneous detection by multiple different receiver nodes.

Likewise, although a consistent orientation and position of the sample to be tested has so far been discussed, the position and orientation of the sample could also be varied from test to test or within a single test. For example, a sample could be placed in the scanning apparatus in a first position, then scanning would be performed, then the sample would be rotated by some number of degrees (45°, 60°, 90°, 180°, etc.), and scanning would be performed again. This would result in multiple composite spectrograms that could be used to improve performance or the reliability of identity scanning, etc.

The position of the sample in the scanning apparatus could be further changed by varying the extent of insertion into the scanning apparatus for each test. For example, a finger could be inserted at a first position, where maybe just the finger tip is in contact with a first set of nodes, and then inserted further to a second position, where the first knuckle is in contact with the first set of nodes, etc. In biometric identity scanning applications, position and orientation variations, as well as scanning variations, could be used to increase the distinctive information that is collected regarding the subject. Additional samples, such as a second finger, could also be used to enhance scanning.

Details of the analysis of a scanning application are described with reference to FIG. 5, which illustrates a composite spectrogram signal that is used for glucose level testing in accordance with an embodiment. As disclosed in the '048 patent, the contents of which is incorporated by reference herein, it is known that a change in the magnitude of an RF signal transmitted through a finger occurs at about 2.48 GHz and that this change in magnitude correlates to the concentration of glucose or blood sugar in the finger. However, the '048 patent relied upon basic pattern matching at the specified frequency with previous tests to make a determination about a current test and a subject's current glucose level.

Figure 5:
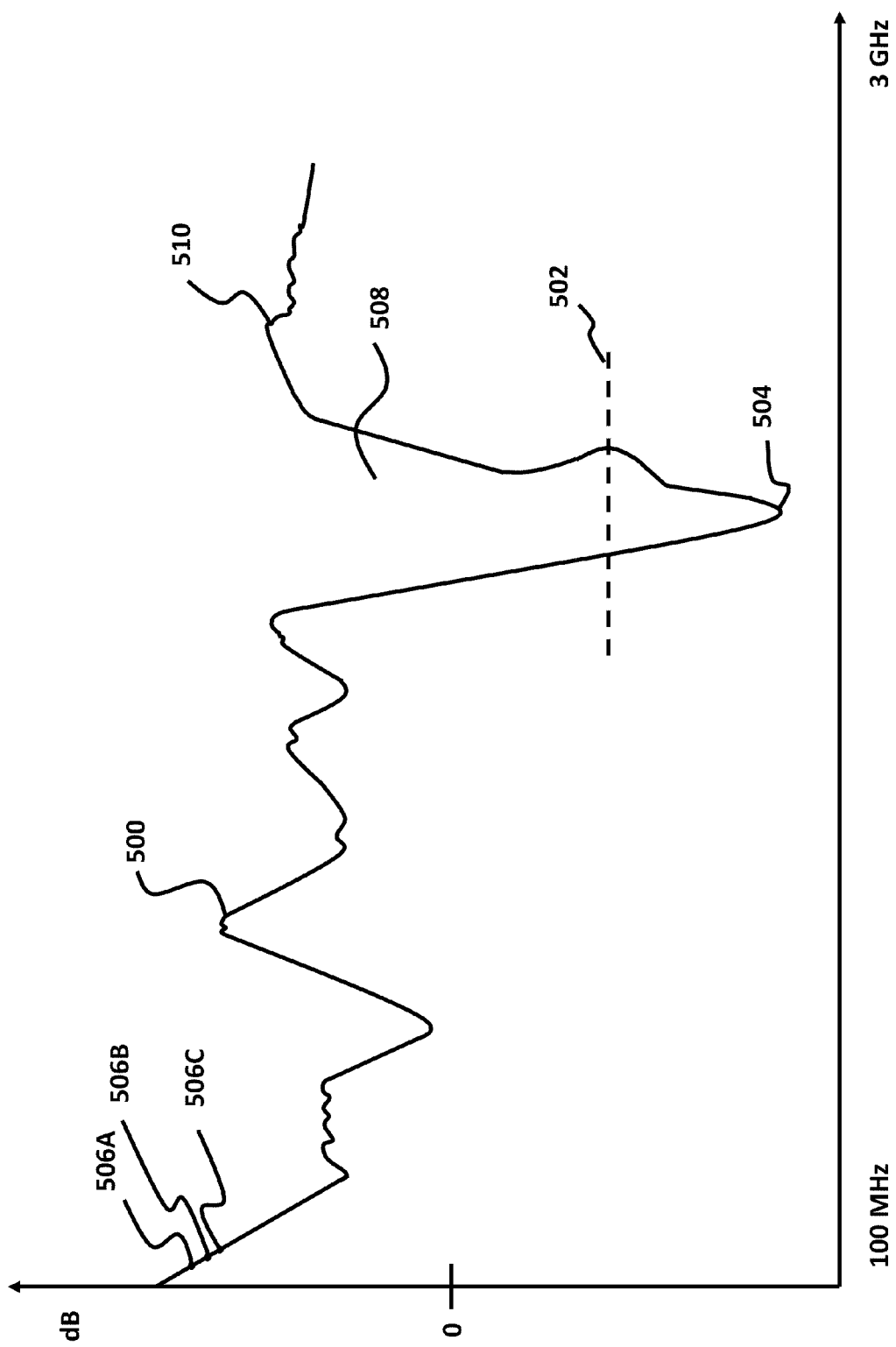
FIG. 5 is an illustration of a composite spectrogram display for glucose scanning in accordance with an embodiment.

As illustrated with respect to FIG. 5, an embodiment utilizes real-time pattern recognition analysis to make determinations about the glucose levels of the subject represented by the composite signal. The pattern recognition analysis is based on additional information found at other frequencies in the composite signal (other than about 2.48 GHz), together with additional data about the subject to be tested. The scanning apparatus of an embodiment enables certain characteristic patterns to be detected that are common to subjects with high, normal and low glucose levels. Additional patterns also indicate when a subject is exerting excessive pressure on their finger or when their finger is not properly placed within the scanning apparatus. Still further patterns indicate when a subject has moved their finger during scanning or when a subject's finger is not oriented in the optimal position. Finally, the size of a subject's finger can result in significant variations in the composite signal, which variations can be diminished by accounting for the greater blood volume that exists in large fingers and the lesser blood volume that exists in small fingers, such as through measurement of the finger to be tested at a common point.

As a result, the analysis of the composite spectrogram signal of an embodiment, performed by software or specialized hardware within the computer 16, takes advantage of real-time software pattern recognition analysis in order to perform accurate analysis of a just-in-time captured composite spectrogram signal. This method of analysis of the composite signal enables more complex determinations to be made about the information represented by the composite signal. More importantly, this method of analysis enables rapid determinations about a subject's glucose level. Hence, a scanning device incorporating this technology could be placed in homes, businesses and common areas of stores, much like current blood pressure testing devices, and enable anyone utilizing the device to obtain an accurate measure of their current glucose level.

Other devices, such as portable scanning devices that do not require pin pricks, which could be put in a pocket or purse, would make many other types of applications possible. For example, since the quantity of glucose or blood sugar in a person's body at a given point in time is representative of the calories they have consumed and utilized as a result of exercise or simply living, their blood sugar level correlates well to their weight or performance management. If their blood sugar levels are higher than a normalized level, they may be in a position to gain weight, while if their blood sugar levels are lower than a normalized level, they may be in a position to lose weight. While this correlation is well known and incorporated into a number of weight management plans, prior art blood sugar testing devices have not made it practical to test someone's blood sugar levels multiple times a day to help manage their caloric intake and utilization. Embodiments change this situation, however, by enabling a user to carefully test and manage their caloric intake and utilization many times during the course of a day, thereby enabling use by anyone desiring to control their weight, including athletes, dieters, etc.

Likewise, an athlete's performance could be optimized through use of such a device by carefully monitoring blood sugar levels to make sure the athlete had the optimum amount of fuel for energy in their body at a needed time.

By coupling the blood scanning features of an embodiment to a computer equipped with additional weight management software, a user could track their weight gain or loss over a period of time, but without being relegated to making rough guesses about calories consumed, through food and drink, and utilized, through normal body functions and exercises performed. Performance management software could play a similar cooperative role. Alternatively, an embodiment could be coupled with a calorie counting type of diet, so as to prevent the user from straying from reality (i.e., "that donut was only 50 calories" or "I only had a half portion"). Certain safety features could also be incorporated if a user was consuming too few calories over a period of time or exercising too much, such as by disabling the scanning device and/or sending a message to a central office so as to enable a person to check on the user.

With reference now to FIG. 5, an example of just-in-time composite signal analysis, in conformance with an embodiment, is provided. The composite signal illustrated in FIG. 5, which is generated from a large set of spectral data sets, is representative of the type of signal generated during a glucose level test. The graph of the composite spectrogram signal 500 in FIG. 5 represents frequency, in Hertz (Hz), along the horizontal axis and differential amplitude, in decibels (dB) along the vertical axis.

Figure 7:
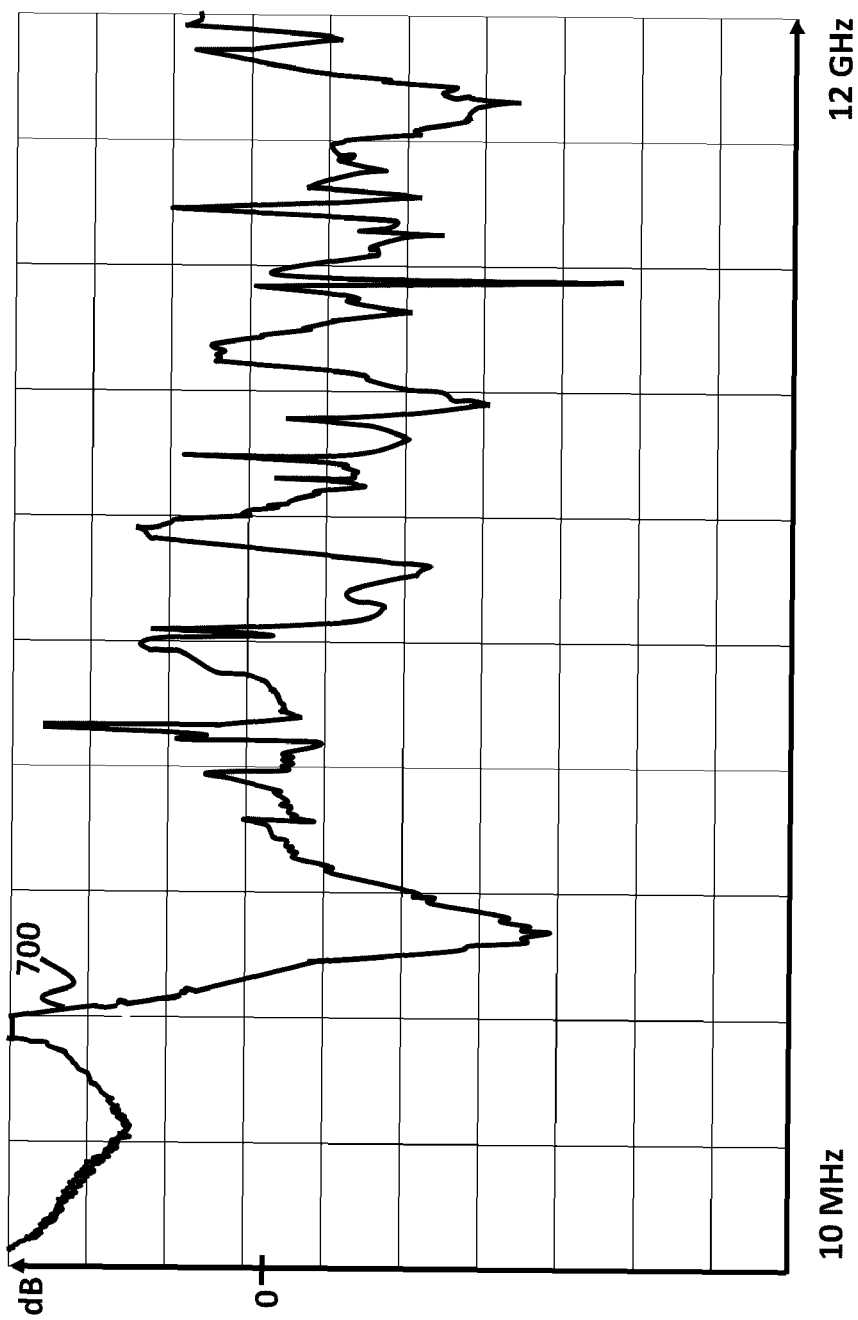
FIG. 7 is an illustration of a real-time composite spectrogram for biometric identification in accordance with an embodiment.
Figure 8:
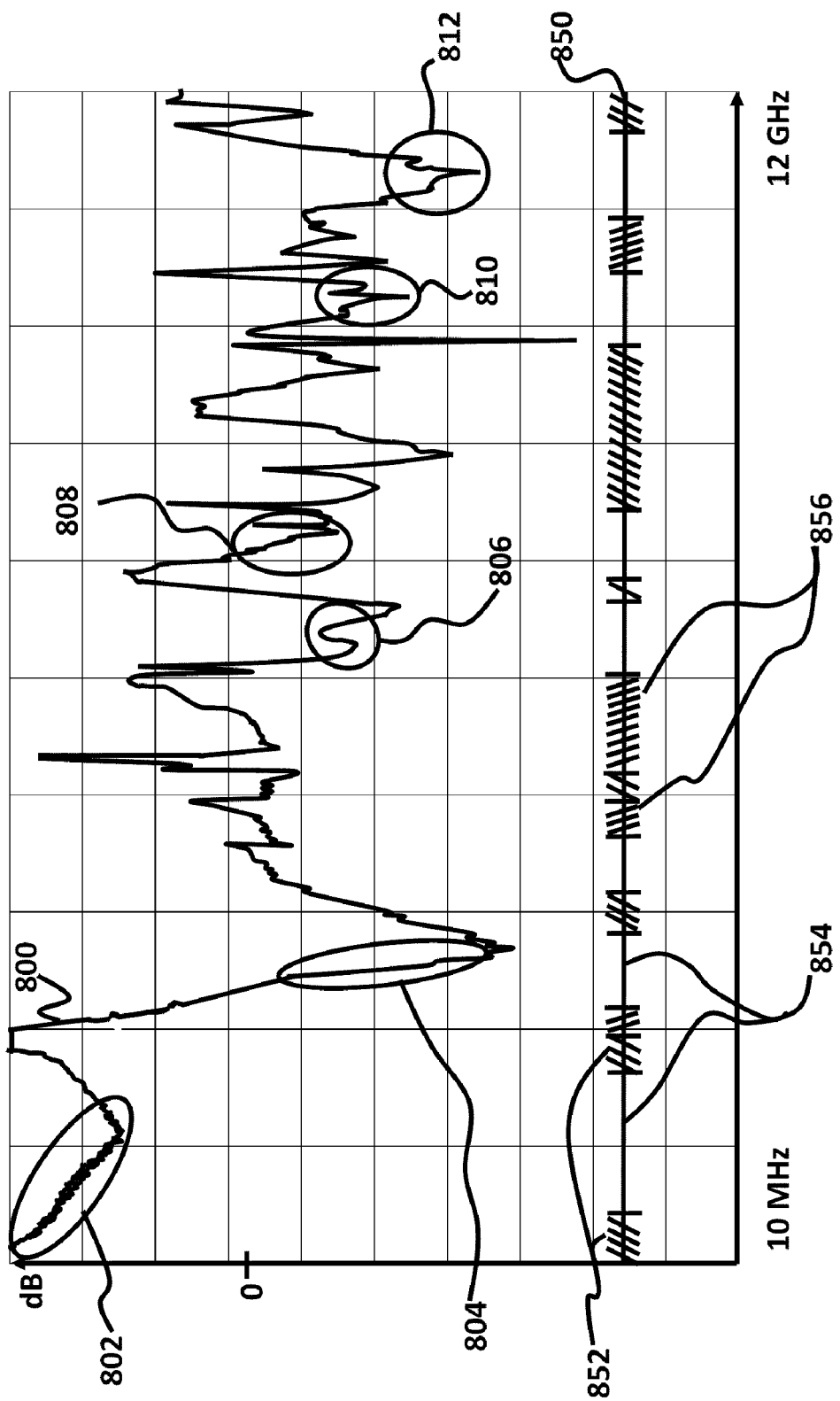
FIG. 8 is an illustration of a stored spectrogram for comparison to the real-time spectrogram of FIG. 7, and further illustrating the areas of difference and the regions of relevance between the two spectrograms.

The power or magnitude of the resulting composite signal is represented in decibels. The term "differential amplitude" is used to refer to the normalized amplitude signals that are generated by performing a scan first without a sample, performing a scan with the sample to be tested, and then subtracting the amplitude versus frequency results of the first scan from the results of the second scan. As illustrated in FIGS. 5, 7 and 8, the zero differential point is shown by the "0" at the approximate midpoint of the vertical axis in each graph.

There are four pattern components to the composite signal 500, and a fifth factor, a measure of the blood volume of the subject's finger, which are used to determine the subject's glucose level from the composite signal 500. When scanning for blood glucose levels, it is very important to determine at least a rough determination of the blood volume of the subject's finger, i.e., the size of the finger, at the point of measurement because smaller than normal and larger than normal fingers can skew the results if the resulting blood volume (less for small fingers and more for large fingers) is not taken into consideration.

Hence, the cross-sectional area of the finger at the approximate point of contact with the nodes is determined. This determination can be made in any of a wide variety of fashions, such as measuring the subject's finger with a piece of measuring tape, matching the subject's finger to a model of known size, or even including an automated finger measuring device inside the scanning apparatus that applies a small cuff or similar band around the finger to determine its size prior to scanning. The effect of this measurement on the glucose level determination will be discussed more fully below.

The dashed baseline 502 in FIG. 5 represents a decibel level, at the approximate 2.5 GHz frequency, that highly correlates to normal glucose levels. While the baseline 502 cannot be reliably used as the sole basis for measuring glucose levels, in the absence of comparative pattern matching as disclosed in the '048 patent, it can be used in conjunction with four other components of the composite signal 500 to reliably determine glucose levels. When referring to each of these components below, a reference to a component being "high" or "low" is in comparison to a median point for that component, and a reference to a component being "positive" or moving "upward" or "negative" or moving "downward" is relative to the scale position of "0" on the decibel vertical scale.

It should also be noted that the composite signal illustrated in FIG. 5, including the peaks, valleys and other signal components, is affected by the shape and strength of the magnetic field, the transmitting and receiving nodes, and numerous other factors, as previously discussed. The exemplary composite signals illustrated in FIGS. 5, 7 and 8 were created using a scanning device similar to that illustrated in FIG. 2. Changes in this device or the use of a differently configured device, such as illustrated in FIGS. 4A-4H, might cause the peaks, valleys and other signal components to shift up or down in frequency or cause other changes that would have to be accounted for in analyzing the resulting composite signal.

The first pattern component is the lowest point 504 (or decibel level) of composite signal 500. This lowest point typically occurs, but does not always occur, at approximate 2.5 GHz. When the lowest point 504 is at the baseline 502, the glucose level of the subject is most likely normal. When the lowest point 504 is above the baseline 502, the glucose level of the subject is most likely high. The further away the lowest point 504 is from the baseline, in the positive direction, the higher that glucose level is likely to be. Likewise, when the lowest point 504 is below the baseline 502, the glucose level of the subject is most likely low. The further away the lowest point 504 is from the baseline, in the negative direction, the lower that glucose level is likely to be. The terms "most likely" and "likely" are utilized because as previously stated, the baseline 502 alone, or comparison of the lowest point 504 to the baseline 502, only provides a rough estimate of a subject's glucose level, but it cannot alone be reliably utilized to determine a subject's glucose level, which is where the other components come in to play.

Sampling points 506A, 506B and 506C, which are sampled at a low frequency (approx. 100 MHz), represent the sample variation pattern component. This component is important because a subject inserting their finger into the scanning apparatus may exert more or less pressure on their finger, or move their finger around, which can cause the composite signal 500 to fluctuate as well, thereby causing the other components to change in some way. However, by sampling the composite signal 500 at each of the specified sampling points 506A, 506B and 506C, it is possible to remove many of the variations caused by finger movement or variation. For example, if the slopes of the lines formed between the three sampling points 506 are high, then the magnitude of the lowest point 504 is adjusted upward toward 0 dB. If the slopes of the lines formed between the three sampling point 506A, 506 B and 506C are low, then the magnitude of the lowest point 504 is adjusted downward.

The next pattern component is the trough 508 in the composite signal 500 formed by the lowest point 504. In its simplest form, the trough component 508 can simply be a measure of the width of the trough at a point just above 0 dB, or the entire area of the trough can be calculated. When utilizing width, if the magnitude of the trough component 508 is high (or wider than the median), then the magnitude of lowest point 504 is adjusted downward. When the magnitude of the trough component 508 is low (or narrower than the median), the magnitude of the lowest point 504 is adjusted upward toward 0 dB. Area is utilized in the same way, with a larger area being used to adjust the lowest point 504 downward, and a smaller area being used to adjust the lowest point 504 upward toward 0 dB.

The last fine-tuning pattern component is a high frequency signal at a specified point 510 at the end of the trough 508. The fine-tuning component is used for just that, to fine-tune the accuracy of detecting the blood glucose level for about 80% of subjects. The fine-tuning component, however, should not always be used because in the remaining 20% of cases, the use of the fine-tuning component could actually lower the accuracy of the measured blood glucose levels of those subjects. Hence, it might be necessary to analyze signal 500 with and without the fine-tuning component to determine if the results of the analysis improve with such use; if they do not, then they are not used. When the fine-tuning component is used, if the magnitude of the specified point 510 is lower than the median, then the magnitude of the lowest point 504 is upward toward 0 dB. When the magnitude of the specified point 510 is higher, the magnitude of the lowest point 504 is moved downward.

Composite spectrogram analysis utilizing different algorithms to detect quantitative relationships or to recognize patterns, similar in some ways to those techniques described above, could also be used to measure many other aspects of a subject's physical condition or composition, as well as many other characteristics of other types of samples. For example, composite spectrogram analysis could be used to measure or detect the presence of cholesterol (HDL and LDL as well), red and white blood cells, proteins (including antigens for determining blood type), hormones, steroids, lipids, C-reactive proteins, bacteria, yeast, viruses, pathogens, heavy metals, calcifications, and other biological markers, agents or substances. Once one or more components of a composite signal have been identified as corresponding to any substance that can be found in the blood, tissue or bone of a subject, the presence and levels of that substance can be detected and measured utilizing an embodiment, without invading the subject's body, without having to compare that subject's current results with prior results, and in near real-time due to the speed of the computer aided analysis.

This would enable doctors and emergency medical technicians to perform on the site blood and tissue analysis without further traumatizing the subject and without endangering the doctors or technicians with potentially tainted blood. For example, being able to promptly determine if a patient had consumed alcohol, illegal drugs or even prescription drugs prior to or while transporting that patient to the hospital could prove life-saving in many situations. It would also enable doctors to perform more appropriate diagnosis and treatment of patients without all of the delay created by the current need for blood testing laboratories. It could also take the place of urine analysis testing or blood testing to test drivers, athletes, students, inmates, parolees, employees and countless others for the use of controlled substances, absorption levels of prescription drugs, alcohol and other foreign substances.

When a device in accordance with an embodiment is utilized in a physical facility, the size, construction and operation of the device may be less critical than when utilized in a remote location, such as at the scene of an accident, the side of the road, or at multiple access locations throughout a building. The cost associated with installing bulky machinery at multiple different locations, or the impracticality of utilizing such machinery at a remote location, requires a different solution.

Figure 6:
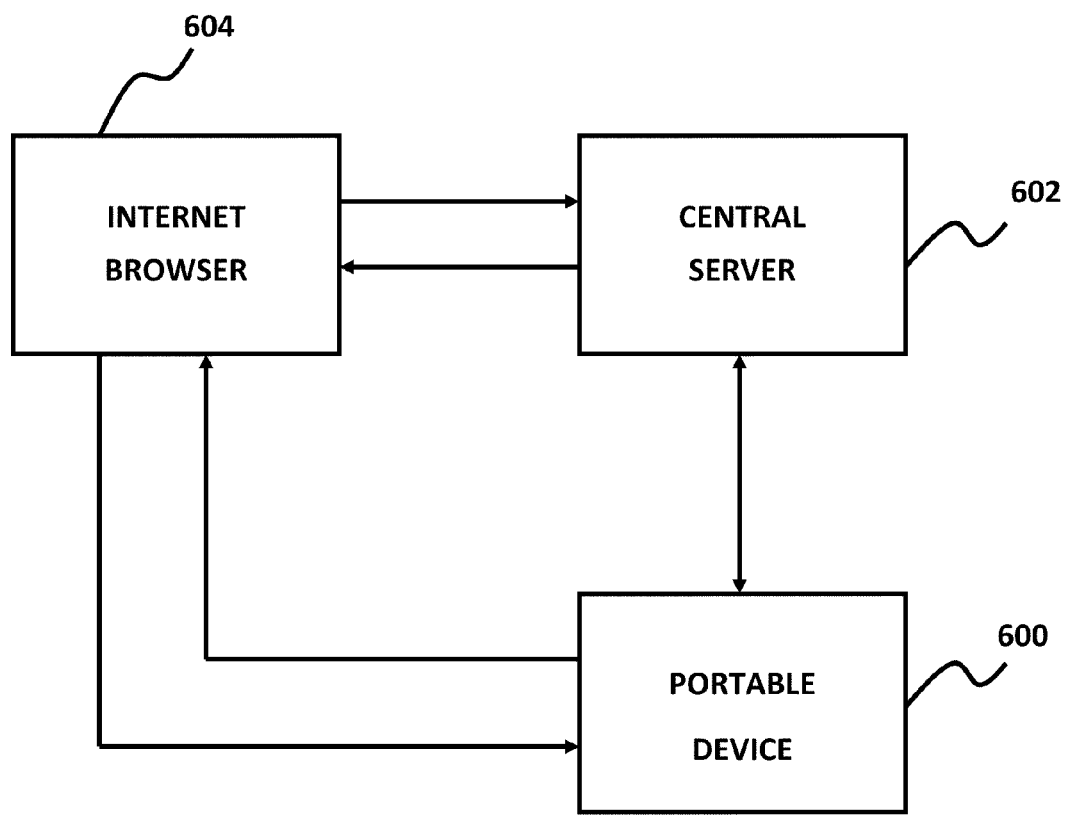
FIG. 6 is a block diagram illustrating a remote detection and analysis configuration in accordance with an embodiment.

One potential alternative solution is illustrated in FIG. 6, which illustrates a portable scanning device 600 that is capable of capturing raw data from a person or object to be tested at a remote location and wirelessly communicating that raw data to a central server 602. The raw data collected by device 600 could, in turn, be encoded utilizing digital rights management technology, or some similar type of encryption or data rights management technology, so as to further prevent a competitive device from being able to compatibly communicate with the central server 602. The server 602 would then process the raw data according to one or more proprietary analysis programs to produce a diagnostic result for the raw data and wirelessly communicate the diagnostic result back to the device 600. In some applications, the portable device 600 could be very simple and include a few predetermined scanning operations (selected through operation of a physical or electronic button on a touch screen), such as an alcohol test, a methamphetamine test, and one or two other tests, that could be selected by a law enforcement official in the field prior to collecting and communicating the raw data.

In other applications where the user of the remote device wanted a further range of tests, or so as to further reduce the cost of equipment at a remote location or a physical facility and to maintain control over the analysis program, the portable device 600 could be combined with an Internet browser 604 so as to enable the user to operate Internet-enabled applications and to perform other functions. For example, a personal query could be communicated from Internet browser 604 to central server 602 requesting the performance of one of a large number of different tests. The central server 602 would then communicate with the portable device 600 to request and collect the necessary raw data, which would be communicated back to the central server 602. After processing the raw data, the central server 602 would then communicate the diagnostic results, as well as other data, such as tabulated charts and histories, medical opinions, interpretations and other data, back to the browser 604 for the user. The portable device 600 could be configured to identify itself to the central server 602 for each test to be run or for each data package to be sent, so that the user of the portable device 600 could be charged accordingly, such as on a per test/per download basis, on account, etc. Other forms of identification and payment arrangements could also be possible depending on how much intelligence and how many user interface controls are built into the portable device 600.

While many characteristics of a sample can be detected and measured only using just-in-time analysis based on the recognition of pattern components, to improve the accuracy of the results of some tests, it is desirable to also use some form of pattern matching. For example, biometric identification applications may require a composite spectrogram signal representing a currently tested person to be compared to a database of previously tested persons to positively identify the person being tested or to reject him or her. However, it is neither necessary, nor desirable, to rely on the pattern matching test alone, especially when recognized pattern components can be used to improve the overall analysis.

FIG. 7 is a real-time spectrogram (R) 700 representing a person (P) who was scanned or tested in accordance with an embodiment. As with FIG. 5, the vertical scale represents decibels and the horizontal scale represents frequency, only unlike FIG. 5, in FIG. 7 the frequency scale ranges from 10 MHz to 12 GHz. The composite spectrogram (signal) illustrated in FIG. 7 includes a number of prominent peaks and valleys, the combined position and shape of which, after processing, may be unique to every person.

While changes in a subject's general physical condition, recent dietary consumption, or other factors might alter their composite spectrogram from day to day, week to week, or month to month, possibly causing one person's signal to approximate another person's signal, many of these variances can be filtered out and otherwise accounted for to help reveal each person's unique spectrogram signal shape. For example, it has been observed that some regions of the composite spectrogram change much, while other areas change little, so from scan to scan the raw data can be inconsistent. By applying a filter to a composite spectrogram as part of a recognition algorithm, it is possible to filter out some of the courser variations in the raw data, while minor variations can be accounted for through quantitative analysis of the raw data, thereby enabling the recognition algorithm to focus on the areas of the composite spectrogram that represent unique characteristics of an individual.

FIG. 8 is a stored spectrogram (S) 800 representing the same person P in FIG. 7, but was previously scanned from person P and stored in memory 14 for comparative purposes by CPU 10. If S 800 is known to represent person P, but R 700 is unknown, then it would make sense to compare R 700 to S 800 in order to determine if R 700 also represents person P. However, while a visual or electronic comparison between the two spectrograms 700 and 800 would illustrate some differences, not all of these differences are important because it is known that some components of the spectrograms change frequently, even for the same person, and are not considered reliable identifiers, while other small changes in a signal component are infrequent and might have great significance from an identifying perspective. For example, an embodiment performs the following six comparisons to identify changes that may be of significance: $\alpha\emptyset$, $\alpha 1$, $\alpha 2$, $\beta\emptyset$, $\beta 1$ and $\beta 2$, where $\alpha$ represents a change in spectrograms of a single person versus herself/himself, where $\beta$ represents a change in spectrograms of a single person versus a different person, where $\emptyset$ represents a small change, where 1 represents an infrequent change, and where 2 represents no change.

With respect to FIGS. 7 and 8, the primary components or areas of difference between R 700 and S 800 are illustrated on FIG. 8 as the circled areas 802, 804, 806, 808, 810 and 812, although other slight differences might exist between the two signals in other areas. These differences can be quantified using a number of different techniques, such as a filtering algorithm or even the least squares or the sum of the squared error technique, which attempts to find a best fit. Utilizing this technique, if the sum of all variations between the signals at a number of specified test points (selected frequencies along the horizontal line) is less than some predefined number, then the two signals represent the same person. If the sum of those variations is greater than that predefined number, then R 700 represents a different person than S 800.

However, as noted above, some variations between the signals are meaningful and some are not, so an embodiment does not rely upon filtering or the least squares technique alone to determine whether or not R 700 is S 800. As further illustrated in FIG. 8, a horizontal relevancy line 850 has been added below the spectrogram 800. The relevancy line provides an indication of the relevancy of different portions of spectrogram 800 toward the positive or negative identification of a person scanned. The relevancy line 850, as illustrated in FIG. 8, is comprised of three types of regions, forward slash regions 852, blank regions 854, and backward slash regions 856. Only three types of regions are shown in FIG. 8 for purposes of simplifying the drawing, but as many regions as were necessary could be utilized.

Forward slash regions 852 correspond to regions of lower relevance, meaning that there can be a bigger difference between the amplitude in decibels of a point ($f_1$) at a particular frequency on R 700 within region 852 from the amplitude of a point ($f_2$) at that same frequency on S 800. For purposes of simplicity, this difference is referred to as $\Delta$, which is the difference between $f_1$ and $f_2$. Hence, the forward slash regions 852 would have a higher threshold level that $\Delta$ would have to exceed before a variation between R 700 and S 800 was considered to be meaningful. Blank regions 854 correspond to regions of high relevance and therefore have a low threshold level for $\Delta$. Backward slash regions 856 correspond to regions of medium relevance and therefore have a threshold level for $\Delta$ between that of blank regions 854 and forward slash regions 852.

Furthermore, merely exceeding the threshold for $\Delta$ within a particular region may or may not be significant depending on the particular frequency level and the region involved. This rule is further illustrated with reference now to FIG. 9, which shows a graph of $\Delta$ compared to $f(\Delta)$. The vertical axis $f(\Delta)$ represents values (x) that are assigned to $\Delta$ based on $\Delta$'s position on the line 900, which is a graph of all possible $\Delta$s for that particular point on the spectrograms 700 and 800. As shown, the line T on the horizontal line $\Delta$ represents the threshold for a point within a region of the spectrograms 700 and 800. When it is known that R 700 and S 800 correspond to the same person, a point 902 on line 900 would be expected to be below the threshold T and would therefore be assigned a low $f(\Delta)$ value, in this case the arbitrarily assigned value of $0.01(x)$. However, if a point 904 is at a much higher point on the line 900, i.e., further past the threshold T, it is assigned a much higher $f(\Delta)$ value, in this case the arbitrarily assigned value of $3.6(x)$. Since the probability of R 700 belonging to the same person represented by S 800 goes down the further $\Delta$ is past the threshold T, the values $f(\Delta)$ increase exponentially along the vertical line $f(\Delta)$ so as to assign higher and higher values to higher $\Delta$ values.

Figure 9:
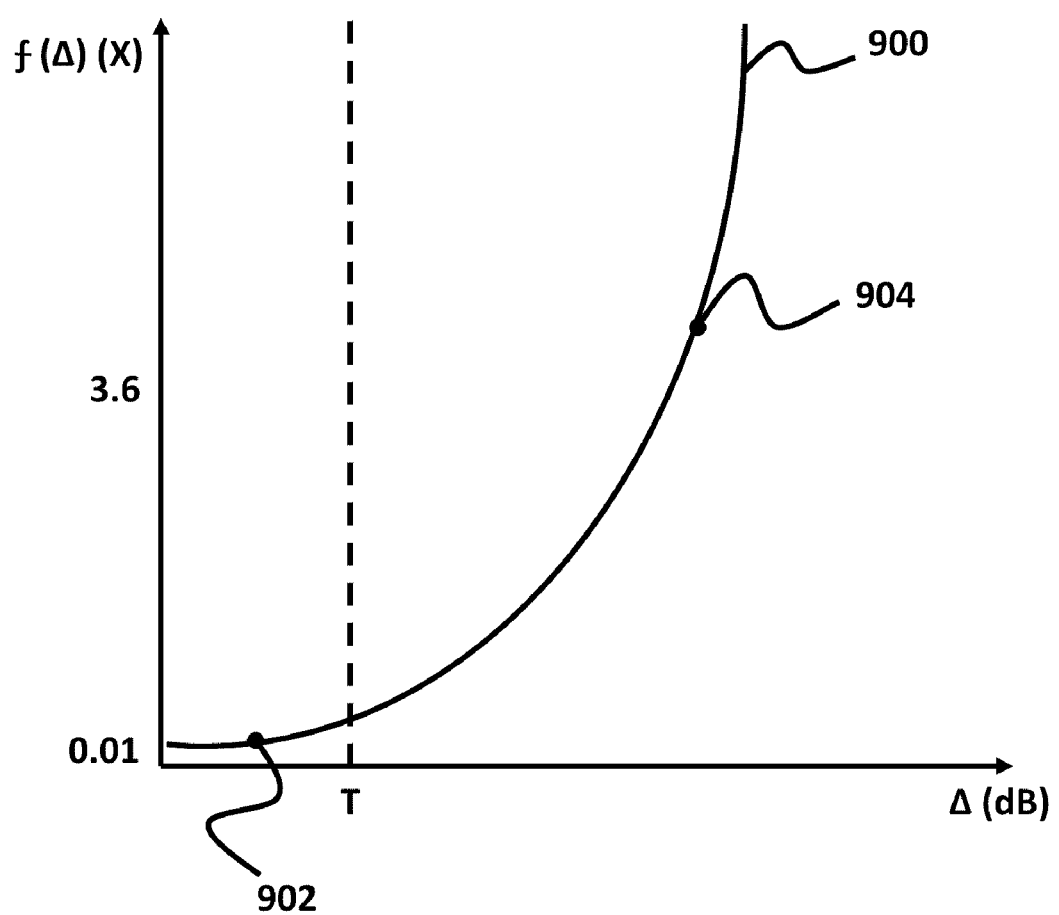
FIG. 9 is an illustration of a filtering analysis in accordance with an embodiment.

As with the sum error squared technique described above, the $f(\Delta)$ valuations for each test point on the spectrograms 700 and 800 can also be summed, with the result effectively being a filtered sum. If the filtered sum for R 700 versus S 800 exceeds a predefined number, then R 700 represents a different person than S 800, and if the filtered sum is below that predefined number, then R 700 and S 800 represent the same person. The predefined number itself is not significant because it depends entirely on the values assigned to $f(\Delta)$, which can be arbitrary. Hence, the numbers for $f(\Delta)$ in FIG. 9 are for illustration purposes only and could be readily changed without departing from the teachings of an embodiment.

Figure 10:
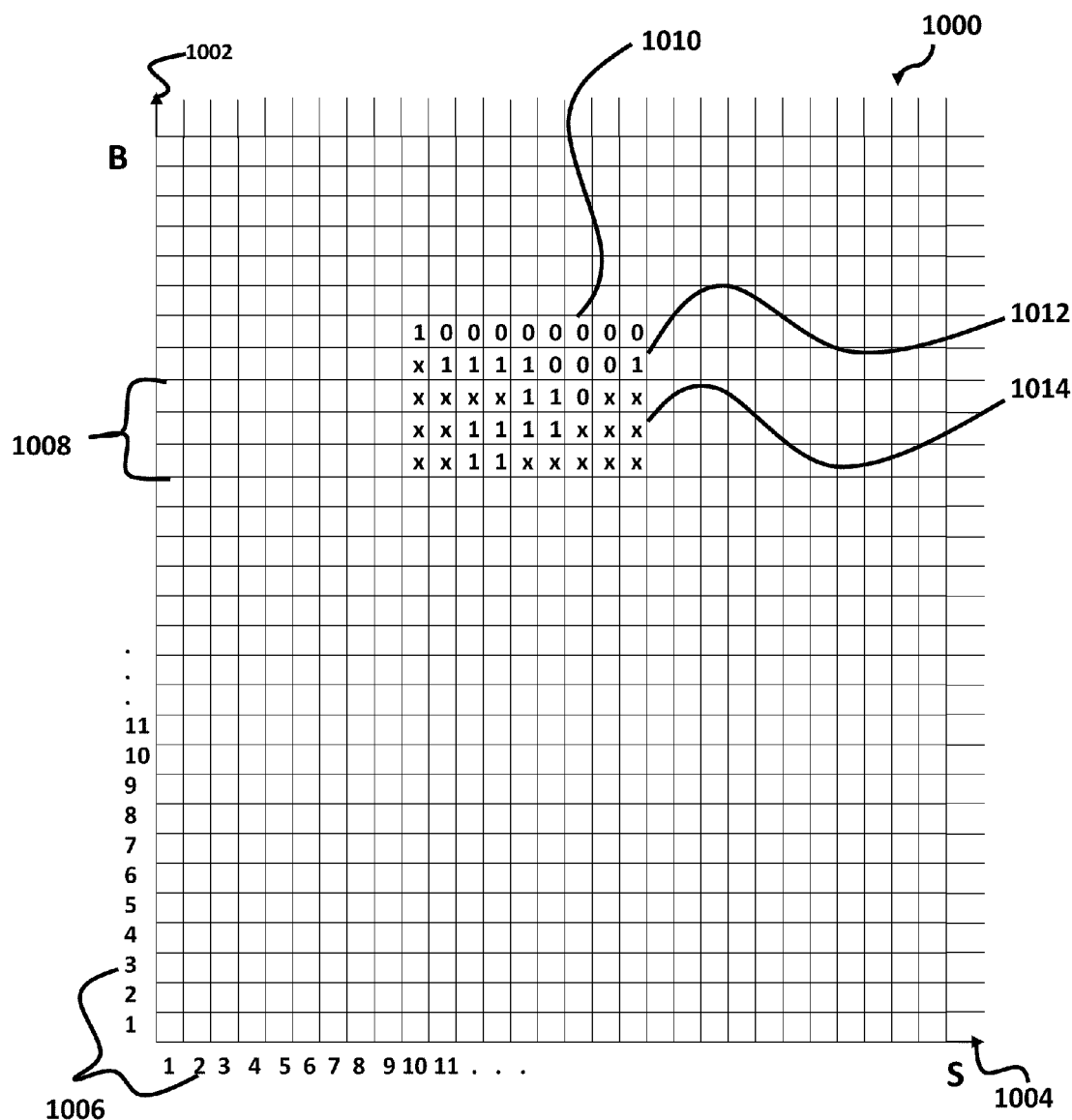
FIG. 10 is an illustration of a personal identity determinator (PID) in accordance with an embodiment.

An additional technique to be utilized when comparing spectrograms 700 and 800 is illustrated in FIG. 10, which partially depicts a visual pattern matching technique in accordance with an embodiment, referred to herein as a personal identity determinator (PID). FIG. 10 is a PID graph 1000 of B, a baseline spectrogram, versus S 800, where B is the vertical axis 1002 and S is the horizontal axis 1004. The baseline spectrogram B could be formed in a number of different manners, such as forming B from the mean or median of all spectrograms of a large population of people. The points 1006 along B and S represent the sampling points on each spectrogram. While only a limited number of such points 1006 are represented in the PID graph 1000, the total number of points 1006 could be any number. For example, as noted above when discussing the number of sampling points used in a frequency range from about 100 MHz to about 12 GHz, a total of about 3,201 sampling points could be used for both B and S.

However, utilizing that many sampling points in a PID graph will require a significant amount of computing power, memory and processing time, so it is preferable to use between two and three hundred points 1006, representing the approximate number of peaks and valleys in a typical biometric spectrogram for most people. Given the impracticality of representing hundreds of sampling points for both B and S in the PID graph 1000 of FIG. 10, only thirty or so sampling points 1006 are therein illustrated for both B and S. Accordingly, not all of the resulting sampled point squares 1008, representing the crossing points between the same sample points along B and S are illustrated, and only a handful of the sampled point squares 1008 are filled in with a "0" 1010, a "1" 1012 or an "x" 1014, as further described below.

For each sampled point square 1008, a comparison is done between the value of a sampled point 1006 on the spectrogram B 700 and the value of the same sampled point 1006 on the spectrogram S 800. If the value of B for a first sample point is greater than the value of S for the same sample point by more than a threshold level (B>>S), then the corresponding sampled point square 1008 is assigned a "0" value. If the value of B for a first sample point is greater than the value of S for the same sample point by less than a threshold level (B>S), then the corresponding sampled point square 1008 is assigned an "x" value. If the value of B for a first sample point is less than the value of S for the same sample point by less than a threshold level (B<S), then the corresponding sampled point square 1008 is assigned an "x" value. If the value of B for a first sample point is less than the value of S for the same sample point by more than a threshold level (B<<S), then the corresponding sampled point square 1008 is assigned a "1" value.

Whether a sampled point square 1008 is assigned a "0" 1010 or a "1" 1012 value because B is greater or less than S by more than the threshold is not critical. What is important is that sampled point squares 1008 are thrown out or assigned an "x" 1014 value when B is greater or less than S by less than the threshold. This is important because small differences between the values of B and S could result from noise, thereby making those differences unreliable.

Once all of the sampled point squares 1008 have been filled in, a pattern will emerge of 0's, 1's and x's that is unique to that PID graph 1000. The pattern of the B versus S PID graph 1000 can then be stored and compared to a real-time created PID graph corresponding to person P, using B versus R, to see how closely the two PID graphs match. These patterns could be compared using any of a number of well known pattern matching techniques. For example, the patterns can be compared row-wise or column-wise, with every exact match adding a point to a total score, with the total score determining the similarity between R and S. The closer the proximity between the patterns of 0's, 1's and x's on the two PID graph, the greater the likelihood that R and S correspond to the same person.

Figure 11:
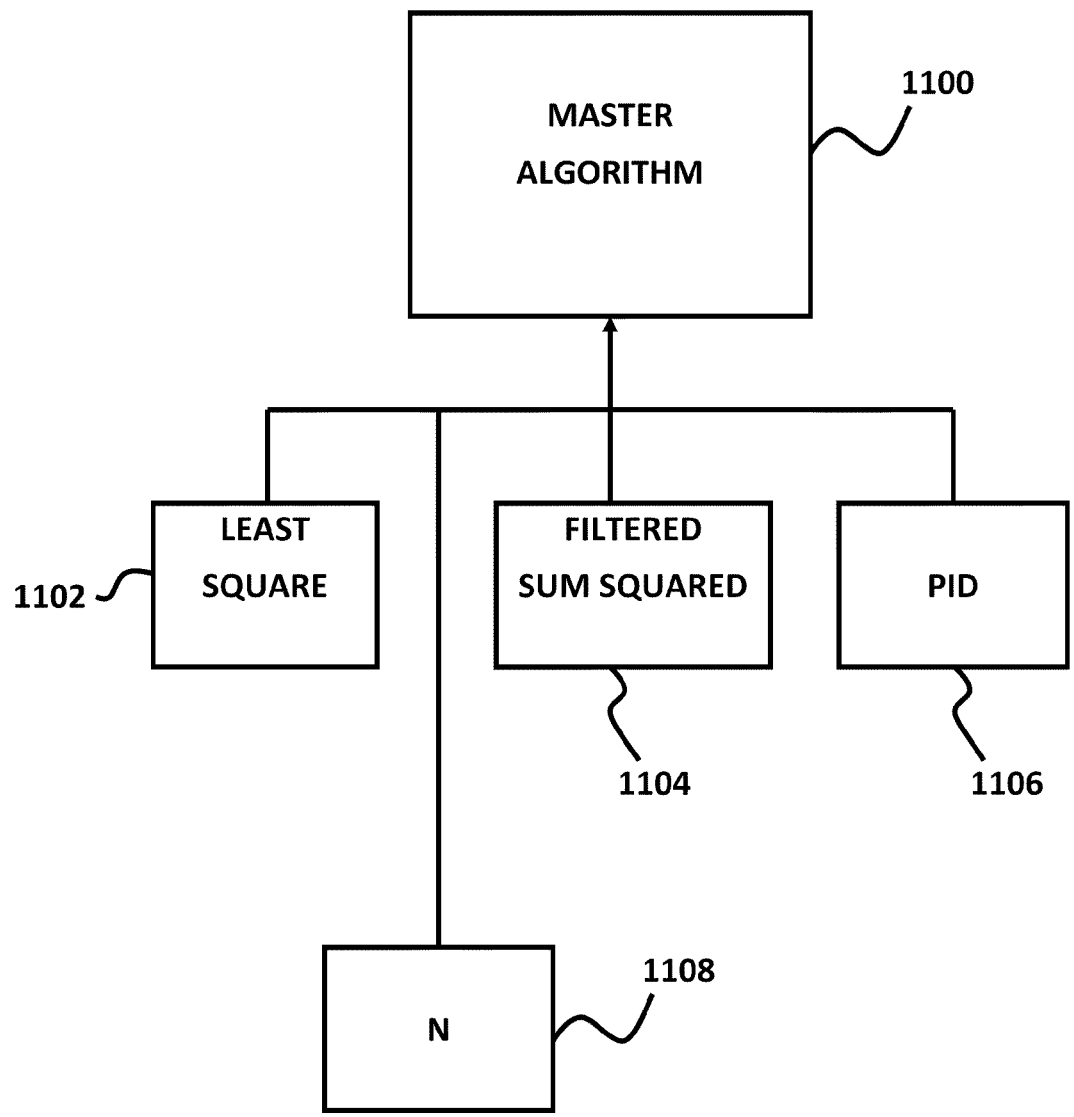
FIG. 11 is a block diagram illustrating the master biometric identification algorithm and its sub-element algorithms.

Although three different methods of comparing spectrograms 700 to 800 have been discussed, many additional methods are possible. To some extent, the more comparison methods utilized, such as in combinations of different techniques, the higher the reliability of the biometric identification application. Of course, some comparison methods are more significant than others, so it may be desirable to use a master biometric identification algorithm with each of the comparison methods as its sub-element algorithms to factor in which sub-element algorithms should be utilized in making a biometric identification and what degree of importance those sub-element algorithms should play in the overall identification determination. As illustrated in FIG. 11, the least square comparison 1102 could be one sub-element to the master algorithm 1100, while the filtered sum square comparison 1104 could be another sub-element, and the PID 1106 could be the next. As denoted by N 1108, any number of additional sub-elements could also be utilized in place of or in addition to those illustrated.

As previously noted, an embodiment can be utilized to perform many different tasks or applications. The detection and analysis method to be used in each instance will vary according to the task. For example, scans for human blood components would typically use detection and analysis methods similar to those used to scan for blood sugar levels, but could also use one or more of the methods used for biometric identification, where a known stored signal is compared to a real-time signal. These same types of methods could be used for agricultural inspection, food processing operations, security applications, environmental testing, manufacturing operations and many other applications. Authenticity applications would also be possible, where a security marker is used to mark and subsequently identify a valuable object.

Additional analysis techniques that could be utilized to detect glucose, biometric identification, etc., and which could be used in place of or in addition to N 1108 of FIG. 11, are further discussed below. In an embodiment, a particular algorithm, referred to herein as Algorithm-J, uses multiple and/or linear regression type calculations to determine, at a given frequency, or at various combinations of frequencies, an instantaneous correlation coefficient, R2 (R-Squared), between the known values of, for example blood glucose, and their corresponding "calculated function", such as the ratio of differential amplitudes at two or more different frequencies, or the sum of differential amplitudes at two or more different frequencies, and so on. The procedure used to find "the best known functions" to calculate, is that once you pick one to try and set-up the program to run through the raw data, the CPU 10 finds and reports the regions of value, if any. For example, calculations on data from a "Glucose Tolerance" test, returned 25,140 combinations of the frequency function being calculated that resulted in an R2 value of 0.40 or greater, with the peak R2 value being 0.92. Furthermore, 20 combinations of the frequency function being calculated resulted in an R2 value of 0.84 or greater. Using the latter top 20 frequency functions in a hypothetical ensemble to estimate (simulate) a subject's blood glucose reading, using an embodiment of a sensor driven by a program using Algorithm-J, provided an R2 value of 0.95.

Figure 12:
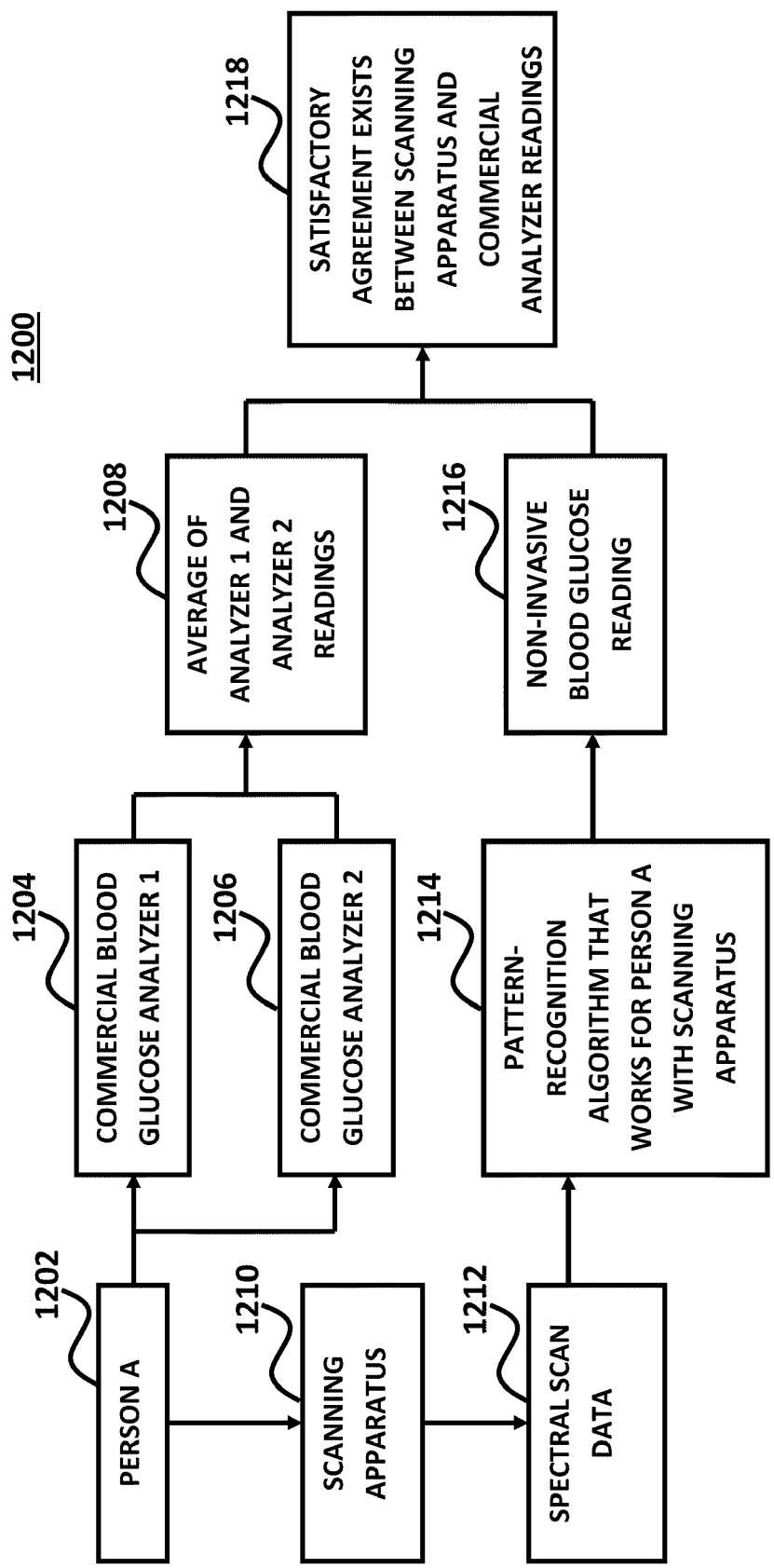
FIG. 12 is a flow chart representing an operating method for fine-tuning pattern recognition algorithms.

An embodiment of a method for fine-tuning pattern-recognition-algorithms for use with an embodiment of the non-invasive sensor described above with respect to FIG. 4 is now described. In the analysis of blood glucose levels in live human fingers or other substances, the various algorithms resulting there from, the improved non-invasive blood glucose measurement apparatus enabled thereby, and the subsequent generations of such apparatus enabled there from, provides a quick and inexpensive method of fine-tuning pattern-recognition-algorithms for different embodiments of such scanning apparatuses. A flow chart illustrating how glucose readings from two different finger-stick meters is normally compared to a scanning apparatus scan is shown in FIG. 12. A flow chart of a Fine Tuning Method A, where a prior subject uses a new sensor or the same sensor, is shown in FIG. 13.

In the flowchart 1200 of FIG. 12, a Person A 1202 has their blood glucose analyzed by a first commercial analyzer, step 1204, and a second commercial analyzer, step 1206. Step 1208 computes the average of the readings from the first commercial analyzer 1204 and the second commercial analyzer 1206. The blood glucose of Person A 1202 is also analyzed using the scanning apparatus 1210, resulting in a spectral data scan, step 1212. Step 1214 uses a pattern recognition algorithm that works for Person A with the scanning apparatus 1210. The output of the pattern recognition algorithm is a non-invasive blood glucose reading, step 1216. Finally, the averaged readings of the commercial analyzers and the reading of the scanning apparatus are checked for agreement, step 1218. For example, during calibration, if the difference between the commercial analyzer readings and the scanning apparatus readings are greater than an agreement threshold, then the user can be prompted to repeat the process by doing a second sweep with the scanning apparatus. In addition, while the flowchart 1200 shows the use of two blood glucose analyzers, the blood glucose level could be checked by more than two blood glucose analyzers in order to improve the accuracy of the blood glucose measurement.

Figure 13:
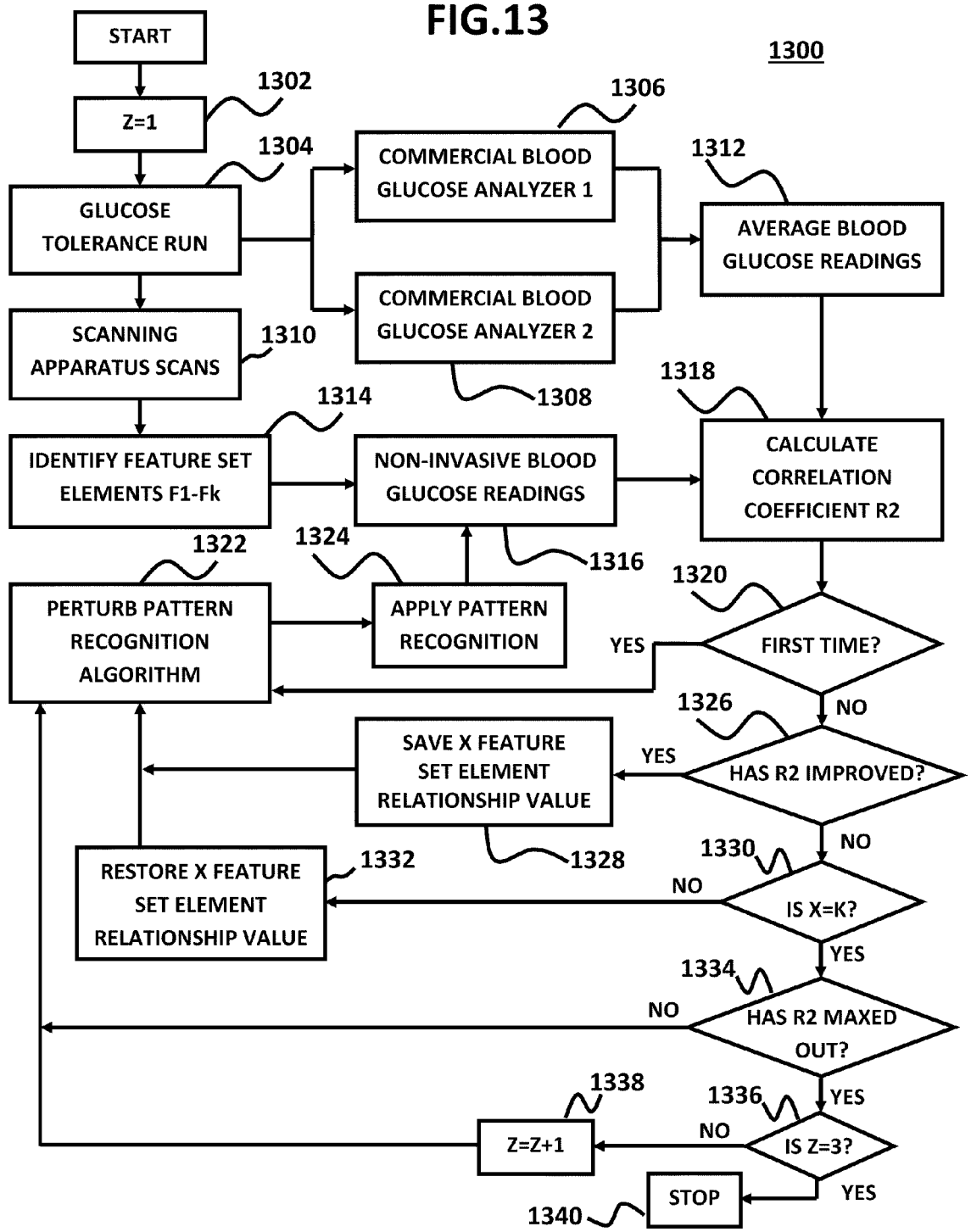
FIG. 13 shows a flow chart representing a method for fine tuning pattern recognition algorithms for instances when a prior subject uses a new sensor.

FIG. 13 shows a flow chart 1300 of a fine tuning method for a pattern recognition algorithm, illustrating the optimization of a scanning apparatus to work with Person A. First, a counter variable Z is set to 1, step 1302, and then Person A undergoes a glucose tolerance run, step 1304. This consists of performing a set of N finger-stick readings with a first commercial blood glucose analyzer, step 1306, and a second commercial blood glucose analyzer, step 1308, and a corresponding set of N scans performed with the scanning apparatus, step 1310. The finger-stick readings and scans are done at five to ten minute intervals while Person A's blood glucose level rises from a fasting level to a high level and then back down to the fasting level. In step 1312, each first reading from the first commercial analyzer, step 1306, is averaged with the second reading from the second commercial analyzer, step 1308.

The pattern recognition algorithm being tuned is used to identify underlying feature set elements F1 through Fk, where k is the total number of underlying feature set elements, step 1314. This results in a set of non-invasive blood glucose readings, step 1316. Step 1318 calculates the correlation coefficient R2 between the finger-stick readings and the non-invasive readings calculated from the pattern recognition algorithm. If it is the first time that the correlation coefficient has been computed, step 1320, then the process continues to perturb the pattern recognition algorithm in order to improve its performance, step 1322.

The perturbation of the pattern recognition algorithm is done by perturbing the value of relationship of underlying feature set element Fx, where x is the $x^{th}$ element in the list of feature elements from one through k. The perturbation of the underlying feature set element Fx is done relative to all the other feature set element of the pattern recognition algorithm. Once the feature set elements used in the pattern recognition algorithm have been perturbed, step 1324 applies the pattern recognition algorithm to the data collected from step 1310, resulting in a new a set of non-invasive blood glucose readings 1316. The new set of non-invasive blood glucose readings are used to calculate the correlation coefficient R2 with respect to the finger-stick readings in order to determine whether the perturbation improved the performance of the pattern recognition algorithm, step 1326.

If the pattern recognition algorithm has been perturbed at least once, then the value of R2 is checked in step 1326 in order to determine whether the correlation coefficient R2 has improved due to the perturbations introduced into the pattern recognition algorithm. If R2 has improved, then the new x feature set element relationship value is saved, step 1328, and the process continues to step 1322 for further perturbations. If the value of R2 did not improve with the introduced perturbations, then step 1330 checks to see whether each element from the underlying feature set elements has been perturbed. Step 1330 performs this check by determining whether the last underlying feature set element to be perturbed is the last element of the set.

If there are still other elements that can be perturbed, then step 1332 restores the $x^{th}$ feature set element relationship value to its value prior to being perturbed, and the value of x is incremented in order to perturb the next element in the set, the perturbation being done in step 1322. If each element from the underlying feature set elements has been perturbed, then step 1334 checks whether R2 has maxed out. If R2 has not maxed out, then the algorithm is perturbed once again in step 1322. At this point, in an embodiment the perturbation in step 1322 restarts with the first element, element 1. In another embodiment, the perturbation in step 1322 restarts with a random element between 1 and k.

In step 1334, if R2 has maxed out, then the counter variable Z is checked to see whether its value is equal to 3. If the value of Z is not equal to 3, then the value of Z is incremented by one in step 1338, and the algorithm is perturbed in step 1322. If the value of Z is equal to 3, then the process stops. At this point, the pattern recognition algorithm has been optimized to work for Person A with the scanning apparatus used in step 1310. By initializing the variable Z to 1 and setting a stopping condition of Z=3, it allows for every element in the feature set of the pattern recognition algorithm to be perturbed two times. A higher value of Z for the stopping condition would allow for further exploration of perturbations of elements of the feature set, with the further exploration possibly allowing for the pattern recognition algorithm to be improved significantly.

In an embodiment, when a pattern recognition algorithm is being optimized for the same Person A but with a new scanning apparatus, then the pattern recognition algorithm that was fine tuned with flow chart 1300 can be used as the starting algorithm to be perturbed and optimized to work with the new scanning apparatus. Other alternative methods that can be used to fine-tune the performance of the pattern recognition algorithm include hill climbers and genetic algorithms.

The fine-tuning and determination methods both utilize spectral data sets derived from scans of fingers. One problem when working with an individual is repeatability of finger placement in the scanning apparatus and finger pressure on the electrodes or guide pieces in the sensor. Small errors in finger placement of the same finger from time to time introduce errors in the corresponding spectral data set. Portions of the spectral data relating to an individual can be utilized in specific comparative calculations to determine possible finger placement error. When the apparent placement error is small, the scanning apparatus announces or otherwise signals to the person, that the finger placement is excellent, or if there is a larger placement error, the person can be told that the placement is not as good as last time, or un-acceptable, or to please try again. Only when the finger placement is found to be "excellent", does the non-invasive blood glucose algorithm begin scanning spectral data to measure the person's blood glucose level. Then, by accumulating and averaging the successive excellent scans over time, and comparing each new spectral data set to the accumulated average, the individual can be trained how to place their finger so as to reduce finger placement error going forward. Reduction of finger placement error will improve the accuracy of the non-invasive blood glucose measurement.

An embodiment is directed to a method for analyzing spectral data sets. The scanning apparatuses disclosed herein are capable of measuring the real and imaginary components of transmitted RF signals and the real and imaginary components of reflected RF signals. The real components represent the purely resistive properties of the sample (and associated scanning apparatus parts) placed within the scanning apparatuses, while the imaginary component represents the capacitive and inductive properties of the sample (and associated, scanning apparatus parts). The computer 16 can also work with the transmitter 18 and receiver 20 to measure phase and power, which are derived from the real and imaginary components (also called the "raw components") of the reflected and transmitted signals. For example, total log magnitude power can be derived as follows from the real and imaginary components (using log to the base 10):

$$Power = 20 \times \log(\sqrt{Real^2 + Imaginary^2})$$

wherein "Real" is the real component of either the transmitted RF signal or the reflected RF signal and "Imaginary" is the imaginary component of either the transmitted RF signal or the reflected RF signal, all signals measured in root mean squared (RMS) volts, such that total transmitted power is derived from the real and imaginary components of the transmitted RF signal.

Referring back to FIG. 1, the transmitted RF signal is best understood as that portion of the transmitted signal that is received by the receiver node 24 after having passed through or around the sample (referred to herein as S21—which refers to signals received at port 2 of the receiver 20 from port 1 of the transmitter 18), while the reflected signal (referred to herein as S11—which refers to signals received at port 1 of the transmitter 18 from port 1 of the transmitter 18) is comprised of two portions, the portion that is reflected from the sample back into the transmitter node 22 and to the receiver 20, and the portion of the transmitted signal that is never actually transmitted by the transmission node 22 because of inefficiencies in the circuitry and is reflected into the receiver 20 from the transmission node 22.

The embodiment first requires a known sample to be registered with the computer 16 based on a variety of known conditions, so an unknown sample can subsequently be analyzed to determine its unknown conditions. For example, a human subject may place a finger within the scanning apparatus to have their unknown glucose level determined by the computer 16, but this first requires the same human to have the same finger tested by the scanning apparatus when the human's glucose levels are known, and preferably at different glucose levels. Hence, the human (referred to as a patient herein) would be required to test a finger with a traditional glucose meter (a finger prick device) after fasting and then immediately place an adjacent finger into the sensor to be scanned or tested by the sensor, the adjacent finger is used to keep from getting blood on the sensor surfaces from the pricked finger. The patient would then be required to drink a highly sweetened liquid (such as Glucola), which causes the patient's glucose level to rise. As the patient's glucose level rises, the patient's finger would be tested with a glucose meter and scanned by the sensor, and then as the patient's glucose level begins to return to a more normal level, the patient's finger would be tested with the glucose meter and scanning apparatus to develop a complete set of different glucose levels (high, low and normal). Since the variance between different glucose meters can be significant, it may be desirable to test each patient with at least two different glucose meters and average the results, as illustrated in FIG. 12.

When the patient's finger is placed in the scanning apparatus, the transmitter 18 transmits a series of RF signals starting at a base frequency and stepping up numerous times to higher frequencies until reaching a maximum frequency. Numerous different frequency ranges can be utilized. An embodiment uses a frequency range between about 0.3 MHz and about 20.1 GHz. The number of steps taken within the frequency range can also vary significantly. An embodiment uses an equal number of about 16,000 sampling points over the frequency range, but significantly smaller sets of sampling points could be used, equally spaced through the frequency range, or specific frequencies could be selected for a specific type of test. The total transmitted power signal received by the receiver 20 at each of the 16,000 or so sampling points is then recorded and processed.

The initial step of the process in this sampling embodiment, referred to herein as the "L-21 algorithm," involves taking the total transmitted power signal recorded for the first sample point and dividing it by the total transmitted power signal recorded for each of the remaining samples points (i.e., 2/1, 3/1, 4/1, 5/1, etc.), then taking the total transmitted power signal recorded for the second sample point and dividing it by the total transmitted power signal recorded for each of the remaining samples points (i.e., 3/2, 4/2, 5/2, 6/2, etc.), and repeating this process until reaching 16,000/15,999. Alternatively, each sample point could be the numerator and the remaining sample points the denominator (i.e., 1/2, 1/3, 1/4, 1/5, etc.), or sample points could be grouped in sets of sample points, which are averaged together and then divided by the next set of averaged sample points, etc. The key in each case is to develop a set of ratios that can be compared to other ratios for each scan performed by the sensor.

In this L-21 algorithm embodiment, the total transmitted power signals recorded for the 16,000 sample points are grouped into clusters or sets of five sample points that are then averaged. Dividing the 16,000 sample points into clusters or sets of five points would result in 3,200 (16,000/5=3,200) clusters or sets. The first cluster is divided into the second cluster, and then the first cluster is divided into the third cluster, etc., up until the first cluster is divided into cluster 3,200. This process then continues with the second cluster divided into the third cluster, the second cluster divided into the fourth cluster, etc. This is repeated until cluster 3199 is divided into cluster 3,200, to develop the complete set of desired ratios. The number of sample points included in a cluster could be a number other than five. Five sample points is used to explain this embodiment since this number of sample points has yielded good results in initial testing, however, additional cluster sizes may yield better results. Generally, clusters offer an advantage over individual sample points because the clusters are less sensitive to frequency shifts that can be introduced by the sample, variations in scanning apparatuses and other external factors.

Once a number of scans of a patient have been performed (the patient having different known glucose levels during each scan) and complete spectral data sets of desired ratios have been developed for each scan, a ratio matrix of the clusters is developed. FIG. 14 illustrates a ratio matrix of the clusters from a total of twelve glucose levels scanned for a patient. A number of different glucose levels could have been used, such as fewer glucose levels, or a first minimum number of glucose levels when a number of registered patients in the database is below a first registration count, and a second minimum number of glucose levels when the number of registered patients is greater than or equal to the first registration count. The minimum number of glucose levels to be used varies with respect to the number of registered patients and other factors. For instance, the minimum number of glucose levels can be set according to an accuracy level associated with the determination of an unknown sample. If a minimum of six glucose levels is used, and this yields a determination accuracy below the desired accuracy, then the number of glucose levels should be increased accordingly.

It is generally believed that scanning a high number of glucose levels, such as twelve, would yield better results, especially if each patient's glucose levels were scanned under different conditions, such as different atmospheric pressures, higher and lower levels of humidity, higher and lower levels of ambient temperatures, higher and lower levels of skin temperatures, etc. In the absence of being able to change glucose levels as well as other environmental and patient conditions, it may be necessary to factor out the environment and patient conditions, which can be done through application of one or more correction factors.

An embodiment of a correction factor application uses different measured scan parameters to compensate for changes to analytes other than glucose that occur in response to the patient drinking the sweetened liquid, and other variables such as the patient's temperature, the patient's hematocrit levels, the patient's blood pressure level, etc., which can be measured by means other than the commercial blood glucose analyzers 1204 and 1206 shown in FIG. 12. For example, instead of correlating power as described above, phase and other scan parameter correlations can be established for the variables other than glucose, and their corresponding correlation coefficients used to identify frequencies to be avoided when establishing glucose concentration. Also, in addition to single variable linear regression calculations described below, multiple linear regression calculations can be used to identify frequencies to be avoided in the presence of multiple variables.

Another correction factor embodiment measures a substance of interest using, say, power or impedance, at a scan frequency sensitive to the substance and one or more measurements of power or impedance at scan frequencies not sensitive to the substance, but sensitive to additional confounding substances known to be present in the patient or the sample. The changes in power or impedance due to the additional substances can be subtracted from the sensitive frequency measurements of the substance of interest. The remaining change in power or impedance gives a measure of concentration of the substance in the patient or sample.

The next step in the L-21 algorithm process is to take each row of ratios and the results from the glucose meter and perform a least squares analysis (such as through utilization of the LINEST function in MICROSOFT EXCEL® software, manufactured by MICROSOFT®) to determine how many rows of ratios within the ratio matrix of FIG. 14 consistently correlate to glucose levels. In this context, the term "consistently correlate" means that the $R^2$ value for the ratios within a row is 1 or close to 1. If the $R^2$ value for the ratios within the row is zero or close to zero, then the row of ratios does not correlate.

The L-21 algorithm embodiment uses the least squares method to calculate a straight line that best fits the data. The accuracy of the line calculated depends on the degree of scatter in the data. The more linear the data, the more accurate the result of the least square analysis. When you have only one independent x-variable, the calculations for the slope of the line (m) and the y-intercept (b) are based on the following formulas:

$$m = \frac{\sum (x - \bar{x})(y - \bar{y})}{\sum (x - \bar{x})^2}$$

$$b = \bar{y} - m\bar{x}$$

where $\bar{x}$ (x-bar) and $\bar{y}$ (y-bar) are sample means. The least squares method can also be used to calculate a polynomial that best fits the data, such as a quadratic, cubic, or other higher order polynomial function. If the data cannot be "fitted" with a straight line function, then a polynomial function can be used.

Figure 15:
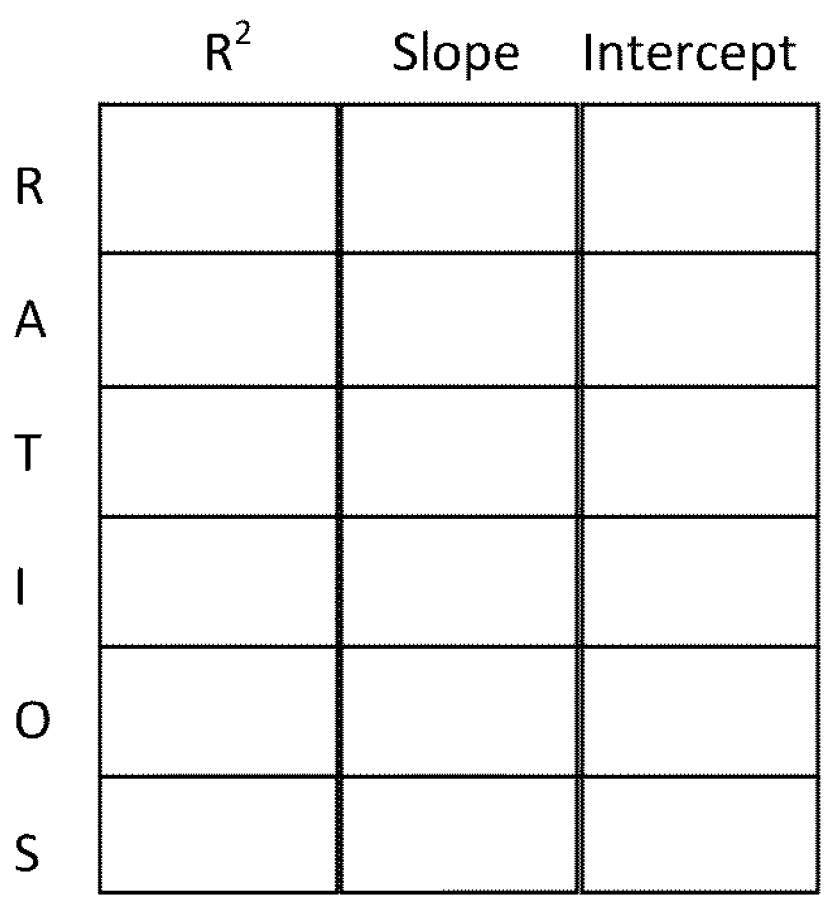

For each ratio within a row having an $R^2$ value of 0.5 or higher, the $R^2$ value, slope and y-intercept are added to a preliminary registration table, as illustrated in FIG. 15. Once all of the rows within the ratio matrix of FIG. 14 have been evaluated and the table of FIG. 15 has been completely populated, the table is sorted to determine the 21 ratios with the highest $R^2$ values. These 21 ratios and each corresponding $R^2$ value, slope and y-intercept become the user's or patient's registration table. As with other numbers noted herein, the number of 21 ratios may not ultimately yield the best result for each patient or all patients. Hence, another number of ratios may be better, but for the purpose of describing the L-21 algorithm embodiment, the 21 ratios with the highest $R^2$ values seem to offer the best predictability of other numbers tried. An embodiment can use less than 21 ratios or more than 21 ratios. Moreover, it may turn out that picking ratios with the highest $R^2$ values excludes certain ratios that include important information for other reasons. For example, it may turn out that knowing which ratios have $R^2$ values closest to zero can be important for other reasons, such as determining the presence and quantity of other substances in the sample, such as a protein or another molecule aside from glucose.

Once the registration table has been completed for a patient, it can be used to predicatively determine the patient's glucose level when it is not also known through use of a glucose meter. Hence, a scan of the patient would be performed and analyzed in view of the registration table to determine the patient's glucose level at the time of the scan. The formula used to predict glucose levels is as follows:

$$P_1 = (R_m)\text{Slope} + \text{Intercept}$$

where $P_1$ is a predicted glucose level and $R_m$ is the measured ratio that corresponds to the slope and y-intercept. This prediction is then performed for each of the 21 ratios in the patient's registration table and the result of the 21 predictions is averaged to determine the patient's glucose level at the time of the scan.

A biometric identification embodiment referred to herein as the True Call algorithm utilizes data collected from spectral data sets and executes a calculation at each sample frequency that asks: Is this a spectra for a specific person, such as "Harra"? If the answer comes back "Harra", that frequency is tagged as "True Call" for Harra, and the next frequency is tested. This procedure was repeated for each of a number of other people in a data file, and out of the 3,200 frequencies, 988 frequencies correctly identified one of the people in the data file at least half the time. Even if only 20 frequencies correctly identified a person half the time, the chance that someone would be mis-identified would be $0.5^{20}$, which equals 0.00000095.

The True-Call algorithm approach can also be used to identify something by taking a new spectra (spectral data set) and comparing it against a "Library" of known substances, such as wines, liquids, known glucose/distilled water solutions in sealed test tubes, etc. The True-Call algorithm consists of an enrollment phase and an identification phase.

Figure 16:
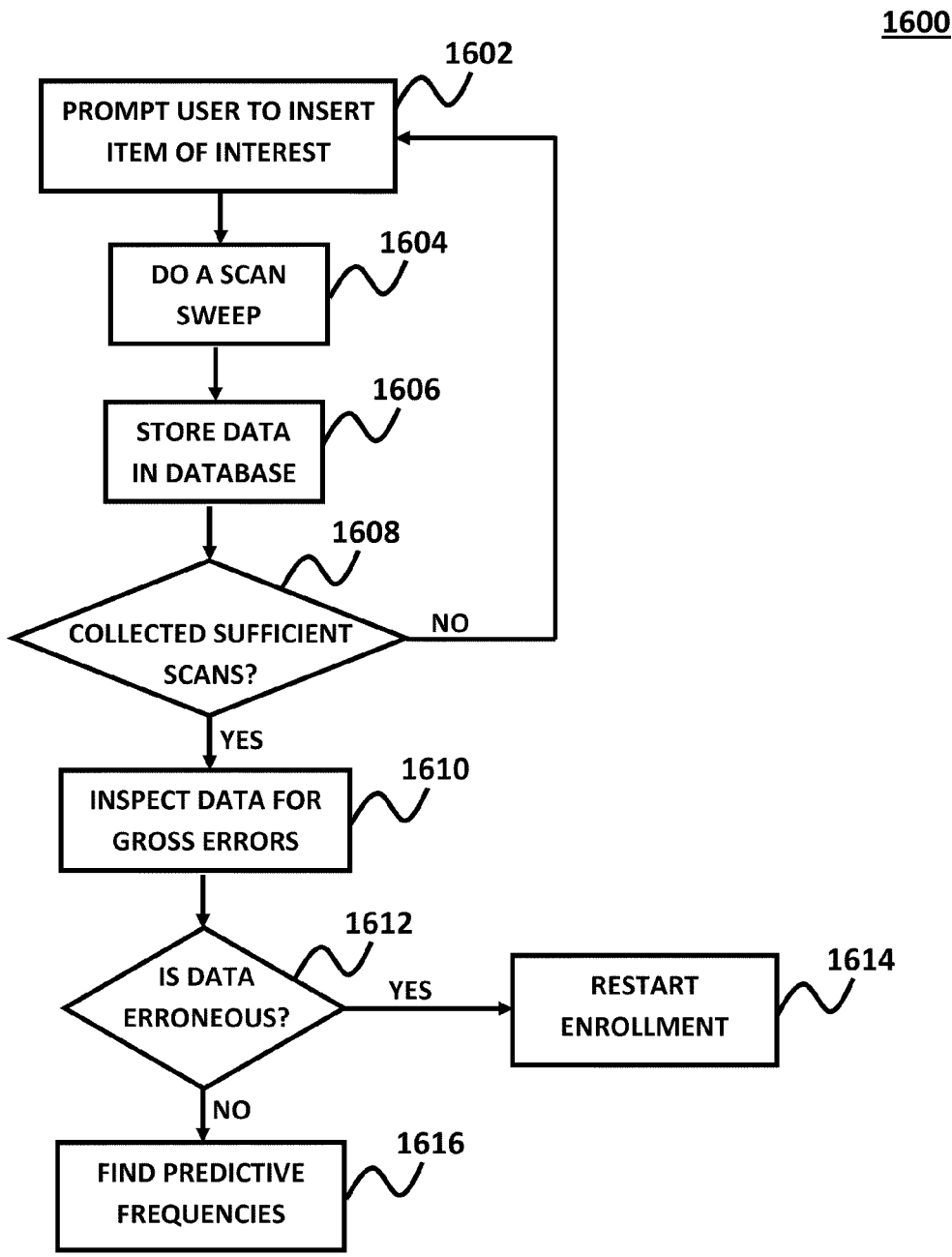
FIG. 16 is a flow chart representing the enrollment process of the True-Call algorithm embodiment.

FIG. 16 shows a flowchart 1600 describing the enrollment process of the True-Call method. Enrollment begins by inserting the item of interest, the sample, such as a finger, into a scanning apparatus, step 1602, and capturing either one or more spectra, step 1604 as further described below. If multiple spectra are captured, the multiple spectra can be averaged in order to improve the signal to noise ratio. Multiple scans for each item are obtained by removing and reinserting the sample into the scanning apparatus for each scan. Such a procedure can be necessary to capture effects of sample placement error, sample rotational error, among other types of errors. As noted above, the term "spectra" refers to spectral data sets of pairs of frequency and corresponding signal amplitude measurements. The signal amplitude can be for transmitted, reflected, total net power, or a related component normalized or not. The types of item to be scanned can include many different items, including wines, other liquids, objects, etc. Multiple enrollment spectra are taken under normal environmental or application conditions and then processed to make sure data is qualified, error free, self consistent, etc.

Step 1604 performs a scan sweep of the item of interest to collect the spectra data. The data collected is stored in a database or in an alternative storage system, step 1606. Step 1608 checks to see whether enough scans have been collected. If additional scans are needed, then the user is prompted to insert the item of interest into the scanning apparatus again in step 1602. This number can depend on the nature of the sample, with biological samples requiring more scans due to variations in the sample with each scan (fingers inserted at different depths, fingers turned, fingers sweaty and then dry, fingers applying more pressure inside the scanning apparatus one time and less the next, etc.). After enough scans have been collected, the data is inspected for gross errors, step 1610, by calculating the average, standard deviation, and sum of standard deviations of the spectral data scans. This procedure allows for the identification of erroneous or questionable spectra taken at the wrong moment, such as when the item was moving instead of being at rest. If the data is erroneous or questionable, step 1612, then the enrollment process is restarted, step 1614.

If the data is error free, qualified, and self consistent, then step 1616 finds predictive frequencies for the item of interest. For every given frequency, the frequency is polled by asking whether the spectra is a specific instance of an item. For example, if the True Call algorithm is being used to identify a user X, each frequency would be polled by asking whether the spectra at the given frequency is a spectra for user X. If the response was user X, then that frequency is tagged using a number, a Boolean, a string, or some other type of identifier. The polling is done by taking each scanned spectra K from the multiple scanned spectra, and then identifying the average spectra value along each frequency J which most closely matches the value at frequency J of the scanned spectra K. If the average spectra value which most closely matches is the average spectra value of the current item of interest being enrolled, then the frequency J is tagged as correctly identifying the item of interest.

The spectra for each item can be stored in a database or stored in a simple text file as raw text or organized using a markup language such as XML. For each item, the average of the enrollment spectra can also be stored in some fashion. The average value of the enrollment spectra can be updated by conducting a second enrollment and capturing a second set of enrollment spectra. The raw data from the first enrollment can also be combined with the raw data from the second enrollment, with the average of the first and the second enrollments combined being computed. The first enrollment and the second enrollment can also be combined, and the combined enrollment spectra filtered in various ways. For example, outliers can be discarded, or spectra more than one standard deviation from the mean can be discarded, etc. The user may also choose to manually discard spectra enrollment if the identification process performs below a desired accuracy. For example, during a biometric application, a user may have positioned the wrong finger in the scanning apparatus during enrollment, or the user may have positioned the finger consistently in the wrong orientation, making it appear as if the enrollment spectra were correct when it was not. In this case, if the user was not identified properly after several tries, then the user could clear the existing enrollment spectra and conduct another enrollment.

For each item in the database or storage, the average of multiple enrollment spectra differential amplitudes are used to identify the item. For identification, an item is placed in the scanning apparatus and spectra over a range of frequencies or over specific frequency values are captured. The captured frequencies of the unknown item are compared against the database. For each frequency J in the captured frequencies, the frequency J is used as the search index to obtain average spectra values, obtained during enrollment, that match the frequency J. By checking whether any of the entries along each frequency match the captured spectra value associated with frequency J. If an exact match is not found for the spectra value at frequency J in the entries in the database for frequency J, then the average spectra that is closest in value to spectra value is marked as the matching spectra. A counter is incremented for the matching average spectra. After all frequencies in the table or database have been checked, a first candidate associated with the highest matching count is identified as the correct candidate. If a count difference between the first candidate with the highest matching count and a second candidate with the second highest matching count is X, then an estimate of probability of misidentification of the first candidate is $0.5^X$. For example, if the first candidate had a matching count of 1,000, and the second candidate had a matching count of 800, then the probability of misidentification of the first candidate would be approximately $0.5^{(1,000-800)}$ which is equal to 6.22e-61, which is an astronomically low probability. Even if the count difference had been only 10, the probability of misidentification of the first candidate would have been approximately 0.00098. This makes the True-Call algorithm a very powerful identification tool.

Figure 17:
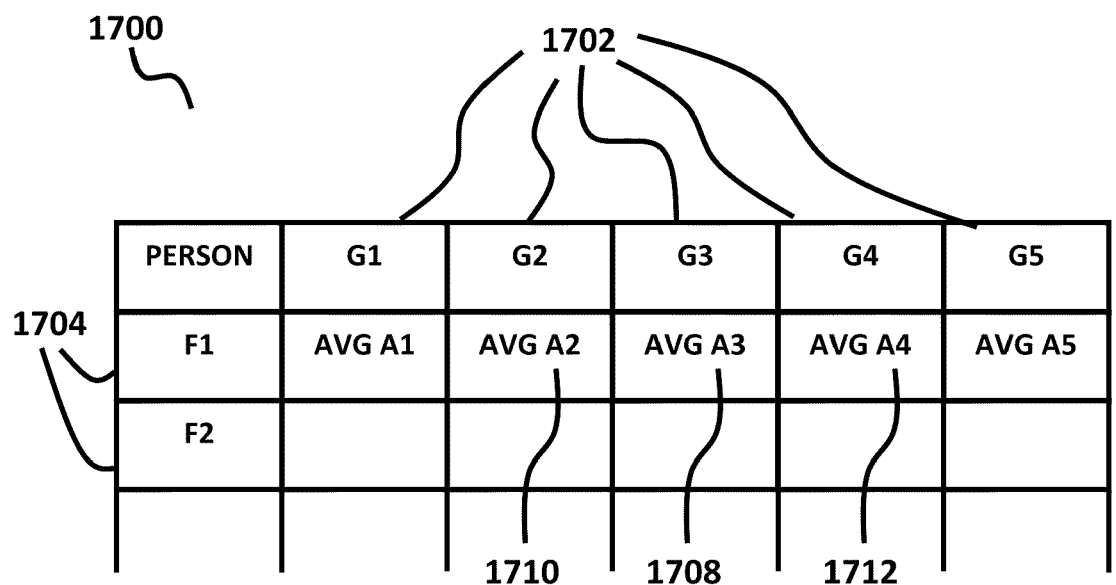
FIG. 17 is a representation of a table used for an embodiment of the True-Call algorithm.

FIG. 17 illustrates a table 1700 used for an embodiment of the True-Call algorithm. Each column 1708 contains the average spectra differential amplitudes collected during enrollment for a user. Each row 1704 contains the transmitted power at various frequencies, starting at frequency F1 through frequency FN. The table may also be structured in other ways, or additional tables may be used to store additional information. For example, the actual raw data readings may be stored in a separate table, with table 1700 only containing the average values from the separate table. During the identification process further described below, the True-Call algorithm iterates over every row 1704 in table 1700, identifying the column entry along each frequency which most closely matches the unknown spectra value at each frequency. For example, row 1704 for frequency F1 would be searched to identify the column 1702 which most closely matches the unknown spectra value at frequency F1.

In an embodiment, the N spectra values greater than and closest to the match found and the N spectra values less than and closest to the match found can also be counted, instead of only counting the single most approximate match. For example, if the N was 1, then the match found, and the next spectra value greater than the match found but closest to the match found, and the next spectra value less than the match found but closest to the match found, would also be counted. In FIG. 17 if 1708 was the match found for the current unknown spectra value at frequency F1 and N was set to 1, then 1710 and 1712 would also be counted. For A2 the N=1 neighbors would be A1 and A3, for A1 the N=1 neighbors would be only A2. Sorting can be used to organize spectra values as desired, but is not required to identify the immediate value neighbors to the match found. The immediate value neighbors can also be identified by iterating one or more times over the unsorted spectra values for a given frequency.

In an embodiment, neighbors across frequencies are counted as well. Instead of finding the N neighbor values within a frequency (a row 1704), the M frequency neighbors located on the same column 1702 as the match found would be counted. If a match was found in the third column of the frequency F1 row and M was set to 1, then the frequency neighbor would be the entry on the third column of the frequency F2 row. If the match was found on the third column of the frequency F2 row, then the M=1 neighbors would be the third column entries on frequency rows F1 and F3. Obviously, if this embodiment is utilized, the spectra values would need to be sorted in advance before attempting to count entries in other columns.

Figure 18:
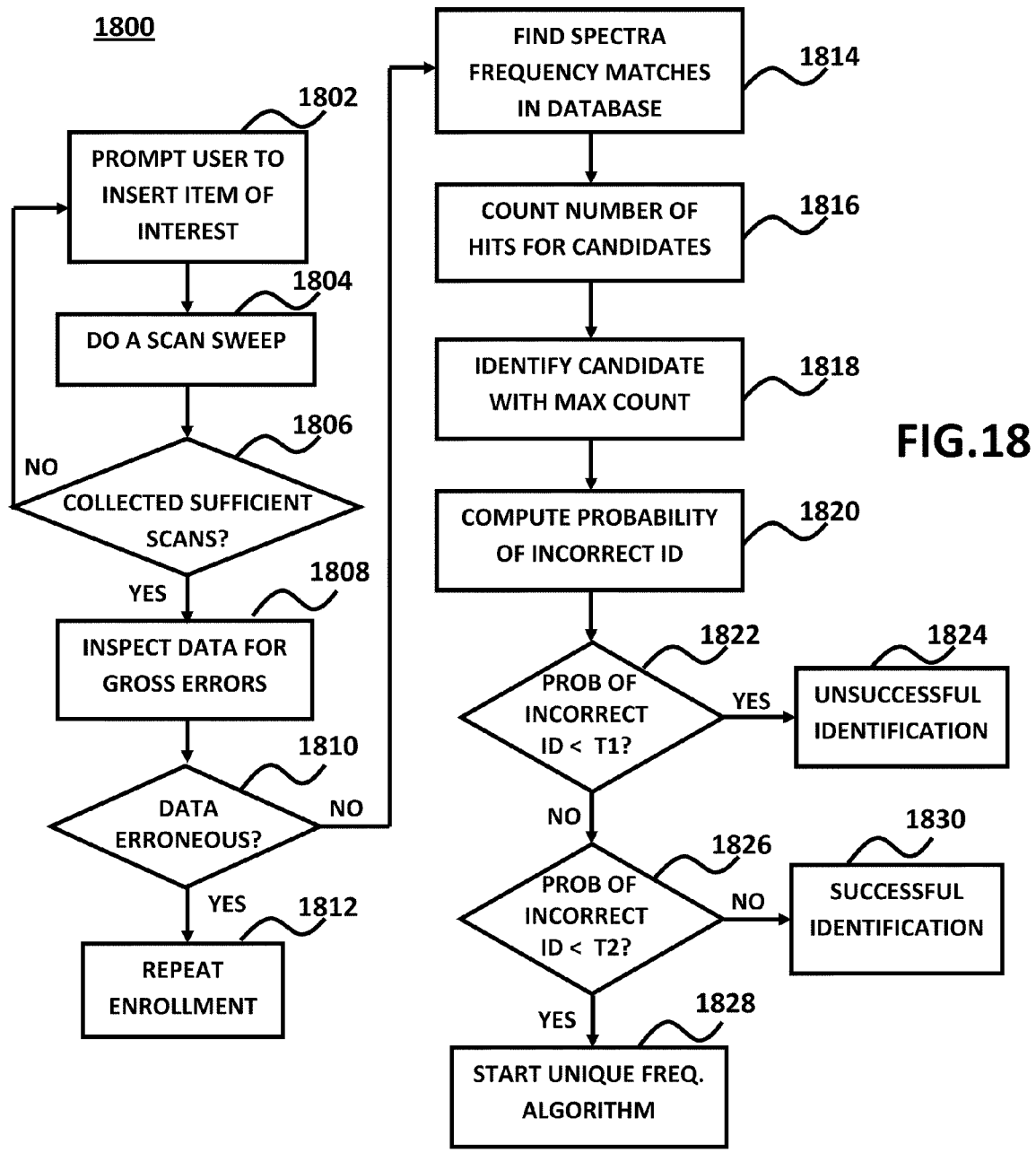
FIG. 18 is a flow chart representing the identification process of the True Call algorithm embodiment.

FIG. 18 shows a flow chart 1800 of the identification phase. Step 1802 prompts the user to insert an unknown sample into the scanning apparatus. Step 1804 performs a scan or sweep, and step 1806 checks whether enough sweeps have been collected. If additional sweeps are needed then the user is prompted to insert the unknown sample into the scanning apparatus in step 1802. The data collected is inspected for gross errors in step 1808 by computing the average, standard deviation, and sum of standard deviations of the spectra data sets. This procedure allows for the identification of erroneous or questionable spectra taken at the wrong moment, such as when the unknown sample was moving instead of being at rest. If the data is erroneous, step 1810, then the identification process is restarted, 1812. If the data is error free, then step 1814 finds spectra frequency matches in the database. This consists of taking the average of the values along each frequency of the scanned spectra and finding the closest matches along each frequency in the database, as described above.

Step 1816 counts the number of hits or matches for each candidate in the database. Step 1818 identifies the candidate with the greatest hit count, and step 1820 computes the probability of the candidate having been identified incorrectly (incorrect probability). If the incorrect probability is less than an unknown candidate threshold T1, step 1822, then the user is notified that the unknown sample could not be identified, step 1824. If the incorrect probability is greater than or equal to the unknown candidate threshold T1, but still less than a confidence threshold T2, step 1826, then the suspected candidate identified is confirmed with a second unique identification algorithm, step 1828, further disclosed herein. If the incorrect probability is greater than or equal to the confidence threshold T2, step 1826, then the user is notified of a successful identification and the candidate ID is presented to the user, step 1830.

As discussed above, if the count difference is less than a count difference threshold, meaning that the confidence threshold was not met, then a second unique frequency algorithm is used to confirm the suspected candidate selected. The second algorithm ranks the top few likely candidates selected, say G3, G1, and G4, in order to confirm the candidate selected by using a set of frequency values that are more or less unique to each specific candidate's spectra. When the enrollment scans are completed, the True Call frequencies found to have successfully distinguished the enrollee as distinct from other frequencies for other people enrolled in the database are put into a frequency table for the enrollee. Later, any frequencies that tend to be common (e.g., shared by half of the other people in the database) are removed from the enrollee's set of frequencies in the unique frequencies table.

The unknown spectra, as mentioned above, are interpreted for each of the top few likely candidates at only those unique frequencies in the unique frequencies table corresponding to the top few likely candidates. If the unknown spectra are for one of the likely candidates, say G3, a comparison of the unknown spectra amplitudes with the amplitudes in G3's enrollment spectra at each of G3's unique frequencies will show relatively small differences. This comparison can be performed by calculating the square of the difference between the unknown spectra amplitudes and the amplitudes in G3's enrollment spectra at each unique frequency and then calculating the sum of these squared differences. Since the amplitudes vary considerably across the spectra, it is best to normalize the sum of squared differences by dividing by the average of the absolute amplitudes at all frequencies scanned in the spectra, also squared (see formula below). Also, since each likely candidate may have a different number of unique frequencies, it is best to multiply by the ratio of the number of frequencies scanned in the spectra divided by the number of unique frequencies for candidate G3. The formula for this figure of merit calculation for likely candidate G3 is:

> Figure of Merit for $G3$=(sum of (differences at $G3$'s unique frequencies between unknown spectra amplitudes and $G3$'s enrollment spectra amplitudes)$^2$)×(number of frequencies scanned in spectra)/((average of absolute amplitude of $G3$'s enrollment spectra)$^2$×number of $G3$'s unique frequencies).

This calculation is then repeated for likely candidates G1 and G4, and if the candidate with the smallest figure of merit passes a threshold test, that candidate is confirmed.

For example, a new unknown spectra is identified as being user G3 with the True Call algorithm, but G1 and G4 are the next most likely choices. The second unique frequency algorithm verifies that the new unknown spectra belong to user G3 by comparing the figures of merit described above and selecting the candidate with the lowest figure of merit. If the differences between the figures of merit for user G3 and users G1 and G4 exceed a threshold value, or exceed a number of standard deviations, then the identity is confirmed.

An embodiment consists of a biometric identification algorithm, where one or more independent algorithms separately analyze a biometric scan (a scan performed of a person using a scanning apparatus), and each makes an identification determination. The identification determination from each algorithm counts as a vote for a potential identity candidate, with the potential identity candidate with the most votes being the actual identity identification. Alternatively, the identification determination from the one or more independent algorithms can be combined in other ways, such as by applying different weights to the contributions by each algorithm. The one or more independent algorithms can also be used in combination, such as by applying them sequentially, with the output of a first algorithm feeding into the input of a second algorithm. The first algorithm can reduce the identity of a user or a sample to a set of candidates. The set of candidates can be input into the second algorithm, which further reduces the set of candidates to a second set of candidates. The second set of candidates can subsequently be input into a third algorithm, with the process ending when the output of one of the algorithms is a single candidate or if the set of candidates cannot be further reduced after passing through the various algorithms.

In an embodiment, a minimum identification threshold can be used to discard majority scores or votes if the total score or votes for a potential candidate are below the minimum identification threshold. If an algorithm received the majority weighted score of 55, but a minimum identification threshold was set at 60, then the result would be an unknown.

The weights assigned to the result of the various algorithms can be set based on empirical observations. For example, if it is known that an algorithm A is particularly robust to noise, then a higher weight can be assigned to the result of algorithm A. Likewise, an algorithm that does not have robust performance can be used as a supplementary algorithm and assigned a lower score, providing support to more robust algorithms. Alternatively, the choice of algorithms used and the corresponding weights can be dynamically varied depending on one or more conditions. These conditions can include the current temperature of the sample, current ambient temperature, and the amount of pressure applied by the sample during measurement. If algorithm B is known to perform well under certain conditions, such as when the sample's temperature is above or below a certain point, or when using a certain frequency group, then it can be assigned a higher weight when those conditions are identified. Other conditions can depend on transient conditions, such as the time of day. For example, if an embodiment is being used for biometric identification of users, then the algorithms used or the choice of weights used for each algorithm can be adjusted during and after lunch times. If it is expected that users will consume food during lunch times and with this likely to raise the average glucose level of users, then this can be taken into consideration.

In an embodiment of the biometric identification algorithm, a user goes through a registration process with the goal of building a unique identity profile (identity profile) for the user, the unique identity profile subsequently stored in a database or other storage system. The identification is not restricted to users, but can also be applied to liquids or other solid substances. From here on, the term "sample" will be used to refer to either a user or other material. The biometric identification of the sample is done on a determination process.

A sweep consists of placing the patient's finger, or some other sample of interest, in the scanning apparatus, wherein the transmitter transmits a series of RF signals starting at a base frequency and stepping up numerous times to higher frequencies until reaching a maximum frequency, or only scans at a number of predetermined frequencies. Numerous different frequency ranges can be utilized. An embodiment uses a frequency range between about 10 MHz and about 12 GHz. The number of steps taken within the frequency range can also vary significantly. An embodiment uses an equal number of about 3,200 sampling points. The total transmitted power signal received by the receiver at each of the 3,200 sampling points is then recorded and processed.

During the registration process a sample of interest is scanned multiple times using an embodiment of the scanning apparatus. Each scan is referred to as a sweep. In the case of a user, the user's finger can be scanned. In the case of a liquid, a small amount of the liquid can be placed inside a test tube or some other container which can be fitted inside the scanning apparatus. The flow through sensor can also be used for the registration process. An embodiment of the unique identity profile consists of recorded measurements by the scanning apparatus, and the result of various analyses conducted on the recorded measurements. A subset of the information stored for each user in the database is used to subsequently determine the identity of a user during a determination process.

In an embodiment, a single sweep is used to build the identity profile for the user, such identity profile subsequently being used to verify the identity of the user. A higher number of sweeps increases the accuracy of the system, as the numerous sweeps allow for normal variations in the user to be recorded and for noise in the data, whether due to improper sample positioning or too much pressure applied by the sample, to be filtered out. In an embodiment, the number of sweeps is five or more, although fewer sweeps could be used.

The identification of a sample is not restricted to users. The identification can be used to identify properties of a sample. For example, a sample can consist of a fluid in a tube inserted into the scanning apparatus. A profile of the fluid can be built on the database and subsequently used for identifying fluids with similar properties. As previously discussed herein, the authenticity of liquids and other objects, such as money, bonds, antiques, documents, etc. can be verified.

After a number of sweeps have been completed, the second step extracts raw data associated with a number of frequency clusters. In an embodiment, a frequency cluster consists of one or more frequency values picked manually through observation of the spectra for a number of people based on two criteria: (1) the variation among the different people needs to be significantly large; and (2) the variation for the same person at difference scans needs to be relatively small. The frequency values picked for the clusters may be dependent on the sample and the intended application. For a biometric identification application where the sample is a finger, a total of about 16 frequency clusters are utilized that each fall within a spectrum between about 2.0 GHz and about 6.3 GHz. The frequency points in each cluster are contiguous frequencies that were generated by the transmitter 18. Although the clusters are manually selected in this embodiment, they could be determined by the computer 16 by seeking the largest coefficient of variation for different people with a minimized coefficient of variation for the same person.

Clusters are utilized to achieve relative stability of measurement components. Once the clusters are selected, the average or mean values of the amplitude data within each cluster is calculated and used as a single "point". The calculated means or averages for a cluster from the 16 clusters for each sweep include average values of the amplitude measurements for the cluster, but can also include average slopes for the cluster, average curvature for the cluster, and the log magnitude sum for the cluster. Hence, each cluster becomes a single point consisting of a set of points and associated data.

The fourth step calculates statistics for each cluster over all the sweeps. For example, if there were a total of five sweeps, each sweep with 16 clusters, then the statistics would look at the first cluster from the first sweep, the first cluster from the second sweep, the first cluster from the third sweep, the first cluster for the fourth sweep, and the first cluster from the fifth sweep, etc., continuing with the other 15 clusters. The statistics include calculating the average and the standard deviation for the measurements, the average and the standard deviation for the slopes, and the average and the standard deviation for the curvatures.

The fifth step sorts the cluster order based on the average sum of log magnitude over all the sweeps. The maximum four cluster numbers and the minimum four cluster numbers are determined based on the sorted cluster order. The sixth step calculates the sum of difference squared for each sweep using cluster averages. The sums include the sum for measurements, the sum for slopes, and the sum for curvatures.

The seventh step calculates statistics for the sums of difference squared. The statistics include the average sum of difference squared for measurements, the average sum of difference squared for slopes, the average sum of difference squared for curvatures, the standard deviation of the sum of difference squared for measurements, the standard deviation for the sum of difference squared for slopes, the standard deviation of the sum of difference squared for curvatures.

The final step sets the tolerances. The measurement difference squared tolerance is set to four times the standard deviation of the measurement difference squared. The slope difference squared tolerance is set to four times the standard deviation of the slope difference squared. The curvature difference squared tolerance is set to four times the standard deviation of the curvature difference squared.

In an embodiment of a biometric identification application utilizing the identity profiles built above and the scanning apparatuses described herein, a set of fields corresponding to measurements and statistics computed for a person can be stored in a database. The information stored in the database for each person can include the average of difference squared for measurements, measurement of difference squared tolerance, average sum of difference squared for slopes, slope difference squared tolerance, average sum of difference squared for curvatures, curvature difference squared tolerance, the M maximum sum of log magnitude frequency clusters, and the N minimum sum of log magnitude frequency clusters. In addition, for each user, a set of additional reserved parameters may also be saved on the database for each user. For example, one of the additional reserved parameters can store the standard deviation of the sum of difference squared for measurements.

An embodiment of the determination process begins by performing a scan sweep. Raw data is collected at the N frequency clusters, where N may be 16 or an alternative number of frequency clusters. Finally, average values are calculated for the clusters. The average values for each cluster include the average values of measurements, the average slopes, and the average curvature. Other statistics computed for each cluster include calculating the log magnitude sum for each cluster. Sorting the cluster order for the sum of log magnitude. The maximum four cluster numbers and the minimum four cluster numbers are determined based on the sorted cluster order.

For determining the identity of a scanned individual, the first step consists of calculating the sum of difference squared against people in the database. The sum of difference squared can be computed for measurements, for slope, for curvature, or for some other property. The second step finds a set of candidates in the database that have the smallest sums of difference squared.

The third step checks the tolerance of the sum of difference squared for each candidate in the set of candidates. Overlap among the set of candidates with the lowest sum of difference squared are determined by checking whether intervals of two or more candidates overlap, with an interval starting at a minimum overlap point and ending at a maximum overlap point. The low end of the interval for a candidate is computed by subtracting the tolerance value from the sum of difference squared. The high end of the interval for a candidate is computed by adding the tolerance value to the sum of difference squared.

If there is no overlap between any intervals, then a determination is made using a determination candidate from the set of candidates with the lowest sum of difference squared. The measured sum of difference squared is compared against the average sum of difference squared for the determination candidate. If the sum of difference squared is within the tolerance interval, then the determination candidate is identified as the correct identity and the determination process completes. If the sum of the difference squared is outside of the tolerance interval, then the identity cannot be determined and is unknown, and the determination process completes.

If there is overlap among the set of candidates with the lowest sum of difference squared, then the database is checked for each candidate in the set of candidates. In an embodiment, only the candidates in the set of candidates that have any overlap are checked in the database. Alternatively, if there is overlap between two candidates in the set of candidates, but the two candidates are not the candidates with the lowest sum of difference squared among the set of candidates, then only the candidate with the minimum sum of difference squared is checked in the database. The step of checking in the database consists of comparing the sum of the measured sum of difference squared with the average sum for the candidates in the set of candidates. If the sample sum of difference squared is within tolerance of the average sum of difference squared for the candidates in the set of candidates, then all candidates in the set of candidates are possible identification candidates. If the sample sum of difference squared is outside of the tolerance, then the sample is unknown and a determination cannot be made.

A candidate in the database is compared against a sample during determination by first checking the cluster numbers with the maximum sum of log magnitude. Second, the cluster numbers are checked with the minimum sum of log magnitude. In an embodiment, N maximum sum of log magnitude cluster numbers and M minimum sum of log magnitude cluster numbers would be identified. For example, if there are a total of 16 frequency clusters, with N equal to 4 and M equal to 4, then the four maximum sum of log magnitude cluster numbers and the four minimum sum of log magnitude are identified. In an embodiment, N is not equal to M. Sorting a sequence of numbers and identifying the maximum N elements and the minimum M elements of the sorted, or unsorted, sequence is well known in the art and need not be further described herein.

The N maximum sum of log magnitude clusters and the M minimum sum of log magnitude clusters of a possible candidate in the database are compared against the unknown sample. A set of points can be awarded based on a set of matching criteria. These matching criteria can include the N maximum sum of log magnitude cluster numbers (N LOG MAX) matching in order, matching out of order, or not matching at all, and similarly for the M minimum sum of log magnitude cluster numbers (M LOG MIN). A positive match consists of a cluster number being common in the possible candidate and in the unknown sample.

If there are a total of 16 frequency clusters with four entries in N LOG MAX and four entries in M LOG MIN, then the entries in N LOG MAX can be "15 03 08 12" and the entries in M LOG MIN can be "02 11 14 05", with "15" being the cluster number with the highest sum of log magnitude number out of all 16 frequency clusters, and where 12 is the smallest of the four maximum sum of magnitude cluster numbers. The cluster number "02" in M LOG MIN is the smallest sum of log magnitude number out of all 16 frequency clusters, and "05" is the highest of the four minimum sums of magnitude cluster numbers. If the matching rules include taking into consideration the order of the elements in the N LOG MAX and M LOG MIN, then the elements in N LOG MAX and M LOG MIN can be sorted, either in increasing or decreasing order. However, the key is that the sorting order matches the sorting order used with the unknown sample, since M LOG MIN of a candidate in the database is sorted in increasing order, and the M LOG MIN of the unknown sample is sorted in decreasing order, then this would yield erroneous order matching.

Figure 19:
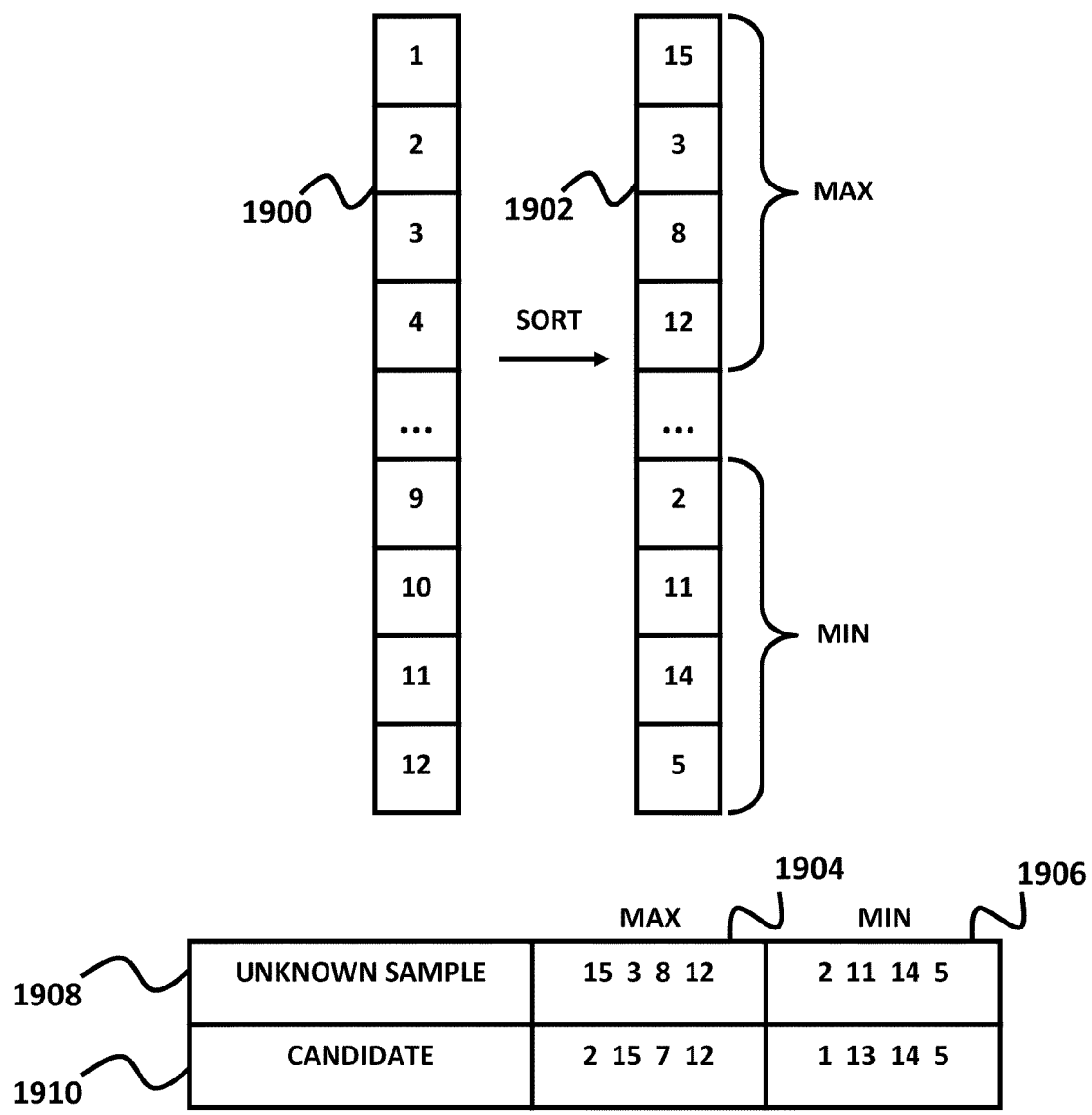
FIG. 19 is a representation of an embodiment of a biometric identification application.

In an embodiment, matching begins by iterating over N LOG MAX of either the unknown sample or a candidate. The first element from N LOG MAX in the unknown sample is searched for in N LOG MAX of the candidate. If the first element is found in both N LOG MAX of the unknown sample and of the candidate, then a certain amount of points can be awarded. If the positions are the same, in this case both being the first element of the respective N LOG MAX, then additional points can be awarded. For example, in FIG. 19, the entry "15" at the top of column 1902 out of columns 1900 and 1902 is a match out of order, because the entry "15" is in the first position in column 1902, but it is in the second position in column 1904 for the candidate row 1910. Whereas, the entry "12" in column 1902 is a match in order because it is also in the last position in column 1904 for the candidate row 1910. The rest of the entries are not matches. In unknown sample row 1908, column 1906 entries of "14" and "05" are matches in order, whereas the rest of the entries are not matches.

In an embodiment, points are added to a matching score depending on the type of match. Two points can be added to the matching score if a match in order is found, one point can be added to the matching score for a match out of order, and zero points are added in case of no matches. In an embodiment, the matching rules and the corresponding points received for a partial or complete match are customizable. Other matching rules can be devised. A match in order can receive points equal to half of the length of either N LOG MAX or N LOG MIN, whereas a match in order can receive points equal to a quarter or some other fraction of the length of N LOG MAX or N LOG MIN.

All of the matching points are added to the matching score. The matching score is used for determination of the identity of the unknown sample. The total matching score is compared against a matching threshold. If the total matching score is below the matching threshold, then the unknown sample is unknown and no determination can be made. The matching threshold can be varied in order to increase or decrease the accuracy of the identification of the unknown sample.

An additional biometric or other sample identification algorithm embodiment consists of a template for each user, consisting of 128 frequencies for each of the four components measured by the scanning apparatus. The four components are the real and imaginary components of transmitted RF signals and the real and imaginary components of reflected RF signals. The set of 128 frequencies defines a template. The test consists of comparing a measurement taken with the template. Then the matches are counted between the measurement and the template, and if a match of about 75% or higher is achieved, then it is a correct identification of the user.

A range can also be defined. The average score for people is expected to be in the 50% range, since the template itself is defined on a composite average. The template for a user is generated by determining how a user's signal amplitude compared to the norm at the given frequency. If the user's value is above the norm or standard value, then the result at that given frequency is encoded as a 1. On the other hand, if the user's value is below the norm, then the result at that given frequency is encoded as a 0. This consists of the process of registering a user and the set of 1s and 0s for the four components define a template or code for a person.

During a determination scan of a first user, the scanning apparatus measurements for the first user are compared with the norm, as during the registration process. The determination of the first user is done by counting the number of matches of 1s and 0s in the determination scan with the registration scan. The count is computed as a percentage of the total possible number of matches. For example, if there are a total of four columns with 128 frequencies, for a total of 512, then the percentage out of 512 that match would give a measurement of determination. In an embodiment, each column or component has a minimum requirement it must meet. For example, each of the four components must match at least 70% or at least 60%, instead of combining them all together. This would prevent one component from having a 90% match and a second component from having a 60% match, which would not yield an accurate determination.

According to an embodiment, when a sample gas volume is introduced to a sample scanning apparatus at atmospheric pressure and scanned, a series of spectral data sets are created, which are then analyzed by the analyzer and processed to determine the existence of and other characteristics of the sample. The application of a magnetic field around the transmitter, receiver and sample chamber may enhance this analysis. This application is well suited for measuring gas within a room, such as to measure air quality, to detect radon levels, or to detect toxic gases. For example, police or hazardous material emergency responders may want to test the air in a room before fully entering to determine if any toxic gasses are present. A collection chamber could be passed through the air in the room (using a long poll or a robot) and closed, and then removed from the room for on-site testing.

According to an embodiment, the sample gas volume could be introduced under pressure to the scanning apparatus via a gas inlet device, then sealed and scanned in the same fashion as noted above. According to an embodiment, the gas sample could be introduced under pressure via a gas inlet device and scanned without sealing the scanning apparatus. Such an embodiment would be ideal for monitoring gases being discharged from a variety of sources, such as the exhaust pipe of a car or the flue stack of a plant for emissions testing, various discharge points in manufacturing processes, etc. In such an embodiment, the gas inlet device of the scanning apparatus would be adapted to fit snuggly to the desired exhaust point. In operation, the exhaust gases would be forced into the gas inlet device where they are channeled to the scanning apparatus for analysis. The transmission and receiver nodes would preferably be positioned inside the scanning apparatus so as to be in contact with the sample, but they could be coated with a membrane to protect them, or position against the sides of the sample chamber, which is in contact with the sample are connected to a transmitter and are used to transmit electromagnetic radiation to the gas sample.

Figure 20:
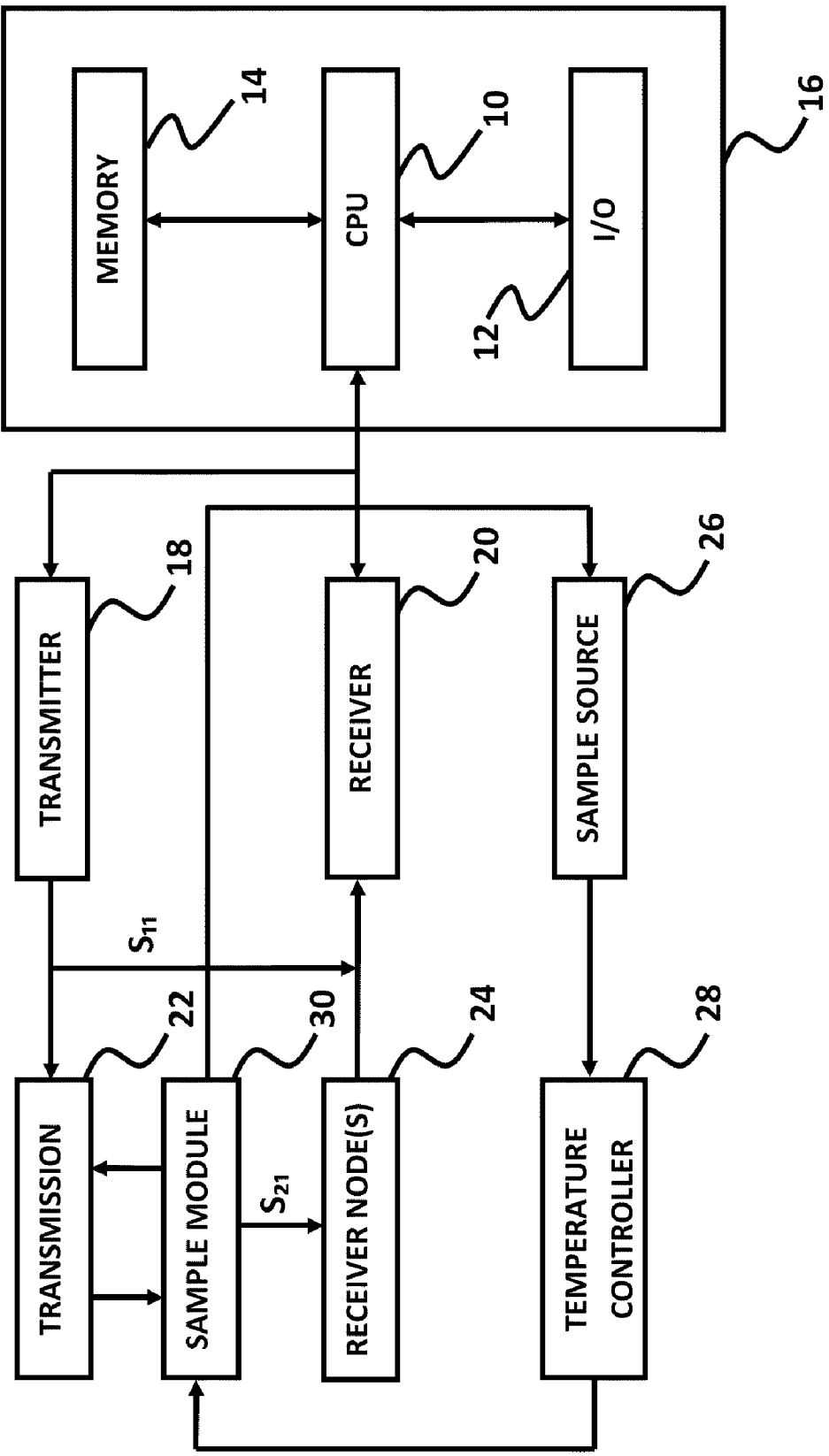
FIG. 20 is a block diagram illustrating the scanning apparatus configured in a manner similar to the flow through sensor of FIG. 4E having a closed system capable of containing a fluid sample.

The scanning apparatuses and analysis techniques described above can be used to detect the presence or quantity of a gas, such as $CO_2$, or even liquids. According to an embodiment illustrated in FIG. 20, when $CO_2$, or any other fluid sample, is introduced into the scanning apparatus in a manner similar to the flow through sensor described above, which has a closed system capable of containing the $CO_2$, and spectra related to the sample is collected, there are clear differences between the spectra related to the air that had been flowing through the scanning apparatus prior to the introduction of the gas and the mixed air and gas subsequently flowing through the scanning apparatus. When the $CO_2$ spectra is compared to corresponding air spectra, there is a large differential between the air and $CO_2$ spectra, indicating that the gas has its own spectra separate from that of the gas. For example, the transmitted power readings associated with the gas are approximately 20 times less than similar readings for a finger, a liquid, or a solid.

While the present invention has been illustrated and described herein in terms of several embodiments, it is to be understood that the techniques described herein can have a multitude of additional uses and applications. Accordingly, the invention should not be limited to just the particular description and various drawing figures contained in this specification that merely illustrate embodiments and applications of the principles of the invention.

What is claimed is:

1. A method of identifying a gas sample using a gas sample scanning and analysis system including a storage system, comprising the steps of:
    scanning the gas sample with a gas sample scanning and analysis system, the gas sample scanning and analysis system including a transmitter for transmitting a series of electromagnetic signals, each of the signals among the series of electromagnetic signals having a transmitted amplitude over a plurality of sample points within a range of frequencies, and a receiver for receiving a series of amplitude modified signals based on the series of electromagnetic signals as the series of electromagnetic signals are reflected from or transmitted through the gas sample;
    generating a series of spectral data sets representing at least a scanned amplitude of each of the signals over the plurality of sample points;
    generating one or more composite spectrograms from the series of spectral data sets;
    analyzing the one or more composite spectrograms to identify a characteristic of the gas sample, the characteristic having a first variance that is minimized across the one or more composite spectrograms and a second variance that is maximally different across a plurality of characteristics corresponding to a plurality of other samples in the storage system;
    comparing the characteristic of the gas sample to a plurality of profiles corresponding to a plurality of gasses at a plurality of concentrations stored in the storage system to identify a profile among the plurality of profiles that corresponds to the characteristic of the gas sample; and
    identifying the gas sample based on the profile among the plurality of profiles that corresponds to the characteristic of the gas sample.

2. The method as recited in claim 1, wherein the gas sample is introduced to the gas sample scanning and analysis system at atmospheric pressure.

3. The method as recited in claim 1, wherein the gas sample is introduced to the gas sample scanning and analysis system under pressure.

4. The method as recited in claim 1, further comprising the step of determining the quantity of the gas sample.

5. The method as recited in claim 1, wherein a gas detected is $CO_2$.

6. The method as recited in claim 1, wherein a gas detected is radon.

7. The method as recited in claim 1, further comprising the step of measuring real components and imaginary components of said series of electromagnetic signals received, wherein said real components represent purely resistive properties of said gas sample, and wherein said imaginary components represent capacitive and inductive properties of said gas sample.

8. The method as recited in claim 7, further comprising the steps of:
   registering a known first sample with said gas sample scanning and analysis system based on a variety of known conditions; and
   analyzing a second sample to determine an unknown condition for said second sample, wherein said unknown condition is one that was registered with said gas sample scanning and analysis system using said known first sample.

9. The method as recited in claim 1, wherein said step of analyzing includes comparing said one or more composite spectrograms against a library of known substances.

10. A gas sample scanning and analysis system comprising:
    a scanner module for scanning a gas sample, including a transmitter for transmitting a series of electromagnetic signals, each signal of said series of electromagnetic signals having a transmitted amplitude over a plurality of sample points within a range of frequencies, and a receiver for receiving a series of amplitude modified signals based on said series of electromagnetic signals as said series of electromagnetic signals are reflected from or transmitted through said gas sample, and generating a series of spectral data sets representing at least a scanned amplitude of each signal of said series of electromagnetic signals over said plurality of sample points, said scanner module including a transmitter node having a first dipole antenna connected to said transmitter and a receiver node having a second dipole antenna connected to said receiver; and
    an analyzer module including a memory and a processor for generating one or more composite spectrograms from said series of spectral data sets, analyzing said one or more composite spectrograms to recognize one or more patterns within said one or more composite spectrograms representing one or more characteristics of said gas sample, and making a determination regarding said one or more characteristics based on said one or more patterns.

11. The gas sample scanning and analysis system as recited in claim 10, wherein said scanner module measures a real component and an imaginary component of said series of electromagnetic signals transmitted and a real component and an imaginary component of said series of electromagnetic signals received.

12. The gas sample scanning and analysis system as recited in claim 10, wherein said series of electromagnetic signals transmitted by said transmitter node are within a range of frequencies between about 0.3 megahertz and about 20.1 gigahertz.

* * * * *